US010385058B2

(12) United States Patent
Beaudry et al.

(10) Patent No.: US 10,385,058 B2
(45) Date of Patent: Aug. 20, 2019

(54) PROCESS FOR PREPARING BTK INHIBITORS

(71) Applicant: Genentech, Inc., South San Francisco, CA (US)

(72) Inventors: Danial Beaudry, South Francisco, CA (US); Theresa Cravillion, South San Francisco, CA (US); Francis Gosselin, South San Francisco, CA (US); Ngiap-Kie Lim, South San Francisco, CA (US); Sushant Malhotra, South San Francisco, CA (US); Qingping Tian, South San Francisco, CA (US); Haiming Zhang, South San Francisco, CA (US); Alexander Gmehling, Dottikon (CH); Alec Fettes, Basel (CH); Stephan Bachmann, Basel (CH)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/841,828

(22) Filed: Dec. 14, 2017

(65) Prior Publication Data

US 2018/0230155 A1 Aug. 16, 2018

Related U.S. Application Data

(60) Provisional application No. 62/434,569, filed on Dec. 15, 2016.

(51) Int. Cl.
*C07D 487/04* (2006.01)
*B01J 31/24* (2006.01)

(52) U.S. Cl.
CPC ........ *C07D 487/04* (2013.01); *B01J 31/2409* (2013.01); *B01J 31/2414* (2013.01); *B01J 2231/40* (2013.01); *B01J 2531/824* (2013.01); *C07B 2200/09* (2013.01)

(58) Field of Classification Search
CPC .............................. C07D 404/14; C07D 487/04
See application file for complete search history.

(56) References Cited

U.S. PATENT DOCUMENTS

| 8,716,274 B2* | 5/2014 | Crawford | A61K 31/496 |
| | | | 514/210.21 |
| 8,921,353 B2* | 12/2014 | Crawford | A61K 31/496 |
| | | | 514/210.21 |
| 9,238,655 B2* | 1/2016 | Crawford | A61K 31/496 |
| 9,260,415 B2* | 2/2016 | Crawford | A61K 31/496 |
| 9,782,405 B2* | 10/2017 | Crawford | A61K 31/496 |
| 10,045,983 B2* | 8/2018 | Crawford | A61K 31/496 |
| 2015/0158846 A1 | 6/2015 | Crawford et al. | |

FOREIGN PATENT DOCUMENTS

| WO | 2013/067274 A1 | 5/2013 | |
| WO | WO-2013067274 A1 * | 5/2013 | ........... A61K 31/496 |
| WO | 2014/056083 A1 | 4/2014 | |
| WO | WO-2015082583 A1 * | 6/2015 | ........... A61K 31/496 |
| WO | 2016/050921 A1 | 4/2016 | |

OTHER PUBLICATIONS

C. Sandoval et al., 20 Organic Letters, 1252-1255 (2018) (Year: 2018).*
T.O. Akeng'a et al., 60 South African Journal of Chemistry, 11-16 (2007) (Year: 2007).*
Abhijit Datta Khoje et al., "Reactivity and regioselectivity in Stille couplings of 3-substituted 2,4-dichloropyridines" Tetrahedron Letters 52(4):523-525 ( 2011).
Barry M. Trost et al., "Palladium-Catalyzed Dynamic Kinetic Asymmetric Transformations of Vinyl Aziridines with Nitrogen Heterocycles: Rapid Access to Biologically Active Pyrroles and Indoles" Journal of the American Chemical Society 132(44):15800-15807 (Nov. 10, 2010).
International Search Report for PCT/EP2017/082723, pp. 9 (dated Jun. 6, 2018).
Written Opinion for PCT/EP2017/082723, pp. 10 (dated Jun. 6, 2018).

* cited by examiner

*Primary Examiner* — Alexander R Pagano
(74) *Attorney, Agent, or Firm* — Mark D. Kafka

(57) ABSTRACT

Methods for preparing the Bruton's Tyrosine Kinase ("BTK") inhibitor compound 2-{3'-hydroxymethyl-1-methyl-5-[((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one are provided. Methods for preparing tricyclic lactam compounds are also provided.

54 Claims, 10 Drawing Sheets

PROCESS FOR PREPARING BTK INHIBITORS

CROSS-REFERENCE TO RELATED PATENT APPLICATIONS

This application claims priority to U.S. Provisional Patent Application No. 62/434,569, filed Dec. 15, 2016, the contents of which are hereby incorporated by reference in their entirety.

BACKGROUND OF THE INVENTION

The field of the invention relates generally to methods of preparing the Bruton's Tyrosine Kinase ("BTK") inhibitor compound 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one. The field of the invention further relates generally to methods of preparing tricyclic lactam compounds.

The BTK inhibitor compound 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one of the following structure:

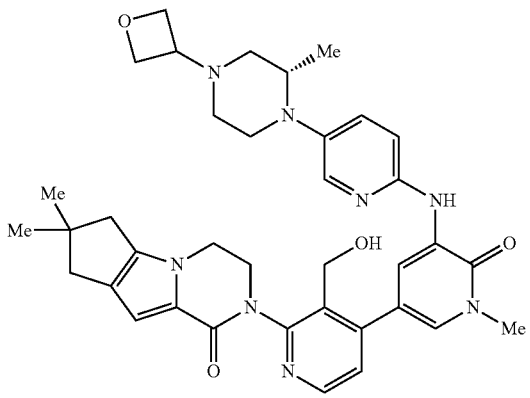 [SMILES: C[C@H]1CN(C2COC2)CCN1c1ccc(Nc2cc(-c3ccnc(N4CCn5c(cc6c5CC(C)(C)C6)C4=O)c3CO)cn(C)c2=O)nc1]

is known from U.S. publication US 2013/0116235 A1 as a BTK inhibitor that is useful for the treatment of a disease or disorder selected from immune disorders, cancer, cardiovascular disease, viral infection, inflammation, metabolism/endocrine function disorders and neurological disorders. US 2013/0116235 is incorporated herein by reference in its entirety. Alternative names for 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one can be used, but the shown chemical structure controls. The US 2013/0116235 publication a useful method for preparing 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4]bipyridinyl-2'-yl}-7,7-dimethyl-3,4,7,8-tetrahydro-2H,6H-cyclopenta[4,5]pyrrolo[1,2-a]pyrazin-1-one, but the method requires chromatographic purification and a low yield was achieved.

The US 2013/0116235 publication further discloses a useful five-step process for the preparation of tricyclic lactam compounds used as intermediates in the preparation of 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one and having the structure:

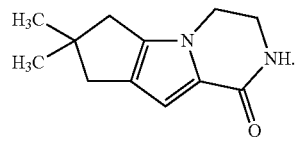

In the final step, the above-reference tricyclic lactam compound is generated by ring closure from the following compound:

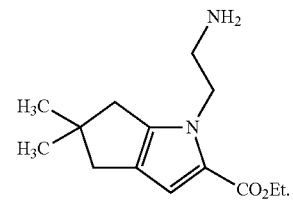

The multistep process requires two chromatographic purification steps and the overall yield based on the starting material was low.

A need therefore exists for improved method for preparing 2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one and intermediate compounds therefore.

BRIEF DESCRIPTION OF THE INVENTION

One aspect of the invention is directed to a method of preparing compound 200, stereoisomers thereof, geometric isomers thereof, tautomers thereof, and salts thereof:

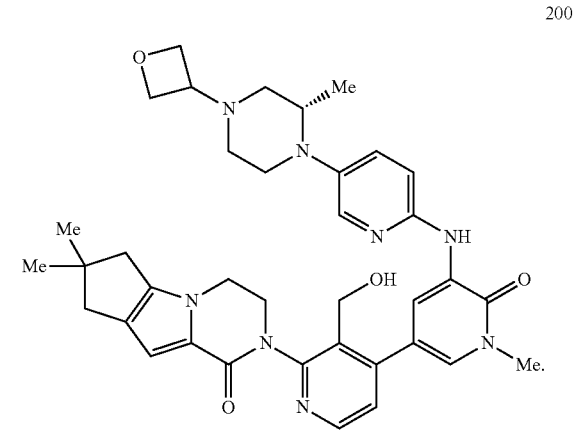 [SMILES: C[C@H]1CN(C2COC2)CCN1c1ccc(Nc2cc(-c3ccnc(N4CCn5c(cc6c5CC(C)(C)C6)C4=O)c3CO)cn(C)c2=O)nc1]

The method comprises forming a first reaction mixture comprising compound 170, compound 181, a palladium catalyst, a solvent system comprising water, and a base, wherein the ratio of solvent volume to compound 170 weight in the reaction mixture is less than 20:1 liters per kg, the equivalent ratio of compound 181 to compound 170 is greater than 1:1, and the equivalent ratio of the palladium catalyst to compound 170 is from about 0.005:1 to about 0.05:1.

The method further comprises reacting the first reaction mixture to form a first reaction product mixture comprising compound 190 according to the following scheme:

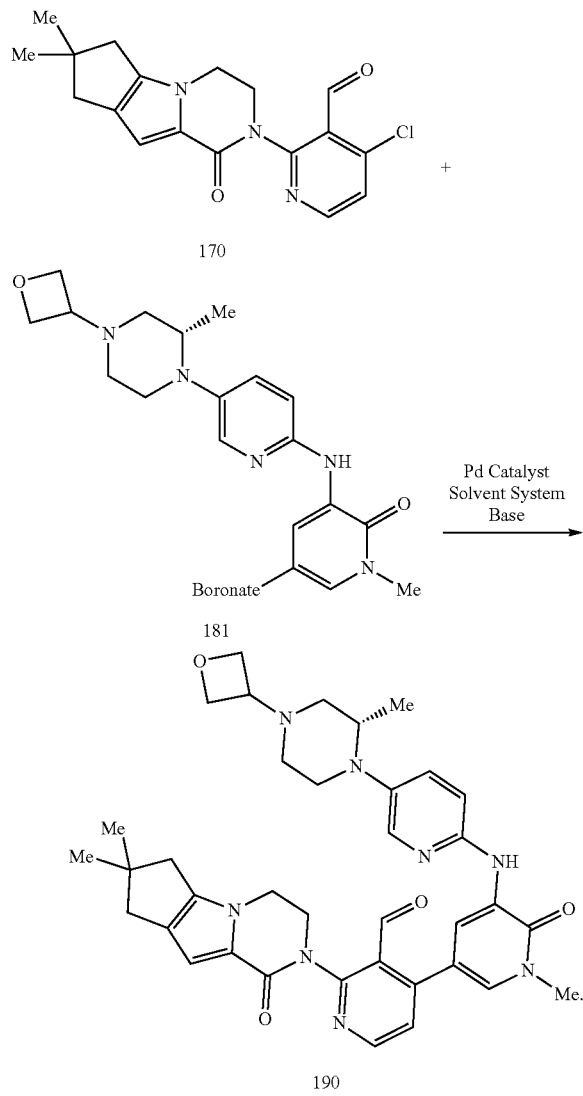

Compound 190 is isolated from the first reaction mixture.

A second reaction mixture is formed comprising compound 190, a reducing agent, a base and a solvent. The second reaction mixture is reacted to reduce the aldehyde moiety of compound 190 and form a second reaction product mixture comprising compound 200. Compound 200 is isolated from the reaction product mixture.

The yield of compound 190 is at least 50% based on compound 170, and the yield of compound 200 is at least 50% based on compound 190.

Another aspect of the invention is directed to a method for preparing a tricyclic lactam of formula 400, stereoisomers thereof, geometric isomers thereof, tautomers thereof, and salts thereof:

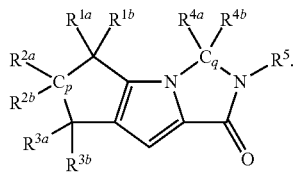

The method comprises forming a reaction mixture comprising an organic solvent, an organic base, and the compounds of formulas 300 and 310:

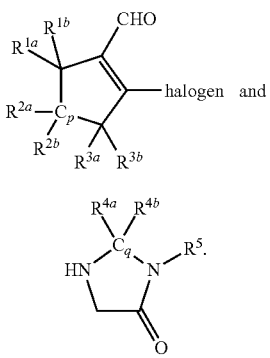

The reaction mixture is reacted to form a reaction product mixture comprising the tricyclic lactam of formula 400. $R^{1a}$, $R^{1b}$, $R^{2a}$, $R^{2b}$, $R^{3a}$, $R^{3b}$, $R^{4a}$ and $R^{4b}$ are independently selected from H, and $C_{1-6}$ alkyl. $R^5$ is selected from H, $C_{1-6}$ alkyl, cycloalkyl, aryl, substituted aryl, benzyl, substituted benzyl, heteroaryl, substituted heteroaryl. p is 1, 2, 3 or 4; and q is 1, 2, 3 or 4.

DETAILED DESCRIPTION OF THE INVENTION

Figure 1:
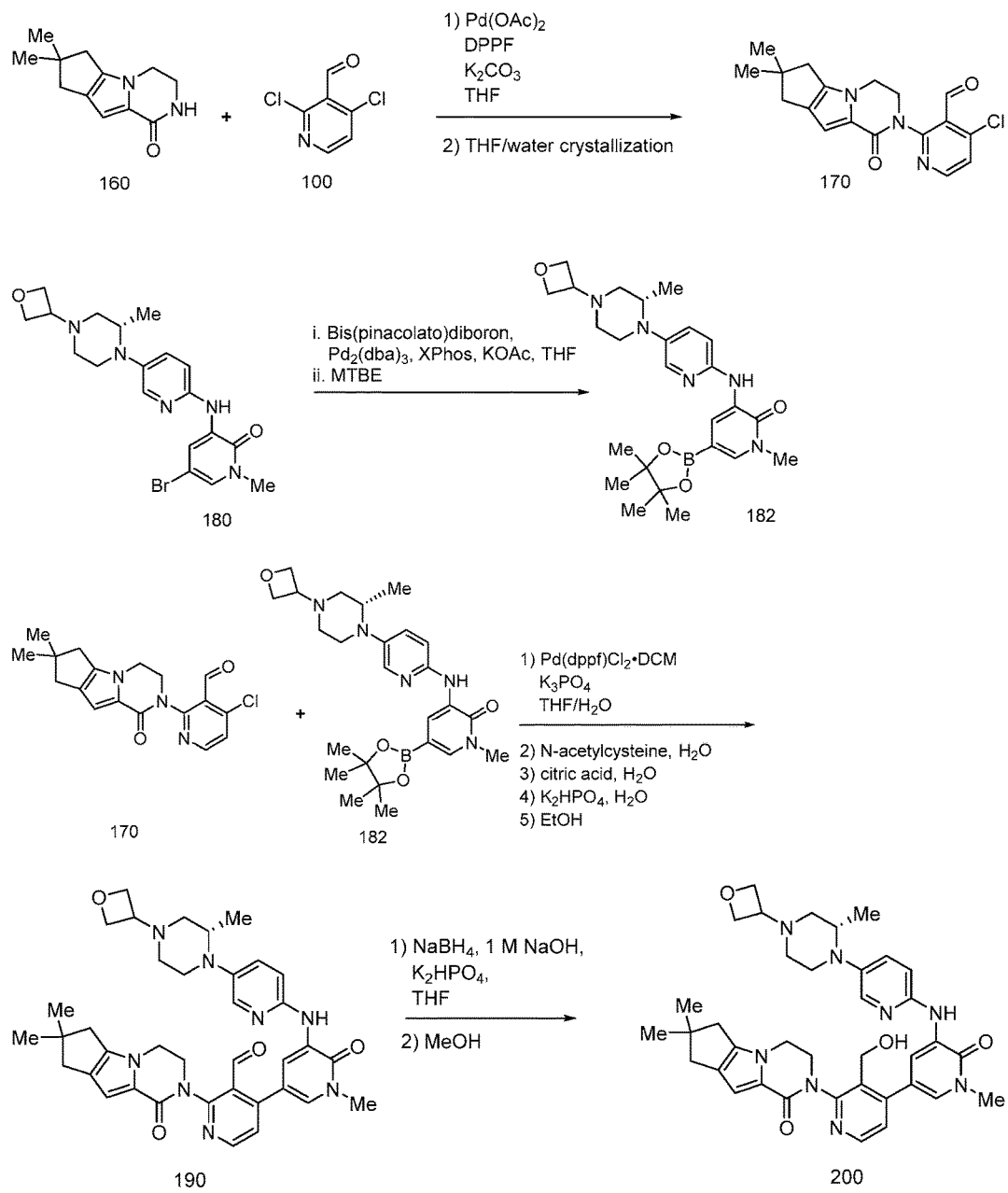
FIG. 1 shows a method for the preparation of compounds 170, 182, 190 and 200.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application. including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety.

Definitions

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

As used herein, "alkyl" refers to a monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

As used herein, "alkylene" refers to a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

As used herein, "cycloalkyl" refers to a monovalent saturated carbocyclic moiety consisting of mono- or bicyclic rings. Particular cycloalkyl are unsubstituted or substituted with alkyl. Cycloalkyl can optionally be substituted as defined herein. Examples of cycloalkyl moieties include, but are not limited to, cyclopropyl, cyclobutyl, cyclopentyl, cyclohexyl (i.e., "Cy"), cycloheptyl, and the like, including partially unsaturated (cycloalkenyl) derivatives thereof.

As used herein, "aryl" refers to a monovalent aromatic hydrocarbon radical of 6-20 carbon atoms ($C_6$-$C_{20}$). Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

As used herein, "arylalkyl" and "aralkyl", which may be used interchangeably, refer to a radical-$R_aR_b$ where $R_a$ is an alkylene group and $R_b$ is an aryl group as defined herein; e.g., phenylalkyls such as benzyl, phenylethyl, 3-(3-chlorophenyl)-2-methylpentyl, and the like are examples of arylalkyl.

As used herein, "heteroaryl" refers a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

As used herein, "alkoxy" refers to a moiety of the structure —OR, wherein R is an alkyl moiety as defined herein. Examples of alkoxy moieties include, but are not limited to, methoxy, ethoxy, isopropoxy, and the like.

As used herein, "haloalkyl" refers to an alkyl as defined herein in which one or more hydrogen atoms have been replaced with the same or a different halogen. Exemplary haloalkyls include —$CH_2Cl$, —$CH_2CF_3$, —$CH_2CCl_3$, —$CF_3$, $CHF_2$, and the like.

As used herein, "halogen" refers to chlorine, fluorine, bromine and iodine.

As used herein, "amino" refers to a moiety of the structure —NRR' wherein R and R' each hydrogen, "monoalkylamino" refers to such a structure where one of R and R' is hydrogen and the other of R and R' is alkyl, and "dialkylamino" refers to such a structure where each of R and R' is alkyl.

As used herein, "optionally substituted" as used herein refers to a moiety that may be unsubstituted or substituted with specific groups. Examples of substituents include, but are not limited to hydroxy, alkyl, alkoxy, halo, haloalkyl, oxo, amino, monoalkylamino, or dialkylamino.

As used herein, "chiral" refers to molecules which have the property of non-superimposability of the mirror image partner, while the term "achiral" refers to molecules which are superimposable on their mirror image partner.

As used herein, "stereoisomers" refers to compounds which have identical chemical constitution, but differ with regard to the arrangement of the atoms or groups in space.

As used herein, "diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

As used herein, "enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center (s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, while stereochemical determination awaits, such as x-ray crystallographic data.

As used herein, the terms "tautomer" and "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "salt" refers to both acid addition salts and base addition salts. "Acid addition salt" refers to salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as fomlic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnanlic acid, mandelic acid, embonic acid, phenylacetic acid, methanesulfonic acid mesylate, ethanesulfonic acid, p-toluenesulfonic acid, and salicyclic acid. "Base addition salt" refers to salts formed with an organic or inorganic base.

As used herein an "inorganic base" generally includes sodium, potassium, ammonium, calcium, magnesium, iron, zinc, copper, manganese, and aluminum salts. Non-limiting examples include phosphates such as dipotassium monohydrogen phosphate, potassium dihydrogen phosphate, tripotassium phosphate, disodium monohydrogen phosphate, sodium dihydrogen phosphate, trisodium phosphate, diammonium monohydrogen phosphate, ammonium dihydrogen phosphate and triammonium phosphate; acetates such as potassium acetate, sodium acetate and ammonium acetate; formates such as potassium formate and sodium formate; carbonates such as potassium carbonate, sodium carbonate, potassium hydrogen carbonate and sodium hydrogen carbonate; and alkali metal hydroxides such as lithium hydroxide, sodium hydroxide and potassium hydroxide. The inorganic bases may be used singly, or in combination of two or more kinds thereof.

As used herein, an "organic base" generally includes primary, secondary, and tertiary amines, substituted amines including naturally occurring substituted amines, cyclic amines and basic ion exchange resins, such as pyridine, isopropylamine, trimethylamine, diethylamine, triethylamine, triethanolamine, diisopropylamine, ethanolamine, 2-diethylaminoethanol, trimethylamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

As used herein, "non-polar solvent" refers to a solvent without significant partial charges on any atoms or a solvent where polar bonds are arranged in such a way that the effect of their partial charges cancel out. Non-limiting examples of non-polar solvents include pentane, hexane, heptane, cyclocpentane, cyclohexane, benzene, toluene, 1,4-dioxane, dichloromethane ("DCM"), methyl tert-butyl ether ("MTBE"), chloroform, carbon tetrachloride, and diethyl ether.

As used herein, an "aprotic solvent" refers to a solvent that does not donate hydrogen. Aprotic solvents typically have a labile hydrogen bound to an oxygen atom or to a nitrogen atom. As used herein, "polar aprotic solvent" refers to a solvent having high dielectric constants and high dipole movements and that lack an acidic hydrogen. Non-limiting examples of polar aprotic solvents include tetrahydrofuran ("THF"), methyl tetrahydrofuran ("Me-THF"), ethyl acetate ("EA"), acetone, dimethylformamide ("DMF"), acetonitrile ("ACN"), petroleum ether, N-methyl-2-pyrrolidone ("NMP"), and dimethyl sulfoxide.

As used herein, "polar protic solvent" refers to a solvent having a labile hydrogen bound to an oxygen atom or a nitrogen atom. Non-limiting examples of polar protic solvents include formic acid, n-butanol, i-propanol, n-propanol, ethanol, methanol, acetic acid and water.

As used herein, a "low boiling solvent" refers to a solvent having a boiling point of less than about 45° C. Non-limiting examples of low boiling solvents include dichloromethane, diethyl ether and pentane.

As used herein, a palladium catalyst refers to any palladium catalyst that affects the rate and conversion of a chemical substrate compound to a product compound as a commercially acceptable yield and conversion. In some aspects, the palladium catalyzed reactions described herein require a zero valent palladium species (Pd(0)). Exemplary catalytically active (Pd(0)) species may be applied directly (e.g. as commercial Pd(0) complexes such as Pd(PPh$_3$)$_4$, Pd(PCy$_3$)$_2$, Pd(PtBu$_3$)$_2$ or similar Pd(0) complexes), or may be formed from a palladium source in combination either with a phosphine ligand and/or a base (e.g., KOtBu, KOH, NaOAc, K$_3$PO$_4$, K$_2$CO$_3$, Hünig's base, NEt$_3$, NPr$_3$). In some aspects, the palladium source is selected from the following non-exclusive listing: [PdCl(X)]$_2$ (X=allyl, cinnamyl, crotyl, . . . ), [Pd(X)PR$_3$] (R=alkyl or aryl), [Pd(X)(Y)] (Y=cyclopentadienyl, p-cymyl,), Pd(dba)$_2$, Pd$_2$(dba)$_3$, Pd(OAc)$_2$, PdZ$_2$ (Z=Cl, Br, I), Pd$_2$Z$_2$(PR$_3$)$_2$, and Pd(TFA)$_2$. In some aspects, the catalytic palladium species is a palladium source selected from the following non-exclusive listing: [Pd(allyl)Cl]$_2$, Pd(MeCN)$_2$Cl$_2$, Pd(benzonitrile)$_2$Cl$_2$, Pd(dba)$_2$, Pd(OAc)$_2$, PdCl$_2$, PdBr$_2$, Pd(TFA)$_2$, Pd(MeCN)$_4$(BF$_4$)$_2$, Pd$_2$(dba)$_3$, Pd(PCy$_3$)$_2$Cl$_2$, Pd(acac)$_2$, and Pd(PPh$_3$)$_4$. In some such aspects, the palladium source is Pd$_2$(dba)$_3$ or Pd(OAc)$_2$. In some such aspects, the palladium source is Pd(PCy$_3$)$_2$. In some other aspects, the catalytic palladium species can be formed in situ from a palladium source, such as described above, and a ligand. Non-limiting examples of ligands include DPPF, DTPBF, BINAP, DPPE, DPPP, DCPE, RuPhos, SPhos, APhos (amphos), CPhos, XPhos, t-BuXPhos, Me$_4$t-BuXPhos, neopentyl(t-Bu)$_2$P, (t-Bu)$_2$PMe, (t-Bu)$_2$PPh, PCy$_3$, PPh$_3$, XantPhos, and N-XantPhos. In some aspects, the ligand is an aryl phosphate. In some aspects, the ligand is BINAP, XantPhos, or XPhos. In particular aspects, the ligand is Xantphos (4,5-bis(diphenylphosphino)-9,9-dimethylxanthene) or Xphos (2-dicyclohexylphosphino-2',4',6'-triisopropylbiphenyl) of the following structures:

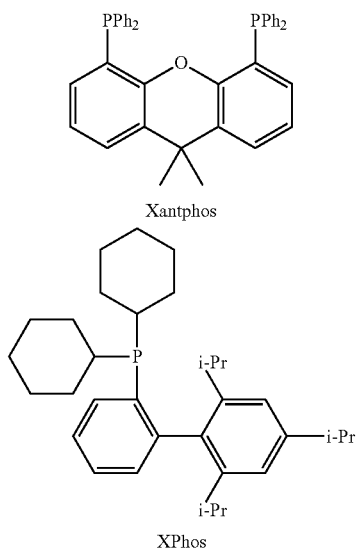

In some other aspects, the catalytic is a preformed catalyst. Non-limiting examples of preformed catalysts include Pd(dppf)Cl$_2$, Pd(dppe)Cl$_2$, Pd(PCy$_3$)$_2$Cl$_2$, bis(triethylphosphine)palladium(II) chloride, Pd(t-Bu$_3$P)$_2$Cl$_2$, Pd[P(o-tol)$_3$]$_2$Cl$_2$, Pd(PPh$_3$)$_2$Cl$_2$, Pd(OAc)$_2$(PPh$_3$)$_2$, and Pd(CH$_3$CN)$_2$Cl$_2$. In some such aspects, the preformed catalyst is Pd(dppf)Cl$_2$. In some further aspects, the catalyst source or preformed catalyst may complex with a solvent such as dichloromethane, chloroform or acetonitrile. Non-limiting examples of such complexes include Pd(dppf)Cl$_2$.DCM, Pd$_2$(dba)$_3$.CHCl$_3$ and Pd(PPh$_3$)$_2$Cl$_2$.ACN.

As used herein, a borylation reagent refers to any borylation reagent capable of cross-coupling with an aryl halide to form an aryl boronate. Examples of borylation reagents include, without limitation, tetrahydroxyboron, catecholborane, 4,4,5,5-tetramethyl-1,3,2-dioxaborolane, 4,6,6-trimethyl-1,3,2-dioxaborinane, diisopropylamine borane, bis(neopentyl glycolato)diboron, bis(catecholato)diboron, bis(hexylene glycolato)diboron, bis(pinacolato)diboron, 4-(4,4,5,5-tetramethyl-1,3,2-dioxaborolan-2-yl)-5-(trifluoromethyl)-1-(triisopropylsilyl)-1H-pyrrolo[2,3-b]pyridine, bis(2,4-dimethylpentane-2,4-glycolato)diboron, phenyl boronic acid, diisopropoxy methyl borane, and methyl boronic acid.

As used herein "reducing agent" refers to a compound that donates an electron. Non-limiting examples of reducing agents include sodium borohydride, potassium borohydride, sodium bis(2-methoxyethoxy)aluminum hydride, sodium bisulfite, sodium hydrogensulfite, sodium hydrosulfite, sodium tetrahydroborate, potassium tetrahydroborate, sodium triacetoxyborohydride, trichlorosilane, triphenylphosphite, triethylsilane, trimethylphosphine, triphenylphosphine, diborane, diethoxymethylsilane, diisobutylaluminum hydride, diisopropylaminoborane, lithium aluminum hydride, and lithium triethylborohydride.

As used herein "protecting group" refers to group used for protection of remote functionality (e.g., primary or secondary amine) of intermediates. The need for such protection will vary depending on the nature of the remote functionality and the conditions of the preparation methods. Suitable amino-protecting groups include acetyl trifluoroacetyl, t-butoxycarbonyl (BOC), benzyloxycarbonyl (Cbz) and 9-fluorenylmethyleneoxycarbonyl (Fmoc). For a general description of protecting groups and their use, see T. W. Greene, *Protective Groups in Organic Synthesis*, John Wiley & Sons, New York, 1991.

As used herein "equivalent ratio" refers to a mole ratio.

As used herein, "predominant" and "predominantly" refer to greater than 50%, at least 75%, at least 90%, at least 95%, at least 99% or at least 99.9% on any of a weight, volume, molar, v/w %, w/w %, w/v % or v/v % basis.

Compounds of the present disclosure may be separated, isolated and purified by the following non-exclusive methods and combinations thereof. In some methods, the compounds may be isolated and/or purified by forming a suspended solid thereof in a liquid carrier phase by methods such as salt formation, crystallization or precipitation (such as by solvent concentration, solvent exchange, pH adjustment and/or temperature adjustment). In some other purification methods, solutions of the compounds may be contacted with a source of carbon (such as charcoal), diatomaceous earth and/or a chromatography resin, to remove impurities. Two phase solid-liquid mixtures comprising (i) solid compounds of the present disclosure and a liquid carrier phase or (ii) compounds of the present disclosure in solution in a liquid carrier phase in combination with suspended solids (e.g., charcoal, diatomaceous earth or resin) may be separated by filtration or centrifugation. Isolated solids may be optionally washed to remove additional impurities (in the case of solid product compound) or soluble product (e.g., in the case of a product solution). In some methods, the compounds of the present disclosure may be isolated and/or purified by liquid-liquid extraction and phase separation. Phase separation may be suitably done gravimetrically or by liquid-liquid centrifugation. In some methods, the compounds of the disclosure may be isolated and/or purified by chromatographic methods such as ion exchange chromatography or affinity chromatography. In one such method, the compounds may be isolated and/or purified by preparative HPLC. In some methods, the compounds may be isolated and/or purified by distillation (e.g., fractional distillation). In some other methods, compounds of the present disclosure may be isolated and/or purified by ultrafiltration. In any of the various aspects, solid compounds of the present disclosure may optionally be dried, such as using vacuum dryers or fluidized bed dryers. Any of the separation, isolation and purification methods may be used in combination. For instance, and without limitation, compounds of the present disclosure may be isolated and purified by extraction, solvent exchange, crystallization, and drying. In some other non-limiting aspects, compounds of the present disclosure may be precipitated or crystallized, isolated, dissolved, precipitated or crystallized, isolated, and dried, where two or more dissolution and crystallization iterations are possible. In some other non-limiting aspects, the compounds of the present disclosure may be isolated by solvent exchange and fractional distillation.

Preparation of Compound 200

In some aspects of the present invention, compound 200, stereoisomers thereof, geometric isomers thereof, tautomers thereof, and salts thereof, may be prepared from compounds 170 and 181 according to the following two step reaction scheme:

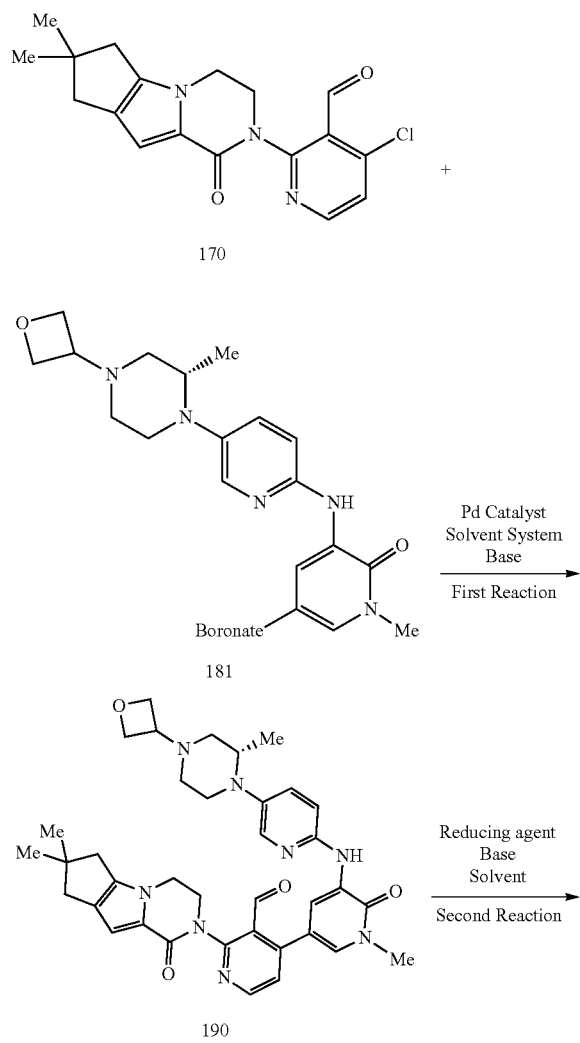

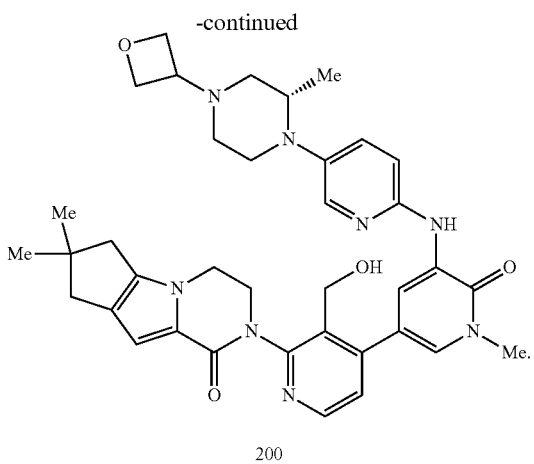

In a first step, compound 190 comprises is prepared from a first reaction mixture comprising compound 170, compound 181, a palladium catalyst, a solvent system comprising water, and a base, and reacting the first reaction mixture to form a first reaction product mixture comprising compound 190. In some aspects, compound 190 is isolated from the first reaction product mixture. In a second step, compound 200 is prepared from a second reaction mixture comprising compound 190, a reducing agent, a base and a solvent, and reacting the second reaction mixture to reduce the aldehyde moiety of compound 190 and form a second reaction product mixture comprising compound 200. Compound 200 is optionally isolated from the second reaction product mixture.

In the first reaction mixture, the equivalent ratio of compound 181 to compound 170 is greater than 1:1. The palladium catalyst in the first reaction mixture is a palladium catalyst as described elsewhere herein. In some aspects, the palladium catalyst is Pd(dppf)Cl$_2$.DCM. In some aspects, the palladium catalyst is Pd(dppf)Cl$_2$. The equivalent ratio of the palladium catalyst to compound 170 is about 0.005:1, about 0.01:1, about 0.02:1, about 0.03:1, about 0.04:1, about 0.05:1, about 0.06:1, about 0.07:1 or about 0.08:1, and ranges thereof, such as from about 0.005:1 to about 0.08:1, from about 0.005:1 to about 0.05:1, or from about 0.005:1 to about 0.02:1. In some aspects, the first reaction mixture base is an inorganic base. In some particular aspects, the base is $K_3PO_4$ or $K_2HPO_4$. In some aspects, the first reaction mixture solvent system comprises water and a polar aprotic solvent. The volume ratio of water to polar aprotic solvent is about 0.05:1, about 0.1:1, about 0.2:1, about 0.3:1, about 0.4:1, about 0.5:1, about 0.6:1, about 0.7:1, about 0.8:1 or about 0.9:1, and ranges thereof, such as from about 0.05:1 to about 0.9:1 from about 0.05:1 to about 0.5:1, or from about 0.1:1 to about 0.4:1. In some particular aspects, the solvent system comprises water and THF. In some aspects, the ratio of the solvent system volume in the first reaction mixture to compound 170 weight may be less than about 20:1 L/kg, about 5:1 L/kg, about 10:1 L/kg, about 15:1 L/kg, about 20:1 L/kg, about 25:1 L/kg, or about 30:1 L/kg, and ranges thereof, such as from about 5:1 to about 30:1 L/kg or from about 5:1 to about 20:1 L/kg.

The reaction temperature for forming compound 190 is suitably about 40° C., about 45° C., about 50° C., about 55° C., or about 60° C. The reaction may be deemed complete when the area % concentration by HPLC of compound 170 is less than 2, less than 1, less than 0.5 or less than 0.1. The reaction time to completion may be 2 hours, 4 hours, 8 hours, 12 hours, 16 hours, 20 hours or 24 hours.

In some aspects of the invention, compound 190 may be purified. In some such aspects, the temperature of the first reaction product mixture may be adjusted from about 10° C. to about 35° C. or from about 15° C. to about 30° C. and combined with agitation with aqueous N-acetyl-L-cysteine having a N-acetyl-L-cysteine concentration of about 3 wt. %, about 6 wt. % or about 9 wt. %, and ranges thereof, such as from about 3 wt. % to about 9 wt. %. The equivalent ratio of N-acetyl-L-cysteine to compound 190 may be from about 0.1:1, about 0.3:1 or about 0.5:1, and ranges thereof, such as from about 0.01:1 to about 0.5:1. The ratio of aqueous N-acetyl-L-cysteine volume to compound 190 weight may be about 1 L/kg, about 2 L/kg or about 3 L/kg, and ranges thereof, such as from about 1 L/kg to about 3 l/kg. An aqueous layer is separated and an organic layer comprising compound 190 is collected. In some aspects, the upper layer may be optionally combined with agitation with citric acid solution having a citric acid concentration of about 3 wt. %, about 5 wt. % or about 7 wt. %, and ranges thereof, such as from about 3 wt. % to about 7 wt. %, wherein the ratio of the citric acid solution volume to compound 190 weight may be about 0.5 L/kg, about 1 l/kg, about 1.5 L/kg or about 2 L/kg, and ranges thereof, such as from about 0.5 L/kg to about 2 L/kg. It is believed that the dimer impurity predominantly partitions to the citric acid wash. The organic layer may be further optionally combined with a salt solution (e.g. NaCl) having a salt content of from about 15 wt. % to about 35 wt. %, wherein the ratio of the salt solution volume to compound 190 weight may be about 0.5 L/kg, about 1 l/kg, or about 1.5 L/kg, and ranges thereof, such as from about 0.5 L/kg to about 1.5 L/kg. An aqueous layer is separated and an organic layer comprising compound 190 is collected. The organic layer may optionally be washed one or more additional times with the salt solution at a ratio of the salt solution volume to compound 190 weight of from about 0.5 L/kg to about 4 L/kg. Optionally, a base, such as aqueous 60 wt. % $K_2HPO_4$ in a volume to compound 190 weight ratio of from about 0.5 L/kg to about 1.5 L/kg, may be included in the final salt wash. After the final salt wash, an aqueous layer is separated and an organic layer comprising compound 190 is collected.

Compound 190 may optionally be isolated from the first reaction product mixture or from the organic layer comprising compound 190 from the purification step by combining the first reaction product mixture or the upper layer comprising compound 190 with a solvent having a boiling point of less than about 80° C. and having a polarity similar to the solvent in the first reaction product mixture or the organic layer comprising compound 190. In some aspects, the solvent is THF. The volume may be reduced by vacuum distillation, and the reduced volume comprising compound 190 may be diluted with the solvent (e.g., THF) to a total solvent volume of from about 8 to about 12 L solvent per kg of compound 190 to produce a diluted solution of compound 190. The diluted admixture may optionally be combined and treated with activated carbon followed by filtration to generate a filtered solution of compound 190. The volume of the solution of purified compound 190 may be reduced by distillation to a reduced volume of from about 3 to about 7 L solvent per kg of compound 190. The THF dilution and distillation step may be repeated one or more times. From about 3 to about 7 L of ethanol per kg of compound 190 may be combined with the reduced volume and may thereafter be distilled to a reduced volume of from about 3 to about 7 L solvent per kg of compound 190. The ethanol addition and distillation step may be repeated one or more times. Ethanol may be added to the reduced volume to a concentration of from about 8 to about 12 L solvent per kg of compound 190 to produce a diluted mixture of compound 190. The diluted mixture of compound 190 may be cooled, such as to less than 25° C., to crystallize purified compound 190 from the cooled and diluted mixture. The purified compound 190 crystals may be collected, such as by filtration or centrifugation, and dried to yield purified dry compound 190 crystals.

The yield of compound 190 based on compound 170 is at least 50%, at least 60%, at least 70%, at least 80% or at least 90%, and the purity of compound 190 is at least 99 area % by HPLC or at least 99.5 area % by HPLC.

In the second reaction mixture, in some aspects, the solvent is selected from $C_{1-4}$ alcohols, ethers and cyclic ethers. In some particular aspects, the solvent in the second reaction mixture is selected from THF, methyl tert-butyl ether, and 2-Me-THF. The ratio of solvent volume to compound 190 weight may be about 2:1 L/kg, about 3:1 L/kg, about 4:1 L/kg, about 5:1 L/kg, about 6:1 L/kg, about 7:1 L/kg, about 8:1 L/kg, about 9:1 L kg, about 10:1 L/kg, and ranges thereof, such as from about 2:1 to about 10:1 L/kg, or from about 4:1 to about 8:1 L/kg. In some aspects, the base in the second reaction mixture is an inorganic base, such as an alkali hydroxide. In one such aspect, the base is sodium hydroxide. The equivalent ratio of base to compound 190 is about 0.1:1, about 0.2:1, about 0.3:1, about 0.4:1, about 0.5:1, about 0.6:1, about 0.7:1, about 0.8:1, or about 0.9:1, and ranges thereof, such as from about 0.1:1 to about 0.9:1 or from about 0.3:1 to about 0.7:1. In any of the various aspects, the reducing agent is as described elsewhere herein. In some particular aspects, the reducing agent is sodium borohydride. The equivalent ratio of the reducing agent to compound 190 is about 0.1:1, about 0.2:1, about 0.3:1, about 0.4:1, about 0.5:1, about 0.6:1, about 0.7:1, about 0.8:1, or about 0.9:1, and ranges thereof, such as from about 0.1:1 to about 0.9:1 or from about 0.2:1 to about 0.8:1. In any of the various aspects, the boronate is generated from a borylation agent as described elsewhere herein. In one such aspect, the boronate is 4,4,5,5-tetramethyl-1,3,2-dioxaborolane of the structure:

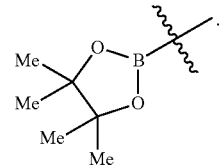

The reaction temperature for forming compound 200 is suitably about 10° C., about 15° C., about 20° C., about 25° C., or about 30° C. The reaction may be deemed complete when the area % concentration by HPLC of compound 200 is less than 2, less than 1, less than 0.5 or less than 0.1. In some aspects, the reaction time to completion may be 0.5 hours, 1 hour, 2 hours, 4 hours, 6 hours, or more. The yield of compound 200 is at least 60%, at least 70%, at least 80%, or at least 85%, and the purity of compound 200 is at least 99 area % or at least 99.5 area % by HPLC.

Compound 200 may be isolated from the second reaction product mixture. In some aspects, compound 200 may be isolated by admixing the second reaction product mixture with monopotassium phosphate solution in a volume ratio to compound 200 weight of from about 0.5 L to about 2 L of about 10 percent by weight to about 25 percent by weight aqueous monopotassium phosphate solution per kg of compound 200. An aqueous layer is separated and an organic layer comprising compound 200 in solution is collected. The organic layer comprising compound 200 may be filtered. The filtrate may be distilled to a volume of from about 2 to about 4 L/kg of compound 200. A suitable solvent, such as methanol, may be added to the distilled filtrate to a total volume of from about 6 to about 8 L/kg of compound 200. In some aspects, from about 0.2 to about 0.8 percent by weight compound 200 seed crystals may be added to form a mixture. The mixture is distilled to reduce the volume by at least 1 L/kg of compound 200. The distilled mixture of compound 200 may be cooled, such as to less than 20° C., to crystallize compound 200 from the cooled mixture. Compound 200 crystals may be collected and dried.

In some aspects, the purified compound 200 crystals may be recrystallized in a purification step. In some such aspects, compound 200 is combined with ethanol at a ratio of ethanol volume to compound 200 weight of from about 4 L/kg to about 10 L/kg or from about 6 L/kg to about 8 L/kg and with toluene at a ratio of toluene volume to compound 200 weight of from about 1 L/kg to about 5 L/kg or from about 1.5 L/kg to about 3.5 L/kg and with agitation. The mixture may be heated, such as to from about 65 to about 85° C., with agitation and held until a solution is obtained. The solution may be then cooled, such as to from about 60 to about 70° C., and combined with seed crystals, such as from about 0.5 wt. % to about 3 wt. % or from about 0.5 wt. % to about 1.5 wt. % compound 200 seed crystals, to form a slurry. Ethanol may be combined with the slurry at a ratio of ethanol volume to compound 200 weight of from about 5 L/kg to about 25 L/kg or from about 10 L/kg to about 20 L/kg. The slurry may be cooled, such as to from about −5 to about 15° C., and held for at least 2 hours, at least 4 hours, or at least 8 hours to crystallize compound 200. The crystals may be collected, such as by filtration or centrifugation, and washed with ethanol. The washed crystals may be dried under vacuum with a $N_2$ purge at from about 40 to about 60° C. for at least 4 hours, at least 8 hours, at least 12 hours, or at least 20 hours to produce purified compound 200.

In some aspects of the present invention, compound 170 may be prepared from compounds 100 and 160 according to the following reaction scheme:

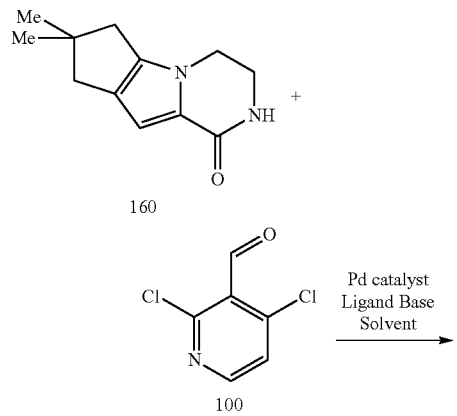

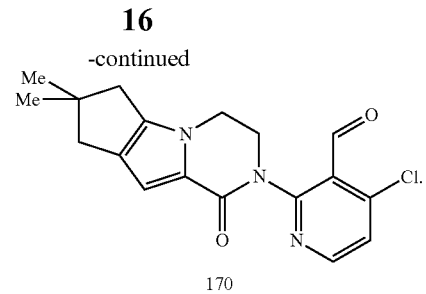

The method for preparing compound 170 comprises forming a reaction mixture comprising compound 160, a stoichiometric excess of compound 100, a palladium catalyst and a catalyst ligand, a base and a polar aprotic solvent. The reaction mixture is reacted to form a reaction product mixture comprising compound 170. Compound 170 may optionally be isolated from the reaction mixture.

The equivalent ratio of compound 100 to compound 160 in the reaction mixture is greater than 1:1, about 1.05:1, about 1.1:1, about 1.2:1, about 1.3:1, about 1.4:1, about 1.5:1, about 1.6:1 or about 1.7:1, and ranges thereof, such as between 1:1 and 1.7:1, from about 1.05:1 to about 1.5:1 or from about 1.05:1 to about 1.2:1. In some aspects, compound 160 is prepared as disclosed elsewhere herein. The palladium catalyst and catalyst ligand are as described elsewhere herein. In some aspects, the catalyst is $Pd(OAc)_2$ and the ligand is DPPF. The polar aprotic solvent is as described elsewhere herein. In some aspects, the solvent is THF. The ratio of solvent volume to compound 160 weight in the reaction mixture may be about 2:1 L/kg, about 5:1 v L/kg, about 10:1 L/kg, about 15:1 L/kg, about 20:1 L/kg, about 25:1 L/kg, or about 30:1 L/kg, and ranges thereof, such as from about 2:1 to about 30:1 L/kg, from about 5:1 to about 20:1 L/kg, or from about 5:1 to about 15:1 L/kg. In some aspects, the concentration of compound 160 in the reaction mixture is about 0.1 mol/L, about 0.2 mol/L, about 0.3 mol/L, about 0.4 mol/L, about 0.5 mol/L, about 0.75 mol/L, about 1 mol/L, and ranges thereof, such as from about 0.1 mol/L to about 1 mol/L, or from about 0.2 to about 0.5 mol/L. The equivalent ratio of catalyst to compound 160 is from about 0.01:1, about 0.02:1 about 0.03:1, about 0.04:1, or about 0.05:1, and ranges thereof, such as from about 0.01:1 to about 0.05:1 or from about 0.01:1 to about 0.03:1. The equivalent ratio of the ligand to the catalyst is from about 1.2:1, about 1.5:1, about 2:1, about 2.5:1 or about 3:1, and ranges thereof, such as from about 1.2:1 to about 3:1 or from about 1.5:1 to about 2.5:1. In some aspects, the base is an inorganic base as described elsewhere herein. In some particular aspects, the base is potassium carbonate. The equivalent ratio of the base to compound 160 is suitably greater than 1:1, about 1.2:1, about 1.5:1 about 1.8:1 or about 2:1, and ranges thereof, such as between 1:1 and 2:1, or from about 1.2:1 to about 1.8:1.

The reaction may be run under a $N_2$ blanket and/or with $N_2$ purging. The reaction may be done at reflux temperature, typically between about 60° C. and about 80° C. The reaction may be deemed complete when the area % concentration by HPLC of compound 160 is less than 3, less than 2, less than 1 or less than 0.5. In some aspects, the reaction time to completion may be 2 hours, 6 hours, 10 hours, 14 hours, 18 hours, 22 hours, or more.

Compound 170 may be isolated from the reaction product mixture. In some aspects, water may be combined with the reaction product mixture at a ratio of water volume to compound 160 weight of about 2:1, about 5:1, about 10:1, about 15:1 or about 20:1, and ranges thereof, such as from about 2:1 to about 20:1 or from about 2:1 to about 10:1. The temperature may be reduced to induce crystallization of compound 170 and form a suspension of solid compound 170. The temperature may be from about 5° C. to about 30° C., or from about 15° C. to about 25° C. The temperature may be maintained for at least 1 hour, at least 2 hours or at least 3 hours. Solid compound 170 may be isolated from the reaction mixture, such as by filtration or centrifugation. Isolated compound 170 may optionally be dried. In some drying aspects, drying is done under a partial vacuum with a $N_2$ purge at a temperature of from about 15° C. to about 40° C., or from about 15° C. to about 30° C. for at least 2 hours, at least 3 hours or at least 4 hours.

The yield of compound 170 based on compound 160 is at least 80%, at least 85% or at least 90%. The purity of compound 170 is at least 95 area %, at least 98 area % or at least 99 area % by HPLC.

In some aspects of the present invention, compound 100 may be prepared from compound 95 according to the following two step reaction scheme:

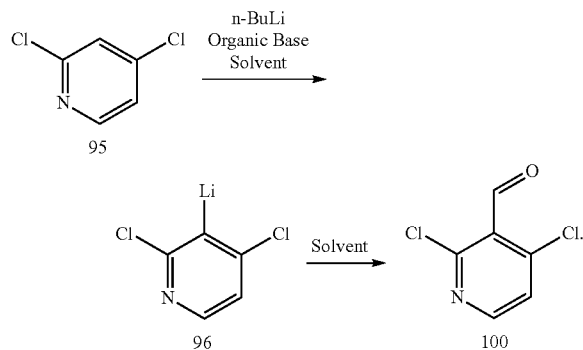

In the first step, a first reaction mixture comprising compound 95, n-butyl lithium, an organic base, and a polar aprotic solvent, is formed and reacted to form a first reaction product mixture comprising compound 96. In the second step, a second reaction product mixture is formed by admixing the first reaction product mixture with a polar aprotic solvent. The second reaction mixture is reacted to form a second reaction product mixture comprising compound 100. Compound 100 may optionally be isolated from the second reaction product mixture.

In some aspects, the first reaction mixture comprises a polar aprotic solvent as described elsewhere herein. In some aspects, the polar aprotic solvent is THF. The solvent volume to compound 95 weight in the first reaction mixture is about 2:1 L/kg, about 3:1 L/kg, about 4:1 L/kg, about 5:1 L/kg, about 6:1 L/kg, about 7:1 L/kg, about 8:1 L/kg, about 9:1 L/kg, or about 10:1 L/kg, and ranges thereof, such as from about 2:1 to about 10:1 L/kg, from about 3:1 to about 10:1 L/kg, or from about 4:1 to about 6:1 L/kg. The mole ratio of n-butyl lithium to compound 95 is greater than 1:1, about 1.2:1, about 1.4:1, about 1.6:1, about 1.8:1, about 2:1, and ranges thereof, such as between 1:1 and 2:1, or from about 1.2:1 to about 1.6:1. The n-butyl lithium may be a solution of n-butyl lithium in hexane, such as a 2.5 molar solution. The organic base is as defined elsewhere herein. In some aspects, the organic base is diisopropylamine. The mole ratio of the organic base to compound 95 is about 1.1:1, about 1.2:1 about 1.4:1, about 1.6:1 about 1.8:1 or about 2:1, and ranges thereof, such as from about 1.1:1 to about 2:1, from about 1.2:1 to about 2:1, or from about 1.4:1 to about 1.8:1. The reaction temperature for generation of the first reaction product mixture is greater than −35° C., about −30° C., about −25° C., about −20° C., about −15° C., or about −10° C., and ranges thereof, such as between −35° C. and about −10° C., or from about −30° C. to about −15° C.

In some aspects, the second reaction mixture comprises additional polar aprotic solvent. In some aspects, the polar aprotic solvent is DMF. In such aspects, the volume of the additional polar aprotic solvent to compound 95 weight in the second reaction mixture is about 2:1 L/kg, about 3:1 L/kg, about 4:1 L/kg, about 5:1 L/kg, about 6:1 L/kg, about 7:1 L/kg, about 8:1 L/kg, about 9:1 L/kg, or about 10:1 L/kg, and ranges thereof, such as from about 2:1 to about 10:1 L/kg, or from about 3:1 to about 7:1 L/kg. In such aspects, the mole ratio of the additional polar aprotic solvent to compound 95 is from about 1.1:1 to about 2:1, or from about 1.3:1 to about 1.5:1. The reaction temperature for generation of the first reaction product mixture is greater than −50° C., about −45° C., about −40° C., about −35° C., about −30° C., about −25° C., about −20° C., about −15° C., or about −10° C., and ranges thereof, such as between −50° C. and −10° C., or between −30° C. and −15° C. The second reaction product mixture may be quenched with an aqueous mineral acid solution, such as a 10 wt. % to 25 wt. % solution of HCl wherein the equivalent ratio of acid to compound 100 may be from about 2:1 to about 8:1, or from about 4:1 to about 6:1.

Compound 100 may be prepared in either a batch or a continuous scheme. In a continuous scheme, solution A (n-BuLi in hexane as described elsewhere herein), and solution B (diisopropylamine in THF) may be transferred through a mixer and into a first reactor to form a first reaction product mixture. In some aspects, the residence time in the first reactor is suitably from about 10 to about 60 seconds or from about 20 to about 30 seconds and the reaction temperature is greater than −35° C. as described elsewhere herein. The first reaction product mixture and solution C (compound 95 in solvent as described elsewhere herein) may be transferred through a mixer and into a second reactor to form a second reaction product mixture comprising a solution of lithiated 2,4-dichloropyridine. In some aspects, the residence time in the second reactor is suitably from about 10 to about 60 seconds or from about 20 to about 30 seconds and the reaction temperature is greater than −35° C. as described elsewhere herein. The second reaction product mixture and solution D (DMF as described elsewhere herein) may be transferred through a mixer and into a third tubular reactor to form a third reaction product mixture comprising compound 100. In some aspects, the residence time in the third reactor is suitably from about 10 to about 60 seconds or form about 20 to about 30 seconds and the reaction temperature is greater than −35° C. as described elsewhere herein. The third reaction product mixture may be collected in a quench reactor at from about 0 to about 20° C. and combined with an aqueous quench solution (such as an HCl quench solution as described elsewhere herein). Suitable continuous reactors include, for instance, tubular reactors and continuous stirred tank reactors.

Compound 100 may be optionally isolated from the second reaction product mixture.

In one such isolation aspect, compound 100 may be extracted from a quenched second reaction product mixture comprising water at a temperature of from about 5° C. to about 30° C. by admixing the quenched second reaction product mixture with ethyl acetate, and separating an ethyl acetate phase comprising compound 100. The ratio of ethyl acetate volume to compound 95 weight may be about 1:1 L/kg, about 2:1 L/kg, about 3:1 L/kg, about 4:1 L/kg, or about 5:1 L/kg. One or more extractions may be done. The collected ethyl acetate extractions may be washed with a brine solution and dried over sodium sulfate. The ethyl acetate extractions may be concentrated under reduced pressure, such as to a volume to compound 95 weight ratio of from about 2:1 to about 4:1 L/kg. Petroleum ether at a w/w % ratio to compound 95 of from about 3:1 to about 12:1 or from about 5:1 to about 9:1 may be added to the ethyl acetate and agitated at less than 25° C. for a time sufficient to form a slurry containing solid compound 100. Solid compound 100 may isolated, such as by filtration or centrifugation, and dried under vacuum at from about 30° C. to about 50° C. to yield solid compound 100.

In another such isolation aspect, the quenched reaction product mixture comprising compound 100 may be heated to from about 10 to about 35° C. followed by phase separation. The organic and aqueous layers may be collected and the aqueous layer may be mixed and extracted with a non-polar solvent, followed by phase separation. The w/w ratio of the non-polar solvent to compound 100 is suitably from about 3:1 to about 12:1 or from about 6:1 to about 10:1. One or more extraction steps may be done. In some aspects the non-polar solvent is toluene. The organic layers may be combined, and optionally washed with brine and water. The organic layers may be concentrated and cooled to from about 30 to about 50° C. A linear non-polar solvent (e.g., heptane) may be added while maintaining the temperature to from about 30 to about 50° C. The w/w ratio of the linear non-polar solvent to compound 100 is suitably from about 5:1 to about 20:1 or from about 10:1 to about 14:1. A resulting slurry comprising solid compound 100 may be cooled and aged for from about 1 to about 3 hours at from about −20 to about 0° C. Compound 100 may isolated, such as by filtration or centrifugation, and dried under partial or full vacuum. In some aspects, the drying temperature may be less than 40° C.

In yet another such isolation aspect, the quenched reaction product mixture comprising compound 100 may be heated to from about 10 to about 35° C. followed by phase separation. The organic and aqueous layers may be collected and the aqueous layer may be mixed and extracted with a non-polar solvent (e.g., toluene), followed by phase separation. The w/w ratio of the non-polar solvent to compound 100 is suitably from about 3:1 to about 12:1 or from about 6:1 to about 10:1. One or more extraction steps may be done. In some aspects the non-polar solvent is toluene. The combined organic layers are then washed with brine, followed by an aqueous solution of sodium bicarbonate, followed by a final wash with water. In some embodiments, the wash with brine is done with about 2-3 equivalent volumes of brine. In some embodiments, the aqueous sodium bicarbonate solution has a concentration of about 5% NaHCO$_3$ in water. In some embodiments, the wash with brine is done with about 5 equivalent volumes of 4.8% NaHCO$_3$. In some embodiments, the final wash with water is done with about 1 equivalent volume of water. The organic layers may be concentrated and cooled to from about 30 to about 50° C. A linear non-polar solvent (e.g., heptane) may be added while maintaining the temperature to from about 30 to about 50° C. The w/w ratio of the linear non-polar solvent to compound 100 is suitably from about 5:1 to about 20:1 or from about 10:1 to about 14:1. A resulting slurry comprising solid compound 100 may be cooled and aged for from about 1 to about 3 hours at from about −20 to about 0° C. Compound 100 may isolated, such as by filtration or centrifugation, and dried under partial or full vacuum. In some aspects, the drying temperature may be less than 40° C.

The yield of compound 100 is at least 70%, at least 80%, at least 85% or at least 87%. The purity of compound 100 is at least 90 area %, at least 95 area %, or at least 99.5 area % by HPLC.

In some aspects of the present invention, compound 181 may be prepared from compound 180 according to the following reaction scheme:

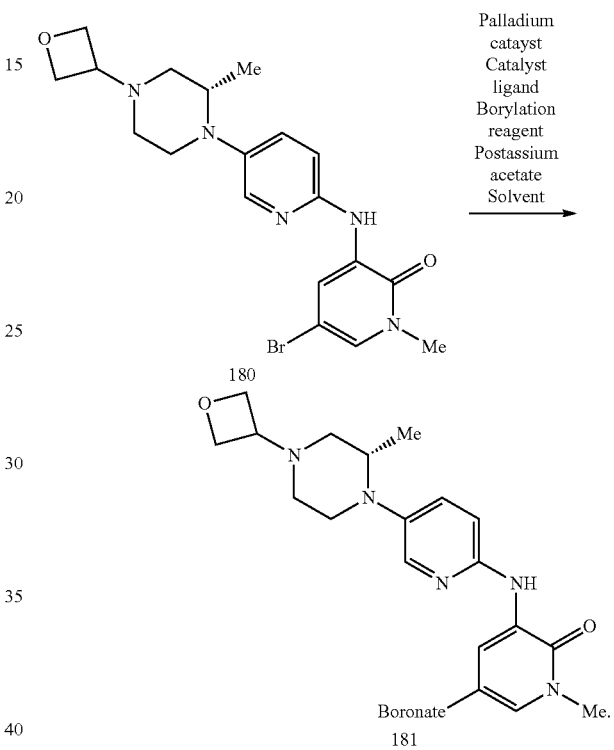

The method for preparing compound 181 comprises forming a reaction mixture comprising compound 180, a palladium catalyst, a catalyst ligand, a borylation reagent, an alkali metal acetate salt, and a polar aprotic solvent. The reaction mixture is reacted to form a reaction product mixture comprising compound 181. Compound 181 is optionally isolated from the reaction product mixture.

The palladium catalyst and the catalyst ligand are as described elsewhere herein. In some aspects, the palladium catalyst is Pd$_2$(dba)$_3$ and the catalyst ligand is an aryl phosphate ligand. In some such aspects, the aryl phosphate ligand is XPhos. The equivalent ratio of palladium catalyst to compound 180 is about 0.001:1, about 0.002:1, about 0.003:1, about 0.004:1, or about 0.005:1, and ranges thereof, such as from 0.001:1 to about 0.005:1. The equivalent ratio of catalyst ligand to catalyst is about 1.3:1, about 1.5:1, about 1.7:1, about 1.9:1, about 2.5:1 or about 3:1, and ranges thereof, such as from about 1.3:1 to about 3 or from about 1.5:1 to about 2.5:1. The borylation reagent is as described elsewhere herein. The solvent is a polar aprotic solvent as described elsewhere herein. In some aspects, the polar aprotic solvent is THF. The ratio of solvent volume to compound 180 weight is about 3:1 L/kg, about 5:1 L/kg, about 10:1 L/kg, about 20:1 L/kg, or about 25:1 L/kg, and ranges thereof, such as from about 3:1 to about 25:1 L/kg, from about 5:1 to about 20:1 L/kg, or from about 5:1 to about 15:1 L/kg. In some aspects, the reaction mixture comprises a compound 180 concentration of about 0.1 moles/L, about 0.2 moles/L, about 0.3 moles/L, about 0.4 moles/L, or about 0.5 moles/L, and ranges thereof, such as from about 0.1 to about 0.5 moles/L. The equivalent ratio of the alkali metal acetate salt to compound 180 is greater than 1:1. In some aspects, the alkali metal acetate salt is potassium acetate. In some aspects, the borylation reagent is bis(pinacolato)diboron and the boronate is 4,4,5,5-tetramethyl-1,3,2-dioxaborolane. The equivalent ratio of borylation reagent to compound 180 is greater than 1:1, about 1.2:1, about 1.5:1 or about 2:1, and ranges thereof, such as between 1:1 and 2:1. In some aspects, the alkali metal acetate salt is potassium acetate. In some aspects, the borylation reagent is bis(pinacolato)diboron and the boronate is 4,4,5,5-tetramethyl-1,3,2-dioxaborolane. In such aspects, boronate compound 181 is the species of compound 182:

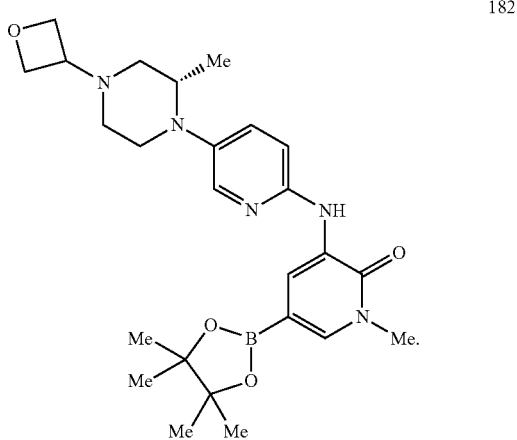 [SMILES: C[C@H]1CN(C2COC2)CCN1c1ccc(Nc2cc(B3OC(C)(C)C(C)(C)O3)cn(C)c2=O)nc1]

The reaction for forming compound 181 or 182 may be done with N$_2$ purging and/or a N$_2$ blanket. The reaction is may be done at reflux temperature, typically between about 60° C. and about 80° C. The reaction may be deemed complete when the area % concentration by HPLC of compound 160 is less than 1, less than 0.5, or less than 0.1. In some aspects, the reaction time to completion may be about 6 hours, about 12 hours, about 18 hours, about 24 hours, or more.

In some aspects, compound 181 or 182 may be isolated from the reaction product mixture. In some such aspects, the reaction product mixture may be combined with water at a ratio of water volume to compound 181 or 182 weight of about 2 L/kg, about 3 L/kg, about 4 L/kg or about 5 L/kg, and ratios thereof, such as from about 1 to about 5 L/kg or from about 2 to about 4 L/kg. An aqueous layer is separated and an organic layer comprising compound 181 or 182 in solution is collected. The organic layer may be distilled to a reduced volume at a ratio of volume to compound 181 or 182 weight of about 2 L/kg, about 3 L/kg, about 4 L/kg or about 5 L/kg, and ranges thereof, such as from about 2 to about 5 L/kg. Distillation is suitably vacuum distillation, such as for instance, at a temperature of at least 40° C. Alternatively, the distillation may be performed at atmospheric pressure. The reduced volume comprising compound 181 or 182 may be diluted with a polar aprotic solvent, such as THF, in a ratio of solvent volume to compound 181 or 182 weight of about from about 5 L/kg to about 8 L/kg, the diluted mixture is optionally filtered, and the diluted mixture may be distillated to a reduced volume of from about 2 to about 4 L per kg of compound 181 or 182. The polar aprotic solvent dilution and distillation step may be repeated one or more times. The reduced volume may be combined a non-polar solvent, such as MTBE, at a ratio of non-polar solvent volume to compound 181 or 182 weight of about 5 L/kg, about 10 L/kg, about 15 L/kg or about 20 L/kg, and ranges thereof, such as from about 5 to about 20 L/kg or from about 5 to about 15 L/kg. The admixture may be cooled to from about 0 to about 15° C. to form compound 181 or 182 as a solid dispersion. Solid compound 181 or 182 may be collected, such as by filtration or centrifugation, and dried to form solid compound 181 or 182.

Alternatively, after completion of the reaction to form compound 181 or 182, inorganic salts are filtered off at 60-65° C. The filtrate is cooled to 40-45° C. and filtered over charcoal. The volume of the filtrate is then reduced at atmospheric pressure. The reduced volume may be combined with a non-polar solvent, such as MTBE, at a ratio of non-polar solvent volume to compound 181 or 182 weight of about 5 L/kg, about 10 L/kg, about 15 L/kg or about 20 L/kg, and ranges thereof, such as from about 5 to about 20 L/kg or from about 5 to about 15 L/kg.

The yield of compound 181 or 182 based on compound 180 is at least 80%, at least 85% or at least 90%. The purity of compound 181 or 182 is at least 95 area %, at least 98 area % or at least 99 area % by HPLC.

In some aspects of the present invention, compound 180 may be prepared from compounds 90 and 141 according to the following reaction scheme:

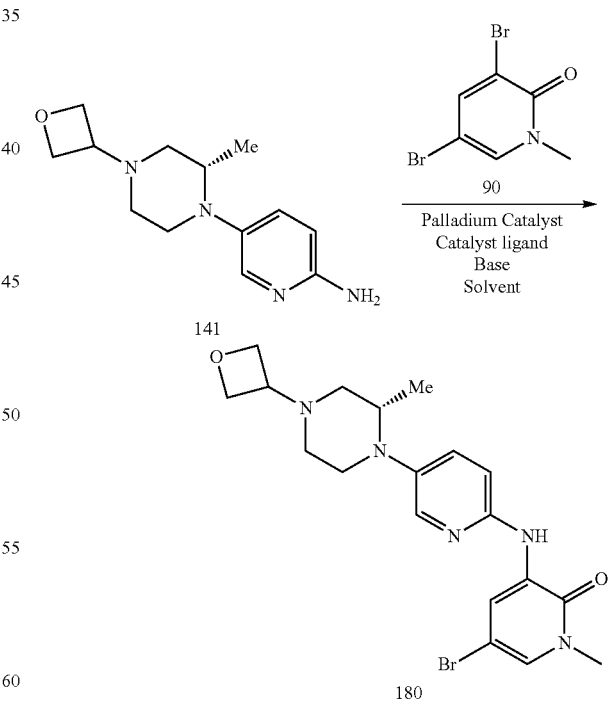

The method for preparing compound 180 comprises forming a reaction mixture comprising compound 141, compound 90, a palladium catalyst and an aryl phosphate catalyst ligand, a base, and an aprotic solvent. The reaction mixture is reacted to form a reaction product mixture comprising compound 180. Compound 180 is optionally isolated from the reaction product mixture.

The reaction mixture comprises approximately equimolar amounts of compounds 90 and 141. The aprotic solvent is as described elsewhere herein. In some aspects, the aprotic solvent is selected from THF, toluene, Me-THF, 1,4-dioxane, and combinations thereof. In some particular aspects, the solvent is 1,4-dioxane. The concentration of compound 141 in the solvent in the reaction mixture is about 2 w/w %, 4 w/w %, about 6 w/w %, about 8 w/w %, about 10 w/w %, about 12 w/w %, or about 14 w/w %, and ranges thereof, such as from about 2 to about 14 w/w % or from about 6 to about 10 w/w %. In some aspects, the source of compound 141 is solid compound 141 or a residue comprising compound 141. In some other aspects, the source of compound 141 is a solution of compound 141 in the solvent, wherein the solution comprises from about 3 to about 15 percent by weight compound 141 and less than 0.15 percent by weight methanol. The palladium catalyst and catalyst ligand are as described elsewhere herein. In some aspects, the palladium catalyst is $Pd_2(dba)_3$ and the catalyst ligand is Xantphos. The equivalent ratio of the palladium catalyst to compound 141 is from about 0.005:1 to about 0.05:1, or from about 0.01:1 to about 0.03:1. The equivalent ratio of the catalyst ligand to the catalyst is from about 1.2:1 to about 3:1 or from about 1.5:1 to about 2.5:1. In some aspects, the base is an inorganic base as described elsewhere herein. In some such aspects, the base is potassium carbonate or tripotassium phosphate. The mole ratio of the base to compound 141 is from about 1.5:1 to about 3:1.

The reaction for forming compound 180 may be done with $N_2$ purging and/or a $N_2$ blanket. The reaction may be done at reflux temperature, typically between about 80° C. and about 120° C. The reaction may be deemed complete when the area % concentration by HPLC of compound 180 is less than 2, less than 1, less than 0.5, or less than 0.1. In some aspects, the reaction time to completion may be about 6 hours, about 12 hours, about 18 hours, about 24 hours, about 30 hours, or more.

In some aspects, compound 180 may be isolated from the reaction product mixture. In some such aspects, the reaction product mixture may be cooled to from about 50° C. to about 85° C. and filtered. The filtrate may optionally be washed with aprotic solvent (e.g., 1,4-dioxane) and the wash may be combined with the filtrate. The filtrate may be concentrated to almost dryness. In some aspects, the concentration may be done in a vacuum at a temperature of from about 45 to about 75° C. to form a residue of compound 180. The residue may be optionally purified by combining the residue with methanol to form a slurry of compound 180 at a ratio of methanol volume to compound 180 weight of about 2:1 L/kg, about 3:1 L/kg, about 4:1 L/kg, about 5:1 L/kg or about 6:1 L/kg, and ranges thereof, such as from about 2:1 to about 6:1 L/kg or from about 2:1 to about 4:1 L/kg. The slurry may be cooled to from about −5 to about 10° C. and stirred for at least 1 hour. Crude compound 180 solids may be collected, such as by filtration or centrifugation, and the solid may be optionally washed with cold methanol. The crude solids may be dried under vacuum, such as for instance, at a temperature of from about 45 to about 75° C. for at least 0.5 hours. The dried crude solids may be combined with a aprotic solvent (e.g., 1,4-dioxane) as a w/w ratio of solvent to compound 180 of from about 1.1:1 to about 2:1 or from about 1.2:1 to about 1.7:1 and the resulting mixture may be heated to reflux temperature and stirred for at least 0.1 hour at reflux temperature. i-propanol may be added to the heated mixture at a ratio of i-propanol volume to compound 180 weight of from about 1.5:1 to about 6:1 L/kg or from about 2.5:1 to about 5:1 L/kg. The resulting mixture may be cooled to from about 10 to about 30° C. and stirred at that temperature to form a slurry comprising solid compound 180. Solid compound 180 may be collected, such as by filtration or centrifugation, and the collected solids may be optionally washed with i-propanol. Compound 180 solids may be dried under vacuum, such as at a temperature from about 50 to about 80° C., for at least 2 hours.

The yield of compound 180 is at least 60%, at least 70%, or at least 80%. The purity of compound 180 is at least 95 area %, at least 98 area %, or at least 99 area % by HPLC.

In some aspects of the present invention, compound 141 may be prepared from compound 140 according to the following reaction scheme:

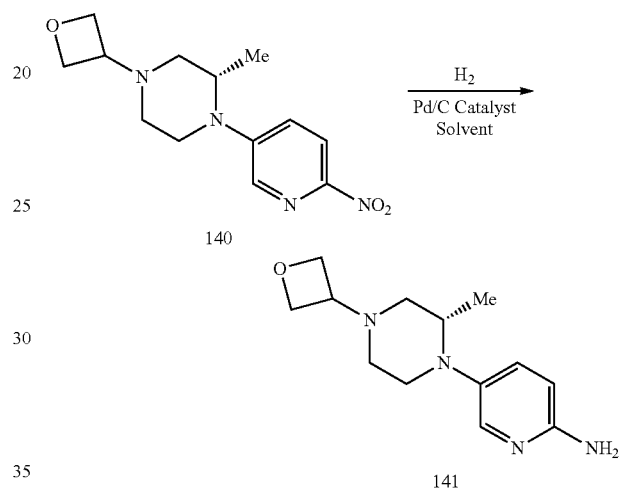

The method for preparing compound 141 comprises forming a reaction mixture comprising compound 140, a palladium on carbon catalyst, hydrogen, and a solvent selected from methanol, ethanol, isopropanol, dioxane, toluene, and combinations thereof. The reaction mixture is reacted to form a reaction product mixture comprising compound 141.

The ratio of the solvent volume to compound 140 weight is about 3:1 L/kg, about 5:1 L/kg, about 10:1 L/kg, 15:1 L/kg, or about 20:1 L/kg, and range thereof, such as from about 3:1 to about 20:1 L/kg, from about 3:1 to about 10:1 L/kg, or from about 4:1 to about 6:1 L/kg. In some aspects, the solvent is methanol. The weight ratio of the catalyst to compound 140 is from about 10 w/w %, about 15 w/w %, about 20 w/w %, about 25 w/w % or about 30 w/w % and ranges thereof, such as from about 10 to about 30 w/w %, or from about 10 to about 25 w/w %.

The reaction for forming compound 141 may be done with $N_2$ purging prior to introducing Hz. The reaction is typically done at a temperature of from about 35° C. to about 65° C. or form about 45° C. to about 55° C. In some aspects, the reaction time to completion may be about 6 hours, about 12 hours, about 18 hours, about 24 hours, or more. The reaction may be deemed complete when the area % concentration by HPLC of compound 140 is less than 2, less than 1, less than 0.5, or less than 0.1. The reaction product mixture is filtered and the filtrate comprises compound 141 in solution.

In some aspects, compound 141 may be isolated from the reaction product mixture as a residue by concentration of the filtrate to almost dryness. In some aspects, the concentration may be done in a vacuum at a temperature below 60° C. In some optional aspects, the compound 141 residue may be combined with an aprotic solvent such as THF, toluene, Me-THF or 1,4-dioxane followed by concentration to almost dryness. In some aspects, the concentration may be done in a vacuum at a temperature below 60° C. to form a residue. The ratio of solvent volume to compound 141 weight in such aspects is about 3:1 L/kg, about 5:1 L/kg, about 7:1 L/kg or about 9:1 L/kg and ranges thereof, such as from about 3:1 to about 9:1 L/kg or from about 3:1 to about 7:1 L/kg. In some aspects, the solvent is 1,4-dioxane. The residue may optionally be combined with the aprotic solvent at a ratio of solvent volume to compound 141 weight of about 5:1 L/kg, about 10:1 L/kg or about 15:1 L/kg or about 20:1 L/kg and ranges thereof, such as from about 5:1 to about 20:1 L/kg or from about 5:1 to about 15:1 L/kg. In some such aspects, the final concentration of compound 141 in the aprotic solvent (e.g., 1,4-dioxane) is from about 5 to about 15 percent by weight.

The yield of compound 141 is at least 90% or at least 95%.

In some aspects of the present invention, compound 140 may be prepared from compounds 20 and 153 according to the following reaction scheme:

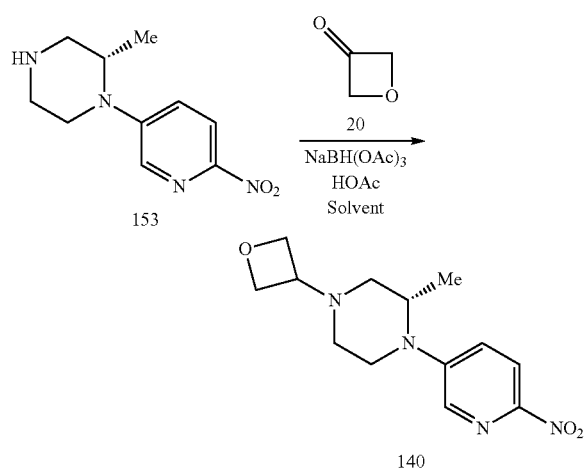

The method for preparing compound 140 comprises forming a reaction mixture comprising compound 153, compound 20, a solvent, NaBH(OAc)₃, and acetic acid. In some aspects, the reaction mixture further comprises a drying agent. The reaction mixture is reacted to form a reaction product mixture comprising compound 140. Compound 140 may optionally be isolated from the reaction product mixture.

The solvent is selected from THF, Me-THF, DCM, and combinations thereof. In some aspects, the solvent is DCM. In some aspects the source of compound 153 is a solution of compound 153 in the solvent. In any of the various aspects, the concentration of compound 153 in the solvent is from about 2 to about 10 percent by weight. The equivalent ratio of compound 20 to compound 153 is from about 1.3:1 to about 1.9:1. The equivalent ratio of acetic acid to compound 153 is from about 1.1:1 to about 3:1. The equivalent ratio of NaBH(OAc)₃ to compound 153 is greater than 1.5:1. In some aspects, the drying agent is magnesium sulfate wherein the equivalent ratio of magnesium sulfate to compound 153 is from about 0.3:1 to about 0.6:1.

The reaction for forming compound 140 may be done with N₂ purging and/or with an N₂ blanket. The reaction is typically done at a temperature of from about 30° C. to about 50° C. In some aspects, the reaction time to completion may be about 0.5 hours, about 1 hour, about 2 hours, about 4 hours, or more. The reaction may be deemed complete when the area % concentration by HPLC of compound 153 is less than 2, less than 1, less than 0.5, or less than 0.1.

In some aspects, compound 140 may be isolated from the reaction product mixture. In such aspects, the reaction product mixture may be combined with water at a ratio of water volume to compound 140 weight of about 3:1 L/kg about 5:1 L/kg, about 7:1 L/kg, about 9:1 L/kg or about 11:1 L/kg and ranges thereof, such as from about 3:1 to about 11:1 L/kg or from about 5:1 to about 9:1 L/kg. The phases are separated to form an aqueous phase and a first organic phase comprising compound 140 in solution. The aqueous phase may be extracted with the solvent (e.g., DCM) at ratio of solvent volume to compound 140 weight of from about 1 L/kg to about 5 L/kg or from about 2 L/kg to about 4 L/kg, and the phases separated to form a second organic phase comprising compound 140 in solution in the solvent. The first and second organic phases may be combined and washed with water. In some aspects, the volume of wash water is approximately the same as the volume of solvent used to form the second organic phase. The washed combined organic phases may be optionally washed at least one more time with water. The washed organic phases comprising compound 140 in solution may be dried with a drying agent (e.g., magnesium sulfate), and then filtered. The filtrate may be optionally further washed with solvent (e.g., DCM). The filtrate may be concentrated to almost dryness under vacuum at a temperature below 50° C. to form compound 140 residue. Optionally, the residue may be combined with a non-polar solvent to form a mixture having a ratio of solvent volume to compound 140 weight of from about 1.5:1 L/kg to about 4:1 L/kg. In some aspects, the non-polar solvent is petroleum ether. The mixture may be stirred at from about 5 to about 35° C. for a time sufficient to form a solution of compound 140. The solution may then be filtered and concentrated to dryness under a vacuum at a temperature of from about 40 to about 70° C. to form solid compound 140.

The yield of compound 140 is at least 85% or at least 90%. The purity of compound 140 is at least 95%, at least 98% or at least 98.5% by HPLC.

In some aspects of the invention, compound 153 may be prepared from compound 152 according to the following reaction scheme:

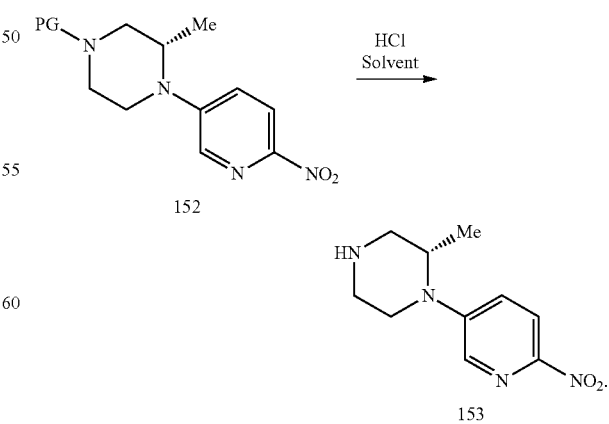

The method for preparing compound 153 comprises forming a reaction mixture comprising compound 152 having a protecting group moiety, PG, hydrochloric acid, and a solvent comprising water. The reaction mixture is reacted to form a reaction product mixture comprising deprotected compound 152. Compound 152 may optionally be isolated from the reaction product mixture. In some aspects, PG is BOC.

The reaction for forming compound 153 may be done with $N_2$ purging and/or with an $N_2$ blanket. The reaction is typically done at a temperature of from about 40 to about 70° C. or from about 50 to about 60° C. In some aspects, the reaction time to completion may be about 1 hour, about 2 hour, about 3 hours, about 4 hours, or more. The reaction may be deemed complete when the area % concentration by HPLC of compound 152 is less than 2, less than 1, less than 0.5, or less than 0.1.

In some aspects, compound 153 may be isolated from the reaction product mixture. In such aspects, the reaction product mixture may be cooled, such as for instance to from about 10 to about 30° C., and the reaction mixture may be extracted with a non-polar solvent as described elsewhere herein (e.g., DCM) at a ratio of solvent volume to compound 153 weight of from about 3:1 L/kg to about 11:1 L/kg or from about 5:1 L/kg to about 9 L/kg. The aqueous phase may be collected and the pH thereof adjusted to greater than 11 with an aqueous strong inorganic base, for instance, about 30% NaOH. The pH-adjusted aqueous phase may be extracted with a non-polar solvent (e.g., DCM) at a ratio of solvent volume to compound 153 weight of from about 5:1 L/kg to about 20:1 L/kg or from about 8:1 L/kg to about 15:1 L/kg. A second aqueous phase extraction with the non-polar solvent may be done. The organic phases are combined and may be washed at least once with water in a volume generally consistent with the volume of each non-polar solvent extraction. The combined washed organic phases may then be dried with a drying agent (e.g., $MgSO_4$) and filtered. The filtrate comprises compound 153 in solution at a concentration of about 2 w/w %, about 4 w/w %, about 6 w/w % or about 8 w/w %, and ranges thereof, such as from about 2 to about 8 w/w % or from about 2 to about 6 w/w %. In some aspects, solid compound 153 may be obtained by solvent evaporation under vacuum. In some other aspects, the solution of compound 153 may be used directly for the preparation of compound 140. The yield of compound 153 is at least 80% or at least 90%.

In some particular aspects of the invention, compound 200 is prepared according to the method depicted in FIG. 1. In some other particular aspects of the invention, compound 200 is prepared according to the method depicted in FIG. 2.

Figure 3:
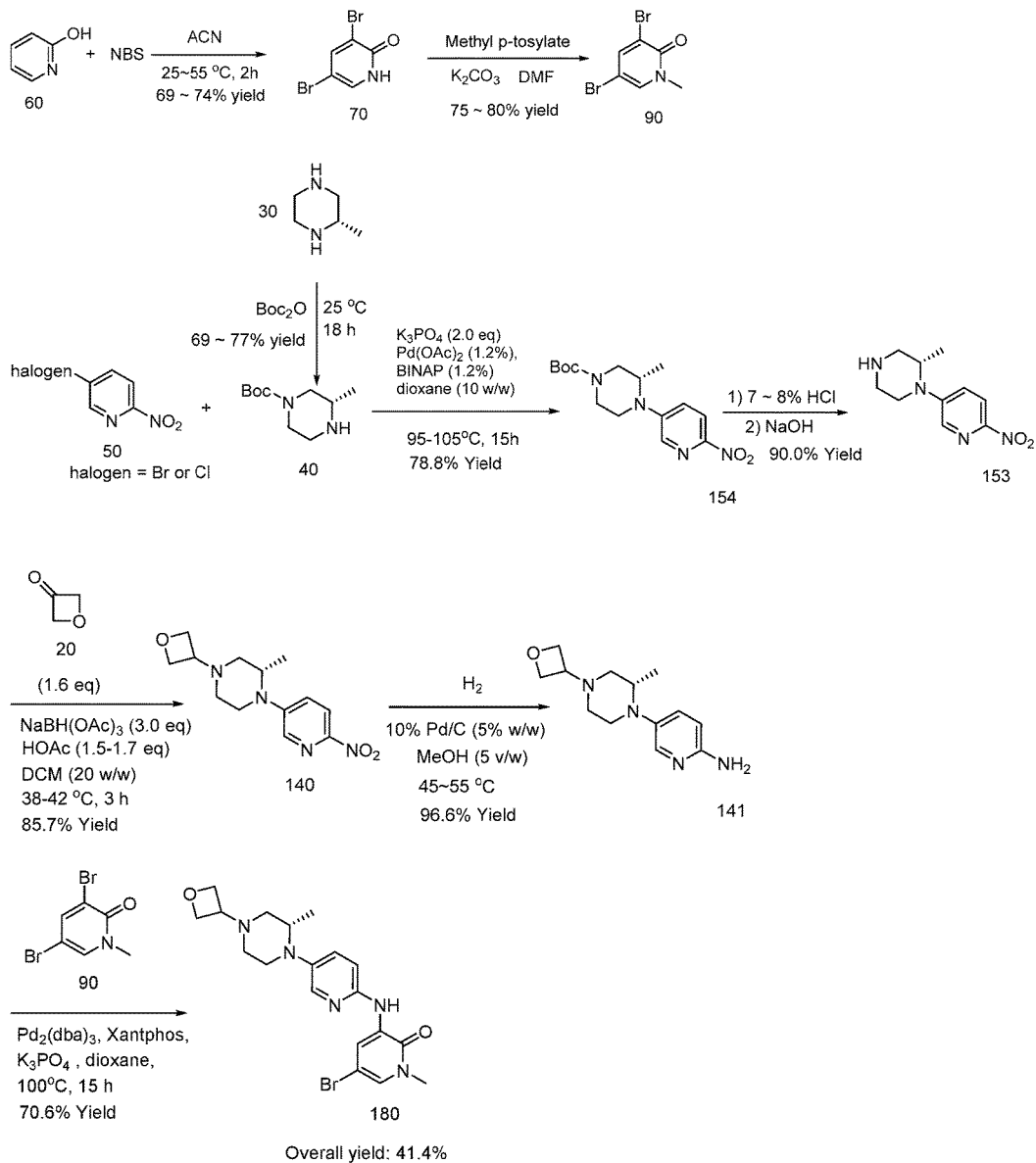
FIG. 3 shows a method for the preparation of compounds 70, 90, 40, 154, 153, 140, 141 and 180.
Figure 4:
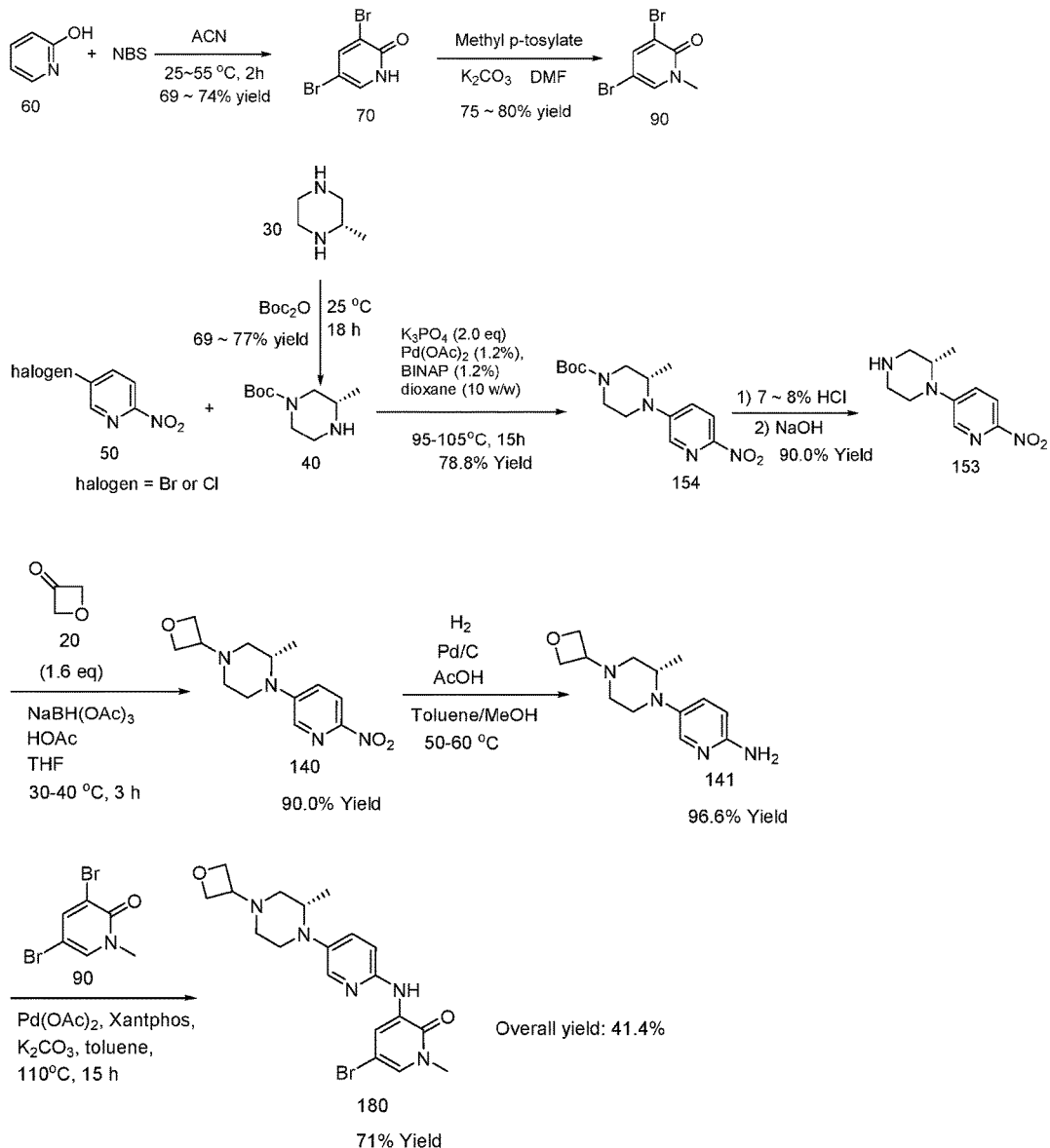
FIG. 4 shows a method for the preparation of compounds 70, 90, 40, 154, 153, and another method for the preparation of compounds 140, 141 and 180.

In some particular aspects of the invention depicted in FIGS. 3 and 4 and as generally described elsewhere herein: (1) compound 60 and N-bromosuccinimide are reacted to form compound 70; (2) compound 70 and methyl-p-tosylate are reacted to form compound 90; (3) compound 30 and di-tert-butyl dicarbonate are reacted to form Boc-protected compound 40; (4) compounds 50 and 40 are reacted in the presence of palladium catalyst and a catalyst ligand to form compound 154; (5) compound 154 is de-protected to form compound 153; (6) compound 153 and compound 20 are reacted to form compound 140; (7) compound 140 is reduced by hydrogenation in the presence of a palladium on carbon catalyst to form compound 141; and (8) compound 141 is reacted with compound 90 in the presence of a palladium catalyst and a catalyst ligand to form compound 180.

Figure 5:
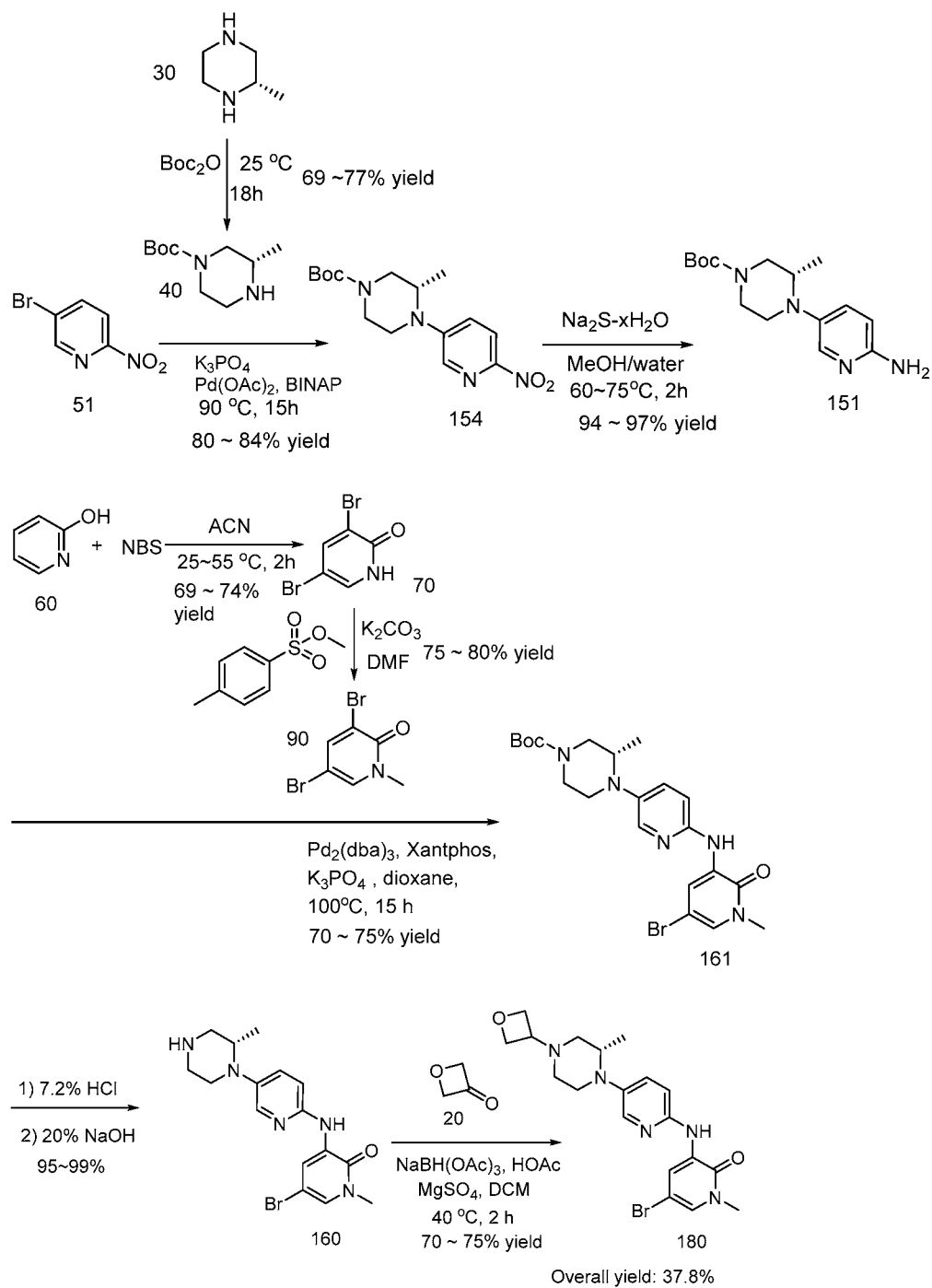
FIG. 5 shows a method for the preparation of compounds 40, 154, 151, 70, 90, 161, 160 and 180.

In some other particular aspects of the invention, compound 180 is prepared according to the method depicted in FIG. 5. A reaction mixture comprising compound 30, di-tert-butyl dicarbonate, and a suitable solvent is formed, and the reaction mixture is reacted at about 25° C. for about 18 hours to form a reaction product mixture comprising Boc-protected compound 40 at a yield of from about 69% to about 77%. A reaction mixture comprising compound 51, compound 40, a suitable solvent, $K_3PO_4$, $Pd(OAc)_2$ catalyst and BINAP ligand is formed, and the reaction mixture is reacted at about 90° C. for about 15 hours to form a reaction product mixture comprising BOC-protected compound 154 at a yield of from about 80% to about 84%. A reaction mixture comprising compound 154, sodium sulfide hydrate, and a solvent system comprising methanol and water is formed, and the reaction mixture is reacted at from about 60° C. to about 75° C. for about 2 hours to form a reaction product comprising compound 151 at a yield of from about 94% to about 97%. A reaction mixture comprising compound 60, N-bromosuccinimide and acetonitrile is formed, and the reaction mixture is reacted at from about 25° C. to about 55° C. for about 2 hours to form a reaction product mixture comprising compound 70 at a yield of from about 69% to about 74%. A reaction mixture comprising compound 70, methyl-p-tosylate, $K_2CO_3$ and DMF is formed, and the reaction mixture is reacted to form a reaction product mixture comprising compound 90 at a yield of from about 75% to about 80%. A reaction mixture comprising compound 151, compound 90, $Pd_2(dba)_3$ catalyst, a Xantphos catalyst ligand, and dioxane is formed, and the reaction mixture is reacted at about 100° C. for about 15 hours to form a reaction product mixture comprising Boc-protected compound 161 at a yield of from about 70% to about 75%. Compound 161 is de-protected with about 7.2% HCl followed by neutralization with about 20% NaOH to produce a reaction product mixture comprising compound 160 at a yield of from about 95 to about 99%. A reaction mixture comprising compound 160, compound 20, $NaBH(OAc)_3$, acetic acid, magnesium sulfate, and DCM is formed, and the reaction mixture is reacted at about 40° C. for about 2 hours to form a reaction product mixture comprising compound 180 at a yield of from about 70% to about 75%. The overall yield based on compound 51 is about 38%.

Figure 6:
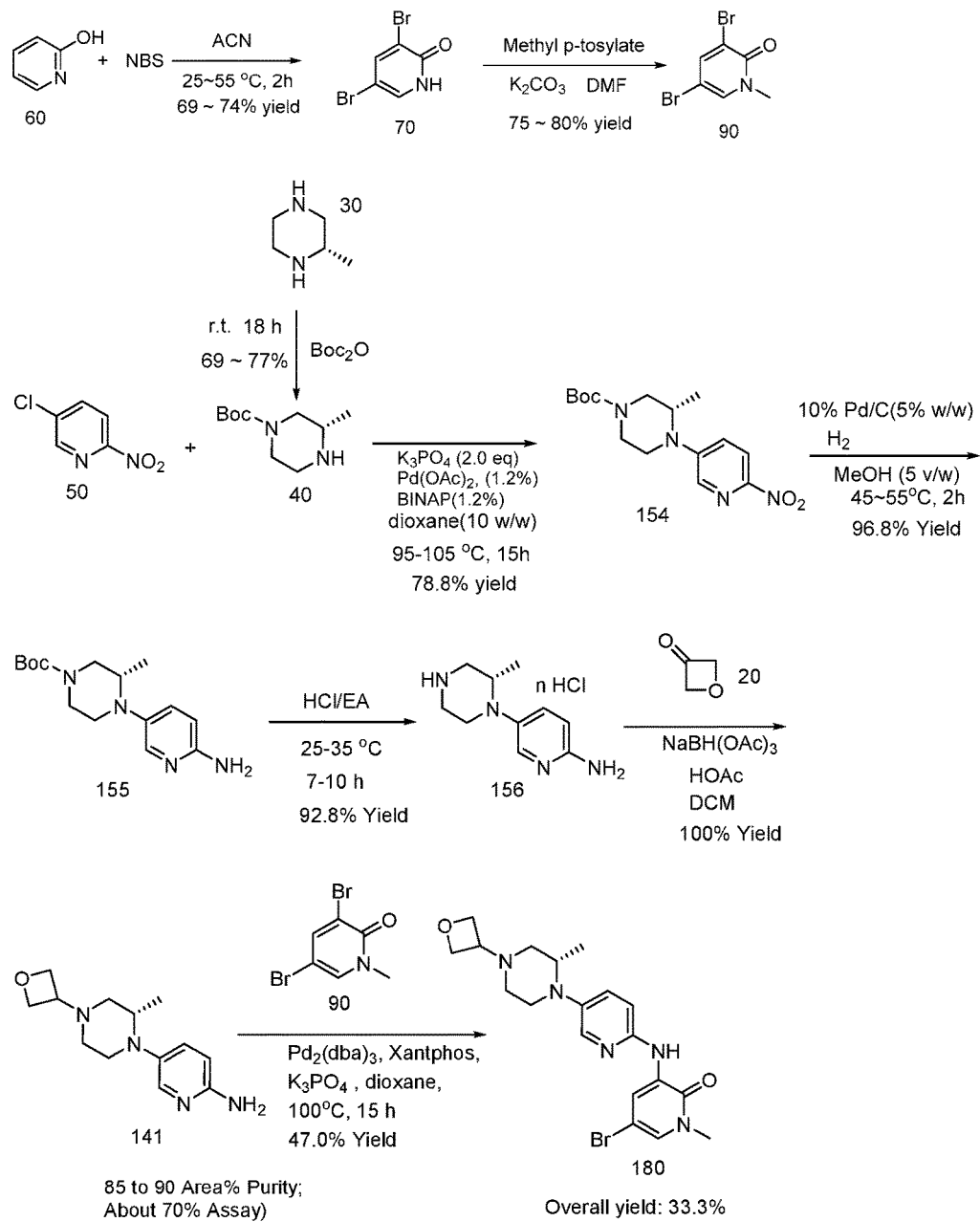
FIG. 6 shows a method for the preparation of compounds 40, 154, 155, 156, 141 and 180.

In some other particular aspects of the invention, compound 180 is prepared according to the method depicted in FIG. 6. A reaction mixture comprising compound 60, N-bromosuccinimide and acetonitrile is formed, and the reaction mixture is reacted at from about 25° C. to about 55° C. for about 2 hours to form a reaction product mixture comprising compound 70 at a yield of from about 69% to about 74%. A reaction mixture comprising compound 70, methyl-p-tosylate, $K_2CO_3$ and DMF is formed, and the reaction mixture is reacted to form a reaction product mixture comprising compound 90 at a yield of from about 75% to about 80%. A reaction mixture comprising compound 30, di-tert-butyl dicarbonate, and a suitable solvent is formed, and the reaction mixture is reacted at about 25° C. for about 18 hours to form a reaction product mixture comprising Boc-protected compound 40 at a yield of from about 69% to about 77%. A reaction mixture comprising compound 50, compound 40, dioxane, $K_3PO_4$, $Pd(OAc)_2$ catalyst and BINAP ligand is formed. In the reaction mixture, the concentration of compound 50 in dioxane is about 10 w/w %, the equivalent ratio of $K_3PO_4$ to compound 50 is about 2, the equivalent ratio of $Pd(OAc)_2$ catalyst to compound 50 is about 0.012:1, and the equivalent ratio of $Pd(OAc)_2$ catalyst to BINAP ligand is about 1:1. The reaction mixture is reacted at from about 95° C. to about for about 105° C. for about 15 hours to form a reaction product mixture comprising BOC-protected compound 154 at a yield of about 79%. A reaction mixture comprising compound 154, methanol, 10% palladium on carbon catalyst and hydrogen is formed. In the reaction mixture, the ratio of methanol volume to compound 154 weight is about 5:1, and the weight ratio of the palladium on carbon catalyst to compound 154 is about 0.05:1. The hydrogenation reaction mixture is reacted at from about 45° C. to about 55° C. for about 2 hours to form a reaction product mixture comprising compound 155 at a yield of about 97%. Compound 155 is de-protected with HCl in a solvent system comprising ethyl acetate at a temperature of from about 25° C. to about for about 35° C. for from about 7 hours to about 10 hours to form de-protected compound 156 at a yield of about 93%. A reaction mixture comprising compound 156, compound 20, NaBH(OAc)$_3$, acetic acid, and DCM is formed, and the reaction mixture is reacted to form a reaction product mixture comprising compound 141 at a yield of about 100% wherein the purity of compound 141 is from about 85 area % to about 90 area % by HPLC. A reaction mixture comprising compound 141, compound 90, Pd$_2$(dba)$_3$ catalyst, Xantphos catalyst ligand, K$_3$PO$_4$, and dioxane was formed, and the reaction mixture was reacted at about 100° C. for about 15 hours to form compound 180 at a yield of about 47%. The overall yield of compound 180 based on compound 50 is about 33%.

Figure 7:
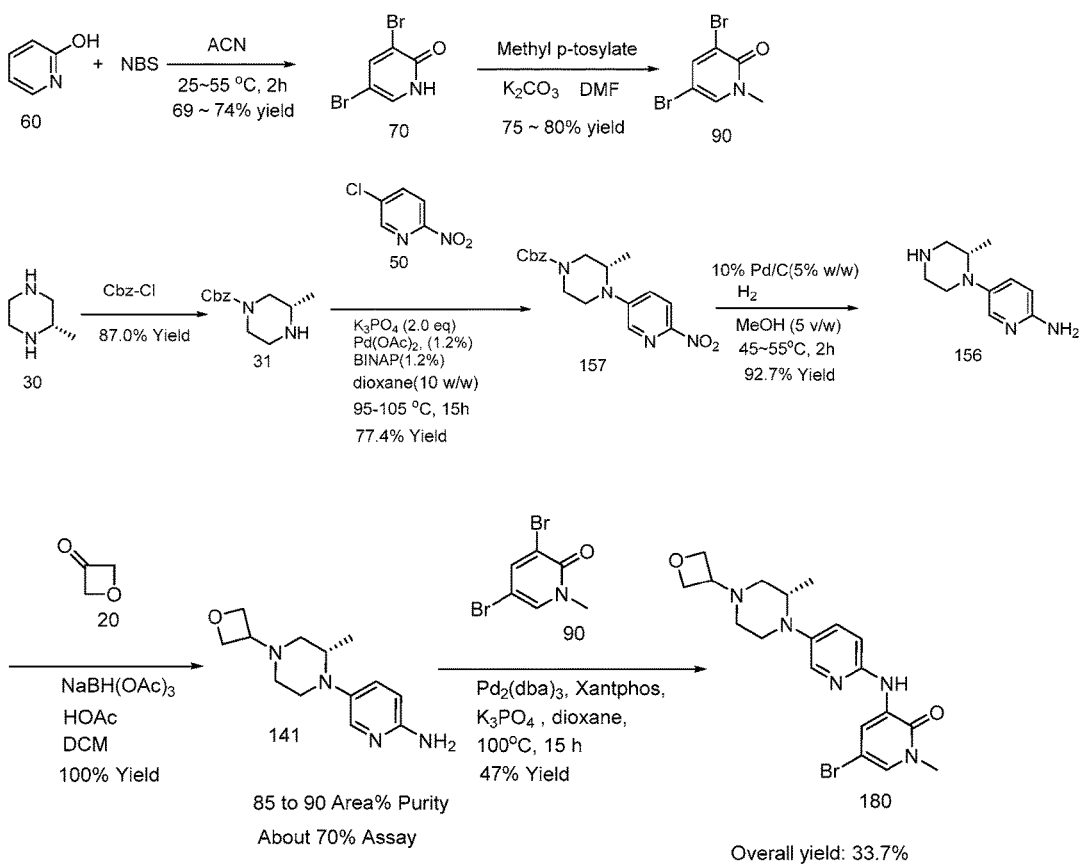
FIG. 7 shows a method for the preparation of compounds 31, 157, 156, 141, and 180.

In some other particular aspects of the invention, compound 180 is prepared according to the method depicted in FIG. 7. A reaction mixture comprising compound 60, N-bromosuccinimide and acetonitrile is formed, and the reaction mixture is reacted at from about 25° C. to about 55° C. for about 2 hours to form a reaction product mixture comprising compound 70 at a yield of from about 69% to about 74%. A reaction mixture comprising compound 70, methyl-p-tosylate, K$_2$CO$_3$ and DMF is formed, and the reaction mixture is reacted to form a reaction product mixture comprising compound 90 at a yield of from about 75% to about 80%. A reaction mixture comprising compound 30, benzyl chloroformate ("Cbz-Cl"), and a suitable solvent is formed, and the reaction mixture is reacted to form Cbz-protected compound 31 at a yield of about 87%. A reaction mixture comprising compound 50, compound 31, dioxane, K$_3$PO$_4$, Pd(OAc)$_2$ catalyst and BINAP ligand is formed. In the reaction mixture, the concentration of compound 50 in dioxane is about 10 w/w %, the equivalent ratio of K$_3$PO$_4$ to compound 50 is about 2, the equivalent ratio of Pd(OAc)$_2$ catalyst to compound 50 is about 0.012:1, and the equivalent ratio of Pd(OAc)$_2$ catalyst to BINAP ligand is about 1:1. The reaction mixture is reacted at from about 95° C. to about 105° C. for about 15 hours to form a reaction product mixture comprising Cbz-protected compound 157 at a yield of about 77%. A reaction mixture comprising compound 157, methanol, 10% palladium on carbon catalyst and hydrogen is formed. In the reaction mixture, the ratio of methanol volume to compound 157 weight is about 5:1, and the weight ratio of the palladium on carbon catalyst to compound 157 is about 0.05:1. The hydrogenation reaction mixture is reacted at from about 45° C. to about 55° C. for about 2 hours to form a reaction product mixture comprising de-protected compound 156 at a yield of about 93%. A reaction mixture comprising compound 156, compound 20, NaBH(OAc)$_3$, acetic acid, and DCM is formed, and the reaction mixture is reacted to form a reaction product mixture comprising compound 141 at a yield of about 100% wherein the purity of compound 141 is from about 85 area % to about 90 area % by HPLC. A reaction mixture comprising compound 141, compound 90, Pd$_2$(dba)$_3$ catalyst, Xantphos catalyst ligand, K$_3$PO$_4$, and dioxane was formed, and the reaction mixture was reacted at about 100° C. for about 15 hours to form a reaction product mixture comprising compound 180 at yield of about 47%. The overall yield of compound 180 based on compound 50 is about 33%.

Preparation of Compound 400

In some aspects of the present invention, tricyclic lactam compound 400, stereoisomers thereof, geometric isomers thereof, tautomers thereof, and salts thereof, may be prepared from compounds 300 and 310 according to the following reaction scheme:

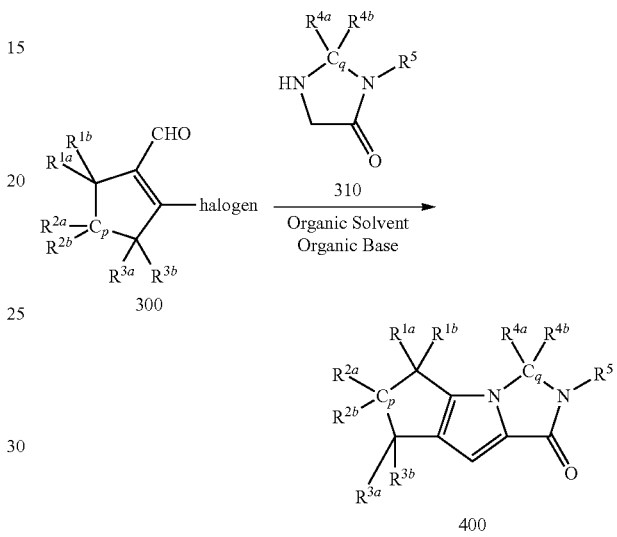

The method for preparing compound 400 comprises forming a reaction mixture comprising an organic solvent, an organic base, and compounds 300 and 310 and reacting the reaction mixture to form a reaction product mixture comprising the tricyclic lactam of compound 400.

$R^{1a}$, $R^{1b}$, $R^{2a}$, $R^{2b}$, $R^{3a}$, $R^{3b}$, $R^{4a}$ and $R^{4b}$ are independently selected from H, and $C_{1-6}$ alkyl. $R^5$ is selected from H, $C_{1-6}$ alkyl, cycloalkyl, aryl, substituted aryl, benzyl, substituted benzyl, heteroaryl, substituted heteroaryl. In some aspects, $R^{1a}$, $R^{1b}$, $R^{3a}$, $R^{3b}$, $R^{4a}$, $R^{4b}$ and $R^5$ are H, and $R^{2a}$ and $R^{2b}$ are —CH$_3$.

The halogen is as described elsewhere herein. In some aspects, the halogen is Cl or Br. In some other aspects, the halogen is Cl.

p is 1, 2, 3 or 4. In some aspects, p is 1 or 2. q is 1, 2, 3 or 4. In some aspects, q is 1 or 2. In some other aspects, p is 1 and q is 2.

In some aspects, the tricyclic lactam of compound 400 is species compound 160 of the structure:

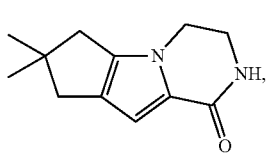

compound 300 is the species of compound 130 of the structure:

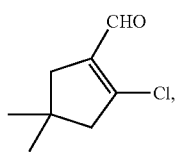

and compound 310 is piperazine-2-one of compound 10:

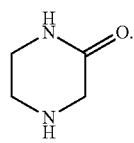

The organic base is as described elsewhere herein. In some aspects, the organic base is a tri-$C_{1-6}$ alkyl amine. In some particular aspects, the organic base is selected from 4-methylmorpholine and N-ethyldiiopropylamine.

In some aspects, the organic solvent is a polar aprotic solvent as described elsewhere herein. In some particular aspects, the solvent is selected from NMP and DMF.

In some aspects, the concentration of compound 300 in the reaction mixture is from about 0.25 to about 2 moles/L, from about 0.5 to about 1.5 moles/L or from about 0.5 to about 1 moles/L. In some aspects, the ratio of solvent volume to compound 300 weight is about 1.5:1 L/kg, about 2:1 L/kg, about 3:1 L/kg, about 4 L/kg, about 5:1 L/kg, about 6:1 L/kg, about 7:1 L/kg, about 8:1 L/kg, about 9:1 L/kg, or about 10:1 L/kg, and ratios thereof, such as from about 1.5:1 to about 10:1 L/kg, from about 2:1 to about 6:1 L/kg, or from about 2:1 to about 4:1 L/kg. The equivalent ratio of the organic base to compound 300 is between 1:1 and 2:1, about 1.05:1, about 1.1:1, about 1.2:1, about 1.3:1, about 1.4:1, about 1.5:1, about 1.6:1, about 1.7:1, about 1.8:1, about 1.9:1, and ranges thereof, such as from about 1.05:1 to about 1.9:1, or from about 1.1:1 to about 1.5:1. In some aspects, compound 300 is present in stoichiometric excess over compound 310. In some aspects the equivalent ratio of compound 310 to compound 300 is between 0.7:1 and 1:1. In some other aspects, the equivalent ratio of compound 310 to compound 300 is about 0.7:1, about 0.75:1, about 0.8:1, about 0.85:1, about 0.9:1, about 0.95:1 or about 0.99:1, and ranges thereof, such as from about 0.7:1 to about 0.99:1, or from about 0.75:1 to about 0.95:1.

The reaction for forming a reaction product mixture comprising compound 400 may be done with $N_2$ purging and/or with an $N_2$ blanket. In some aspects, the organic solvent, organic base and compound 310 are combined in a reactor with agitation at a temperature of from about 95 to about 125° C. or from about 100 to about 120° C. Compound 300 is then added to the reactor with agitation while maintaining the temperature. In some aspects, compound 300 is in solution in an organic solvent (e.g., toluene or NMP) as described elsewhere herein. In some aspects, the reaction time to completion may be about 0.25 hours, about 0.5 hours, about 1 hour, about 2 hours, about 3 hours, or more. The reaction may be deemed complete when the area % concentration by HPLC of compound 300 is less than 5, less than 2, less than 1, less than 0.5, or less than 0.1.

Compound 400 may be isolated from the reaction product mixture. In some isolation aspects, the reaction product mixture may be cooled, such as for instance to from about 80 to about 95° C. Water may then be combined with the reaction product mixture to form a mixture wherein the ratio of water volume to compound 300 starting material weight is about 3:1 L/kg, about 5:1 L/kg, about 7:1 L/kg, about 9:1 L/kg, about 11:1 L/kg, about 13:1 L/kg, or about 15:1 L/kg, and ranges thereof, such as from about 3:1 to about 15:1 L/kg or from about 5:1 to about 10:1 L/kg. The mixture is cooled to from about 5 to about 30° C. and stirred at temperature for at least 0.5 hours, at least 1 hour, at least 2 hours or at least 3 hours to form a slurry comprising solid compound 400. Solid compound 400 may be collected, such as by filtration or centrifugation. The solids may optionally be subjected to a second water slurry and collection step. Acetone may then be combined with the solid compound 400 to form a slurry, for instance at a temperature of from about 10 to about 30° C., wherein the ratio of acetone volume to compound 300 starting material weight is about 1.5:1 L/kg, about 2:1 L/kg, about 3:1 L/kg, about 4:1 L/kg, about 5:1 L/kg, or about 6:1 L/kg, and ranges thereof, such as from about 1.5:1 to about 6:1 L/kg or from about 2:1 to about 4:1 L/kg. The slurry may be agitated for at least 1 hour, at least 2 hours or at least 3 hours. Solid compound 400 may be isolated, such as by filtration or centrifugation. The collected solids may be optionally washed with acetone. The solid compound 400 may be dried. In some drying aspects, drying may be done under vacuum at a temperature of from about 25 to about 50° C.

The yield of compound 400 is at least 50% at least 60% or at least 70%. The purity of compound 400 by HPLC is at least 98 area %, at least 99 area %, or at least 99.5 area % by HPLC. In aspects directed to tricyclic lactam species compound 160 prepared from compounds 130 and 10, impurities are believed to include the following structures:

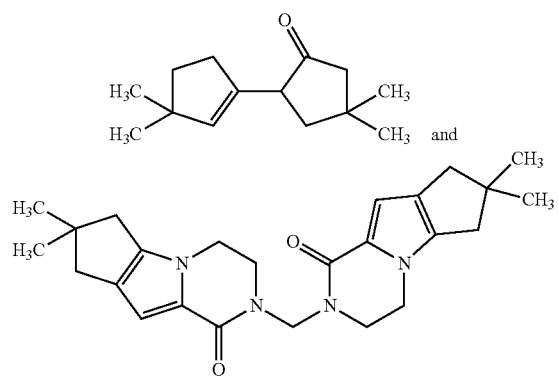

In some aspects, compound 300 may be prepared from compound 320 according to the following reaction scheme:

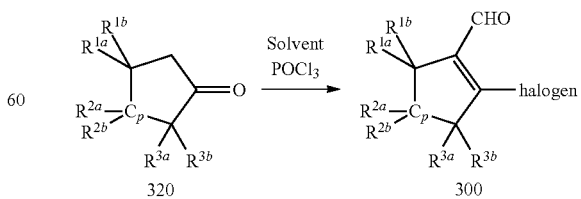

The method for preparing compound 300 comprises forming a reaction mixture comprising a polar aprotic solvent, a non-polar solvent, phosphorous oxychloride and compound 320. The reaction mixture may be reacted to form a reaction product mixture comprising compound 300.

$R^{1a}$, $R^{1b}$, $R^{2a}$, $R^{2b}$, $R^{3a}$ and $R^{3b}$ are independently selected from H, and $C_{1-6}$ alkyl. In some aspects, $R^{1a}$, $R^{1b}$, $R^{3a}$ and $R^{3b}$ are H, and $R^{2a}$ and $R^{2b}$ are —$CH_3$. p is 1,2, 3 or 4. In some aspects, p is 1 or 2. In other aspects, p is 1.

The polar aprotic solvent is as described elsewhere herein. In some aspects, the polar aprotic solvent is DMF. The non-polar solvent is as described elsewhere herein. In some aspects, the non-polar solvent is DCM.

The reaction mixture may be formed as follows, and the reaction may be done under a $N_2$ blanket and/or with a $N_2$ purge. A reactor is charged with the non-polar solvent (e.g., DCM) at a ratio of non-polar solvent volume to compound 320 starting material weight of about 3 L/kg, about 5 L/kg, about 7 L/kg, about 9 L/kg, about 11 L/kg, about 13 L/kg, or about 15 L/kg, and ranges thereof, such as from about 3 to about 15 L/kg or from about 5 to about 11 L/kg, and with the polar aprotic solvent (e.g., DMF) at an equivalent ratio to compound 320 starting material of about 1.5:1, about 2:1, about 2.5:1, about 3:1, about 4:1 or about 5:1, and ranges thereof, such as from about 1.5:1 to about 5:1 or from about 2:1 to about 3:1. The temperature of the solvent combination is adjusted to from about 5 to about 25° C., and $POCl_3$ is added to the reactor wherein the equivalent ratio of $POCl_3$ to compound 320 is about 1.5:1 about 2:1, about 2.25:1, about 2.5:1 or about 3:1, and ranges thereof, such as from about 1.5:1 to about 3:1 or from about 2:1 to about 2.25:1. The mixture may be optionally stirred at temperature for at least 0.5 hours or at least 1 hour. Compound 320 is then added to the reactor, at a temperature such as from about 5 to about 25° C., to form the reaction mixture. The reaction mixture may then be heated, such as to from about 35 to about 55° C., to form a reaction product mixture comprising compound 300. In some aspects, the reaction time to completion may be at least 6 hours, at least 12 hours, at least 18 hours, at least 24 hours, or more. The reaction may be deemed complete when the area % concentration by HPLC of compound 152 is less than 5, less than 2, less than 1, less than 0.5, or less than 0.1.

Compound 300 may be optionally purified. In some such aspects, the reaction product mixture may be admixed with water wherein the ratio of water volume to compound 320 starting material weight is about 3 L/kg, about 5 L/kg, about 10 L/kg, about 15 L/kg, or about 20 L/kg, and ranges thereof, such as from about 3 to about 20 L/kg, or from about 5 to about 15 L/kg. The temperature may suitably be from about 30 to about 50° C. and the admixture may be agitated for at least 0.25 hours, at least 0.5 hours or at least 1 hour. The admixture may be cooled, such as to from about 15 to about 35° C., and filtered through a filter media, such as diatomaceous earth. The filtrate may be allowed to separate into an aqueous phase and an organic phase, and the organic phase May be collected and optionally washed with water and brine. The organic phase may then concentrated, such as for instance to ratio of volume to compound 320 starting material weight of about 2 L/kg, about 3 L/kg, about 4 L/kg, or about 5 L/kg, and ranges thereof, such as from about 2 to about 5 L/kg or from about 2 to about 4 L/kg. An organic solvent (e.g., toluene or NMP) may be combined with the concentrated organic phase at a ratio of organic solvent to compound 320 starting material weight of about 1 to about 2 L/kg. The volume may be reduced, for instance, under vacuum and at a temperature below 40° C., to produce a solution of compound 300. In some aspects, the organic solvent is DCM and compound 300 is in solution in DCM.

In some aspects, compound 321 may be prepared from compound 330 wherein $R^{1a}$ and $R^{1b}$ are each independently selected from the group consisting of H and $C_{1-6}$ alkyl, $R^{2b}$ is selected from the group consisting of H and $C_{1-6}$ alkyl according to the following reaction scheme:

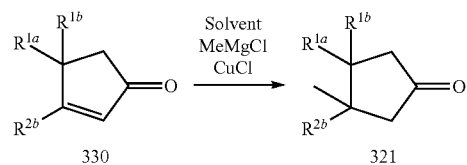

The method for preparing compound 321 comprises forming a reaction mixture comprising a polar aprotic solvent, methyl magnesium chloride, copper (I) chloride and compound 330. The reaction mixture is reacted to form a reaction product mixture comprising compound 321.

The polar aprotic solvent is as described elsewhere herein. In some aspects, the polar aprotic solvent is THF.

The reaction mixture may be formed under a $N_2$ blanket and/or with an $N_2$ purge. In some aspects, the polar aprotic solvent may be charged to a reactor and admixed with CuCl and MeMgCl. The ratio of polar aprotic solvent volume to compound 330 starting material weight is about 3 L/kg, about 5 L/kg, about 10 L/kg, about 15 L/kg, or about 20 L/kg, and ranges thereof, such as from about 3 to about 20 L/kg, or from about 5 to about 15 L/kg. The equivalent ratio of CuCl to compound 330 starting material is about 0.1:1, about 0.2:1, about 0.3:1, about 0.4:1 or about 0.5:1, and ranges thereof, such as from about 0.1:1 to about 0.5:1 or from about 0.1:1 to about 0.3:1. The equivalent ratio of MeMgCl to compound 330 starting material is about 0.05:1, about 0.1:1, about 0.015:1 about 0.2:1 or about 0.3:1, and ranges thereof, such as from about 0.05:1 to about 0.3:1 or from about 0.05:1 to about 0.15:1. The mixture is stirred at a temperature of from about −30 to about −10° C. followed by addition of compound 330 to the reactor while maintaining the temperature. Additional MeMgCl is added to the reactor at a temperature of from about −30 to about −10° C. wherein the equivalent ratio of the additional MeMgCl to compound 330 is about 0.9:1, about 1:1, about 1.1:1 about 1.2:1, about 1.3:1, about 1.4:1 or about 1.5:1, and ranges thereof, such as from about 0.9:1 to about 1.5:1 or from about 1:1 to about 1.2:1. A reaction product mixture comprising compound 321 in solution formed. In some aspects, the reaction time to completion may be at least 1 hour, at least 2 hours, at least 4 hours, at least 6 hours, or more. The reaction may be deemed complete when the area % concentration by HPLC of compound 330 is less than 5, less than 2, less than 1, less than 0.5, or less than 0.1.

Compound 321 may be isolated from the reaction product mixture. In some such aspects, the pH of the reaction product mixture may be adjusted to from about 3 to about 4 with an aqueous mineral acid solution, for instance 3 to 10 w/w % HCl. The resultant aqueous phase and organic phase (e.g., THF) comprising compound 321 in solution may be separated. The aqueous phase may be extracted with a non-polar solvent (e.g., MTBE) at a volume ratio of solvent to compound 330 starting material weight of from about 2 L/kg to about 10 L/kg or from about 3 L/kg to about 7 L/kg. The organic phases may be combined and washed with aqueous inorganic base (e.g., $NaHCO_3$) followed by a brine wash. The washed organic phase may then be dried with a drying agent, for instance over $Na_2SO_4$. The drying agent may be removed, such as by filtration or centrifugation. The organic phases may be concentrated to a volume ratio to compound 330 starting material weight of from about 3 to about 15 L/kg, such as about 5 L/kg or about 10 L/kg. Concentration may suitably be done at atmospheric pressure at from about 50 to about 70° C.

In some aspects, compound 321 may be purified by fractional distillation as follows. The combined organic phases or concentrated organic phases may be first distilled at a temperature of less than about 60° C. to remove a first (front) fraction predominantly comprising solvent. Distillation may continue to produce a compound 321 product fraction collected at a temperature of between 60° C. and 90° C. (P≤−0.09 MPa). In such aspects, the yield of compound 321 is at least 40% or at least 50% and the HPLC purity of compound 321 is at least 95 area %, at least 98 area % or at least 99 area % by HPLC. Distillation may optionally be continued to remove one or more additional fractions.

In some particular aspects, $R^{1a}$ and $R^{1b}$ are H, $R^{2b}$ is —CH$_3$, and compound 321 is the species of compound 120:

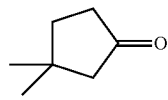

120 and
compound 330 is the species of compound 110:

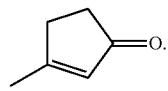

110

In some particular aspects, the solvent is THF, the mole ratio of methyl magnesium chloride to compound 110 in the reaction mixture is between 1:1 and 2:1, or from about 1.1:1 to about 1.4:1, and the mole ratio of copper (I) chloride to compound 110 in the reaction mixture is from about 0.1:1 to about 0.5:1, or from about 0.15:1 to about 0.25:1.

Figure 8:
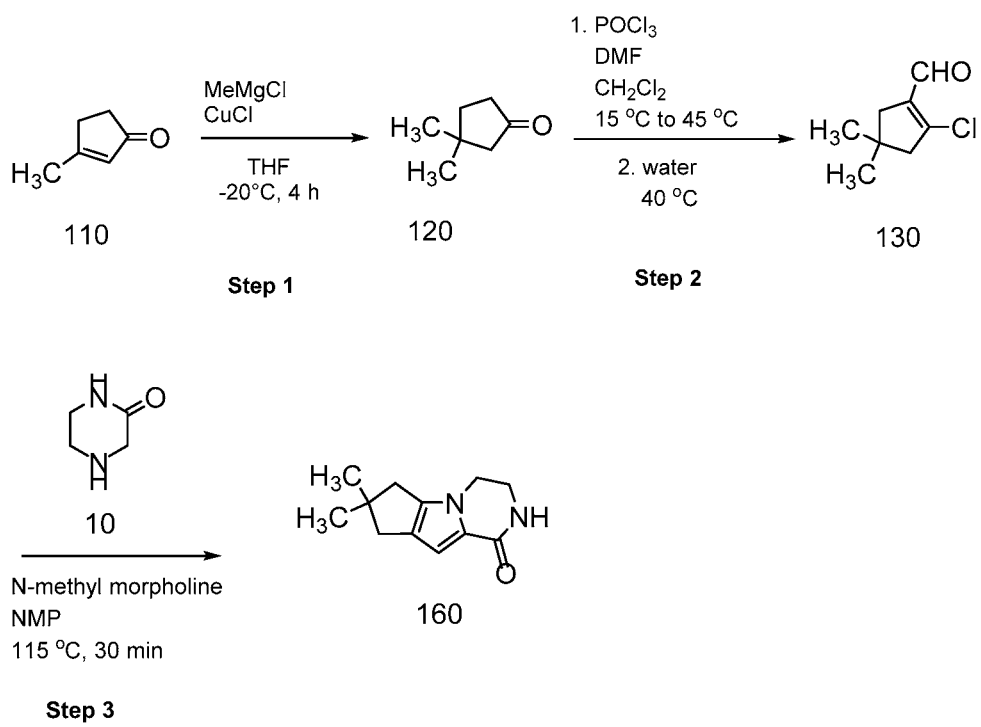
FIG. 8 shows a method for the preparation of compounds 120, 130 and 160.

In some particular aspects, compounds 130 and 160 may be prepared according to the method hereinbefore described and depicted in FIG. 8.

In some aspects of the invention, compound 320 may be purified by a solid ketone bisulfite adduct route. The purification method comprises forming a first reaction mixture comprising crude compound 320, an organic solvent that is not miscible with water (e.g., heptane), and an aqueous solution of sodium bisulfite, and reacting the first reaction mixture to form a first reaction product mixture comprising the solid ketone bisulfite adduct of compound 340:

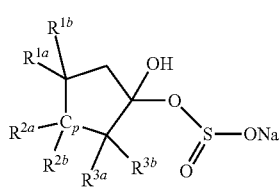

340 wherein $R^{1a}$, $R^{1b}$, $R^{2a}$, $R^{2b}$, $R^{3a}$ and $R^{3b}$ are as defined elsewhere herein. In some aspects, compound 340 is the species compound 121:

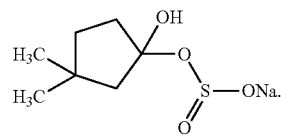

121

Compound 340 is isolated from the first reaction product mixture. A second reaction mixture is formed comprising isolated compound 340, water, a low boiling solvent that is not miscible with water, and sodium bicarbonate. In some aspects, the solvent is DCM. The second reaction mixture is reacted to form a second reaction product mixture comprising a first phase comprising the solvent and the predominant amount of purified compound 320 is in solution in the first phase, and a second phase comprising water. The first phase comprising the purified compound 320 is separated from the aqueous phase.

In such aspects, the pH of the reaction product mixture comprising crude compound 320 may be adjusted to less than 5 with an aqueous mineral acid solution, for instance, aqueous HCl providing about 1.2 to about 1.4 equivalent of HCl per equivalent of compound 320.

In the first reaction mixture, the pH-adjusted reaction product mixture may be combined with a solvent that is not miscible with water (e.g., hexane) wherein crude compound 320 is soluble in said solvent. In some aspects, the ratio of solvent volume to compound 320 weight of from about 5 L/kg to about 25 L/kg, from about 10 L/kg to about 20 L/kg, or from about 10 L/kg to about 15 L/kg. The ratio of water volume to the crude compound 320 weight in the first reaction mixture is from about 1:1 L/kg to about 10:1 L/kg, from about 1.5:1 L/kg to about 4:1 L/kg, or from about 2:1 L/kg to about 3:1 L/kg. The equivalent ratio of sodium bisulfate to compound 320 in the first reaction mixture is from about 2:1 to about 5:1 or from 3:1 to about 5:1.

The first reaction mixture is formed by combining the pH-adjusted reaction product mixture with the solvent that is not miscible with water with agitation at a temperature of from about 10 to about 30° C. The resulting admixture is combined with a filter aid (e.g., diatomaceous earth) and the solids are removed, such as by centrifugation or filtration. The filtrate is separated to form an organic phase comprising compound 320 and an aqueous phase. The organic phase is concentrated below at temperature of about 75° C. by reducing the volume to a ratio of total volume to compound 320 weight of from about 1.5 L/kg to about 4 L/kg, or from about 1.5 L/kg to about 2.5 L/kg. The reduced volume organic phase is cooled, for instance, to about 10 to about 30° C., optionally filtered, and combined with aqueous NaHSO$_3$ solution providing from about 2 to about 5 equivalents of NaHSO$_3$ per equivalent of compound 320 or from about 3 to about 4.5 equivalents of NaHSO$_3$ per equivalent of compound 320 to form a slurry comprising solid compound 340. Solid compound 340 is isolated, such as by filtration or centrifugation, and the collected solids are slurried in the solvent that is not miscible with water (e.g., hexane). The ratio of solvent volume to compound 340 weight is suitably from about 3 L/kg to about 13 L/kg, or from about 5 L/kg to about 9 L/kg. Solid compound 340 is isolated, such as by filtration or centrifugation. The isolated compound 340 solids are optionally washed with the low boiling solvent volume that is not miscible with water (e.g., DCM).

The second reaction mixture comprises a ratio of water volume to isolated solid 340 weight of from about 5:1 L/kg to about 15:1 L/kg, or from about 7.5:1 L/kg to about 10.5:1 L/kg. The ratio of water volume to the low boiling solvent volume that is not miscible with water (e.g., DCM) in the second reaction mixture is from about 1:1 to about 3:1 or from about 1.5:1 to about 2.5:1. The ratio of the volume of solvent that is not miscible with water and compound 340 weight is from about 2 L/kg to about 9 L/kg, from about 3 L/kg to about 7 L/kg, or from about 4 L/kg to about 6 L/kg. The equivalent ratio of sodium bicarbonate to compound 340 in the second reaction mixture is between 1:1 and 2:1, or from about 1.25:1 to about 1.75:1. In some aspects, the sodium bicarbonate is an aqueous solution of sodium bicarbonate.

The second reaction mixture is formed by combining the compound 340 solids with water and with agitation. The low boiling solvent that is not miscible with water is added and followed by addition of the solution of sodium bicarbonate to form a second reaction product mixture comprising compound 320. The resulting admixture may be combined with a filtration aid (e.g., diatomaceous earth) and the solids are removed from the admixture, such as by filtration or centrifugation. The filtrate or centrifugate is allowed to separate into an organic phase and an aqueous phase, and the phases are separated and collected. The aqueous phase may optionally be extracted with the low boiling solvent that is not miscible with water, and the organic phases are combined. The combined organic phase may be washed with brine. The washed combined organic phase may be concentrated at a temperature of less than about 70° C. to a total volume to compound 320 weight of from about 1.5 L/kg to about 4 L/kg or from about 1.5 L/kg to about 2.5 L/kg and comprises compound 320 in solution. The assay of the solution is suitably from about 30% to about 50%, from about 35% to about 45%, or about 40%. The yield of compound 320 is at least 50%, at least 60% or at least 70%.

The purification scheme for the solid ketone bisulfite adduct may also be used to purify compounds 120 and 321. In some particular aspects, compounds 130 and 160 may be prepared according to the method hereinbefore described and depicted in FIG. 9.

In some aspects of the invention, a sub-genus of compound 300, designated as compound 301 in the below reaction scheme, may be prepared from a trimethyl silyl intermediate of compound 320, designated as compound 335 in the below reaction scheme. The reaction scheme is as follows:

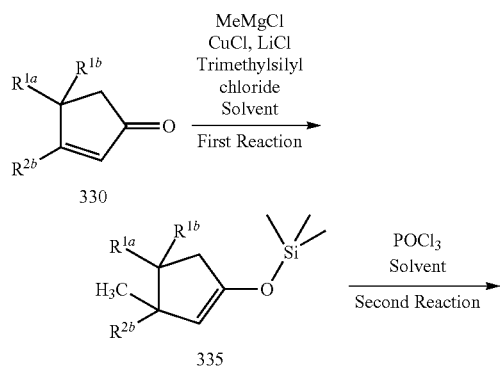

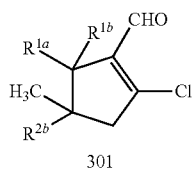

The method for preparing compound 301 comprises forming a first reaction mixture comprising a first polar aprotic solvent, methyl magnesium chloride, copper (I) chloride, lithium chloride, chlorotrimethylsilane (TMSCl), and compound 330. Compound 301 is a sub-genus of compound 300 where $R^{1a}$ and $R^{1b}$ are each independently selected from the group consisting of H and $C_{1-6}$ alkyl, $R^{2b}$ is selected from the group consisting of H and $C_{1-6}$ alkyl, $R^{3a}$ and $R^{3b}$ are each H, and p is 1. In some aspects, $R^{1a}$ and $R^{1b}$ are each H and $R^{2b}$ is —$CH_3$. In some aspects, compounds 330, 335 and 305 are of the species 110, 122 and 130 respectively:

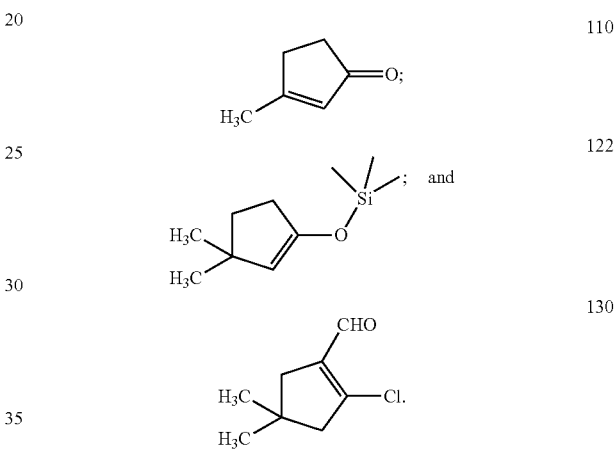

The first reaction mixture is reacted to form a first reaction product mixture comprising compound 335. The first reaction product mixture is quenched with a first quenching agent in aqueous solution and a non-polar water-immiscible solvent is added to the quenched reaction product mixture. Alternatively, the first reaction mixture is quenched with methanol as the first quenching agent, followed by a second quenching agent in aqueous solution and a non-polar water-immiscible solvent is added to the quenched reaction product mixture. The phases are separated and an organic phase comprising the predominant amount of compound 335 is collected and concentrated to obtain compound 335 in solution. A second reaction mixture comprising a second polar aprotic solvent, phosphorous oxychloride, and the solution of compound 335 is formed. The second reaction mixture is reacted to form a second reaction product mixture comprising compound 301. The second reaction product mixture is quenched with a third quenching agent in aqueous solution. The phases are separated and an organic phase comprising the predominant amount of compound 301 in solution is collected.

The first and second polar aprotic solvents are as described elsewhere herein. In some aspects, the first polar aprotic solvent is THF. In some aspects, the second polar aprotic solvent is DMF. In some aspects, the first quenching agent is ammonium chloride. In some aspects, the first quenching agent is methanol. In some aspects, the first quenching agent is methanol and the second quenching agent is ammonium chloride. In some aspects, the third quenching agent is potassium phosphate.

In some aspects, the first reaction mixture comprises from about 0.25 to about 2 moles per liter of compound 330, or from about 0.5 to about 1.1 moles per liter of compound 330. In some other aspects, the ratio of the volume of the first polar aprotic solvent volume to compound 330 weight is about 3 L/kg, about 5 L/kg, about 5 L/kg, about 7 L/kg, about 9 L/kg, or about 11 L/kg, and ranges thereof, such as from about 3 to about 11 L/kg, or from about 5 L/kg to about 9 L/kg. MeMgCl is present in stoichiometric excess as compared to compound 330. In some aspects, MeMgCl is in solution in THF, such as a 3M solution. In some aspects, the mole ratio of MeMgCl to compound 330 is between 1:1 and 1.5:1, or is from about 1.1:1 to about 1.3:1. TMSCl is present in stoichiometric excess as compared to compound 330. In some aspects, the mole ratio of TMSCl to compound 330 is between 1:1 and 1.2:1, or from about 1.01:1 to about 1.1:1. The mole ratio of CuCl to compound 330 is from about 0.05:1 to about 0.2:1, or from about 0.05:1 to about 0.15:1. The mole ratio of LiCl to compound 330 is from about 0.05:1 to about 0.2:1, or from about 0.07:1 to about 0.15:1.

In some aspects, the second reaction product mixture comprises from about 0.5 to about 2 moles per liter or from about 0.7 to about 1.3 moles per liter compound 335. The mole ratio of phosphorous oxychloride to compound 335 is from about 1.5:1 to about 3.1:1, or from about 2.1:1 to about 2.6:1.

In the first reaction, in some aspects, CuCl, LiCl, and the first polar aprotic solvent may be combined in an $N_2$ atmosphere in a reactor at a temperature of from about 10 to about 35° C. and cooled to from about −10 to about 10° C. Compound 330 and TMSCl are added to the reactor at from about −10 to about 10° C. MeMgCl is added to the reactor at from about −10 to about 10° C. A first reaction product mixture comprising compound 335 is formed. In some aspects, the reaction time to completion may be at least 0.5 hours, at least 1 hour, at least 2 hours, at least 4, or more. The reaction may be deemed complete when the area % concentration by HPLC of compound 330 is less than 5, less than 2, less than 1, less than 0.5, or less than 0.1. The reaction is quenched, such as with an aqueous ammonium chloride solution wherein the equivalent ratio of ammonium chloride to compound 330 is greater than 1:1, about 1.1:1, about 1.2:1 or about 1.3:1. The ratio of ammonium chloride solution volume to compound 330 is from about 2:1 to about 10:1 L/kg, or from about 3:1 to about 7:1 L/kg. Alternatively, the reaction is first quenched with methanol, wherein the equivalent ratio of methanol to compound 330 is about 0.25:1, about 0.5:1, or about 1:1. After the first quench with methanol, the reaction is further quenched with an aqueous ammonium chloride solution wherein the equivalent ratio of ammonium chloride to compound 330 is greater than 1:1, about 1.1:1, about 1.2:1 or about 1.3:1. The ratio of ammonium chloride solution volume to compound 330 is from about 2:1 to about 10:1 L/kg, or from about 3:1 to about 7:1 L/kg.

After the above quenching step(s), organic and aqueous phases are separated and collected. The organic layer comprises compound 335 in solution and may optionally be washed with brine. The optionally washed organic layer may be concentrated until the ratio of the distillate volume collected to compound 330 weight is from about 8 L/kg to about 10 L/kg. The concentrated first reaction product mixture may be diluted with a non-polar solvent (e.g., toluene) wherein the ratio of the added non-polar solvent volume to compound 330 weight is from about 1 L/kg to about 3 L/kg. In such aspects, the diluted mixture may concentrated to remove an approximate volume of the added non-polar solvent to produce a solution of compound 335. The compound 335 assay in the solution is from about 40 w/w % to about 60 w/w %, or from about 45 w/w % to about 55 w/w %. The yield of compound 335 based on compound 330 is at least 60%, at least 70% or at least 80% and the HPLC purity of compound 335 is at least 85 area % or at least 90 area % by HPLC.

In the second reaction, the solution from the first reaction is diluted with the non-polar solvent to achieve a compound 335 assay of from about 25 to about 45 w/w % or from about 30 to about 40 w/w % or about 35 w/w %. In some aspects, the non-polar solvent is toluene. Water is added in an equivalent weight ratio of about 0.4:1 relative to compound 330. Water is added in an equivalent weight ratio of about 0.4:1 relative to compound 330. A first $POCl_3$ addition may be done wherein the equivalent ratio of $POCl_3$ to compound 330 weight is from about 0.2:1 to about 0.4:1 or about 0.3:1 and wherein the temperature is from about 5 to about 35° C. DMF is added after $POCl_3$ at an equivalent ratio to compound 330 of from about 1.5:1 to about 3:1 or from about 1.5:1 to about 2.5:1. A second $POCl_3$ addition is done wherein the equivalent ratio of $POCl_3$ to compound 330 weight is from about 1.5:1 to about 2.5:1 or about 2:1, and the mixture is heated to from about 50 to about 70° C. to form a second reaction product mixture comprising compound 301. In some aspects, the reaction time to completion may be at least 2 hours, at least 4 hours, at least 8 hours, at least 12 hours, or more. The reaction may be deemed complete when the area % concentration by HPLC of compound 330 is less than 5, less than 2, less than 1, less than 0.5, or less than 0.1. The reaction product mixture is combined with an aqueous potassium phosphate solution providing an equivalent ratio of potassium phosphate to compound 330 is from about 1.2:1 to about 2:1 or from about 1.4:1 to about 1.8:1. The ratio of potassium phosphate solution volume to compound 330 weight is from about 3 to about 12 L/kg or from about 6 to about 9 L/kg. Organic and aqueous phases are formed that are separated and collected. The organic layer is washed with potassium phosphate solution and water to obtain a washed organic phase (e.g., toluene) comprising compound 301 in solution and having a pH in excess of 7. The organic phase is filtered to generated compound 301 in solution (e.g., toluene). The yield of compound 301 based on compound 330 is at least 70% or at least 75%, and the purity of compound 301 is at least 85% or at least 88% by HPLC.

The purification scheme for the trimethylsilyl intermediate may be used to purify compounds 120 and 321. In some particular aspects, compounds 130 and 160 may be prepared according to the method herein before described and depicted in FIG. 10.

Also provided herein is a method of preparing compound 200, stereoisomers thereof, geometric isomers thereof, tautomers thereof, and salts thereof,

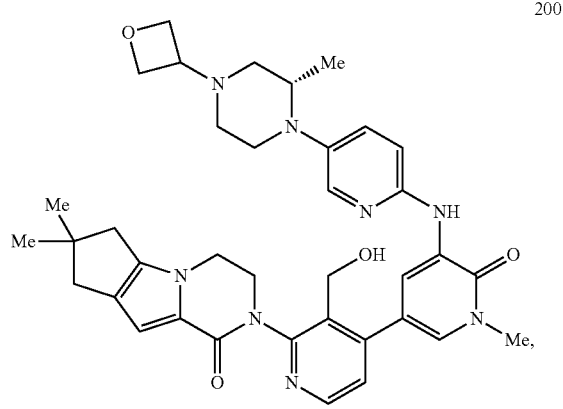 [SMILES: C[C@H]1CN(C2COC2)CCN1c1ccc(Nc2cc(-c3ccnc(N4CCn5c(cc6c5CC(C)(C)C6)C4=O)c3CO)cn(C)c2=O)nc1]

200 the method comprising:
(i) (1) forming a first reaction mixture comprising compound 170, a reducing agent, a base and a solvent, to reduce the aldehyde moiety of compound 170 to form compound 171, and
(2) isolating compound 171 from the first product mixture,
(ii) (1) forming a second reaction mixture comprising compound 171, compound 182, a palladium catalyst, a solvent system comprising water, and a base, to form compound 200, and
(2) isolating compound 200 from the second product mixture, according to the following scheme:

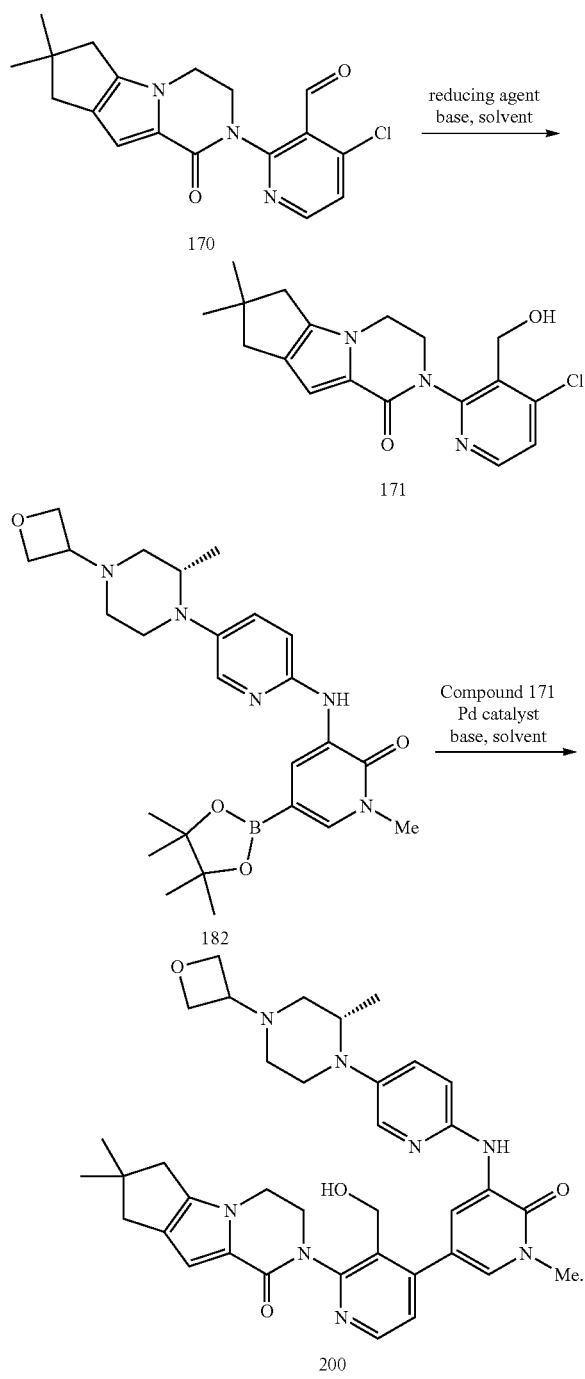

In some aspects, the reducing agent in step (i) is NaBH$_4$. In some aspects, the base in step (i) is K$_2$HPO$_4$. In some aspects, the solvent in step (i) is THF. In some aspects, the Pd catalyst in step (ii) is Pd(PCy$_3$)$_2$. In some aspects, the base in step (ii) is K$_3$PO$_4$, Et$_3$N or Di-isopropylethylamine. In some aspects, the equivalent ratio of the Pd catalyst to compound 171 is less than 0.05:1. In some aspects, the ratio of compound 182 to compound 171 is greater than 1:1.

Also provided herein is a compound having the structure:

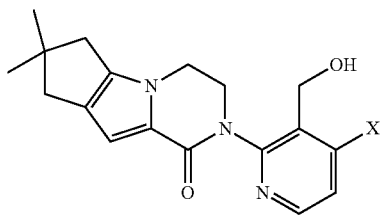

wherein X is selected from the group consisting of Cl, Br, and I. In some embodiments, X is Cl. In some embodiments, X is Br.

EXAMPLES

The Figures and Examples provide exemplary methods for preparing the disclosed compounds; those skilled in the art will appreciate that other synthetic routes may be used to synthesize the compounds. Although specific starting materials and reagents are depicted and discussed in the Figures and Examples, other starting materials and reagents may be substituted to provide a variety of derivatives and/or reaction conditions. In addition, many of the described and exemplary methods may be further modified in light of this disclosure using conventional chemistry well known to those skilled in the art.

In the Examples, equivalents and equivalent ratios are based on the referenced starting material for each reaction. Volume per weight values, such as L/kg and mL/g, refer to a volume of a liquid component based on the weight of the referenced starting material for each reaction.

Analytical Methods

High pressure liquid chromatography (HPLC) may be performed as follows.

Examples 1, 2, 10B and 10E (final compound). HPLC Column: Waters XSelect CHS C18 (150 mm*3.0 mm*3.5 μm). Mobile Phase A: 10 mM ammonium formate pH 3.7. Mobile Phase B: CH$_3$CN. Flow Rate: 1.0 mL/min. Injection Volume: 5.0 uL to 10.0 uL. Column Temperature: 45° C. UV Detection Wavelength: 245 nm. Diluent: 30:70 (v/v) CH$_3$CN/H$_2$O.

Examples 5 to 8. Column: Waters Atlantis T3 (4.6*150 mm 3 μm). Mobile Phase A: 10 mM ammonium formate pH 3.7. Mobile Phase B: CH$_3$CN. Flow Rate: 1.0 mL/min. Injection Volume: 2.0 uL. Column Temperature: 45° C. UV Detection Wavelength: 315 nm. Diluent: CAN.

Example 10C. Column: (1) Agilent PLRP-S 100A, 150 mm×4.6 mm, 3 μm or (2) Agilent PLRP-S 100A, 250 mm×4.6 mm, 5 μm. Mobile phase A: 10 mM aqueous NaOH. Mobile phase B: acetonitrile. Flow Rate: 1.0 mL/min. Injection Volume: 1.0 uL. Column temperature: (1) 20° C.; (2) 15° C.

Example 1 (10D in-process test), example 10E (compound 190 in process test) and borane adduct in process test. Column: ACE Excel C18 HL (50×3 mm, 3 μm). Mobile Phase A: Water with 0.05% TFA. Mobile Phase B: CH$_3$CN with 0.05% TFA. Flow Rate: 1.0 mL/min. Injection Volume: 2.0 uL. Column Temperature: 35° C. UV Detection Wavelength: 220 nm. Diluent: Methanol.

Example 10D final compound 190. Column: Agilent Poroshell EC-C18 (150×3 mm, 2.7 μm). Mobile Phase A: 10 mM ammonium formate in water. Mobile Phase B: CH₃CN. Flow Rate: 0.5 mL/min. Injection Volume: 5.0 uL. Column Temperature: 30° C. UV Detection Wavelength: 245 nm.

Liquid chromatograph mass spectrometry (LCMS) may be performed as follows. Column: XDB-C18 4.6 mm×50 mm, 1.8 μm. Mobile Phase A: Water/0.05% TFA. Mobile Phase B: CH₃CN/0.05% TFA. Flow Rate: 1.2 mL/min. Injection Volume: 10.0 uL. Column Temperature: 40° C. Diluent: 30:70 (v/v) CH₃CN/H₂O. Interface Type: ES-API+. Drying Gas Temp: 250° C. Nebulizer Pressure: 35 psig. Drying Gas Flow: 13 L/min. Capillary Voltage: 3000 V. Scan Range: 150-600 m/z.

Gas chromatography (GC) may be performed as follows. An Agilent 7890A series GC system with an Agilent HP-5 (30 m*0.32 mm*0.25 μm) column. Flow rate: 2.0 mL/min. Injection volume: 10.0 uL. Carrier gas: N₂. Diluent: methanol.

Mass spectrometry (MS) may be performed using a (1) Sciex 15 mass spectrometer in ES+ mode, or (2) Shimadzu LCMS 2020 mass spectrometer in ESI+ mode. Mass spectra data generally only indicates the parent ions unless otherwise stated. MS or HRMS data is provided for a particular intermediate or compound where indicated.

Nuclear magnetic resonance spectroscopy (NMR) may be performed using any suitable instrument, including, but not limited to, a (1) Bruker AV III 300 NMR spectrometer, (2) Bruker AV III 400 NMR spectrometer, or (3) Bruker AV III 500 NMR spectrometer, and referenced to tetramethylsilane. NMR data is provided for a particular intermediate or compound where indicated.

Example 1

7,7-dimethyl-3,4,7,8-tetrahydro-2H-cyclopenta[4,5]pyrrolo[1,2-a]pyrazin-1(6H)-one (Compound 160) was prepared according to the reaction scheme in FIG. 8.

In a first step, compound 120 was prepared from compound 110 as follows:

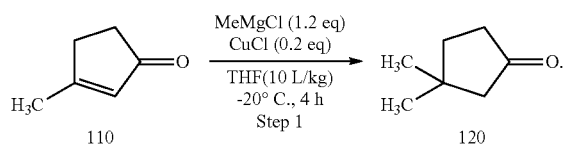

Three batches of compound 120 were separately prepared, with each batch based on 53.3 kg (554.6 mol, 1.0 equiv) of compound 110 (3-methylcyclopent-2-en-1-one) starting material.

For each batch, a dry 1000 L jacket reactor equipped with an agitator, a temperature probe and a nitrogen inlet, was charged THF (458.6 kg) under a N₂ atmosphere. CuCl (11.2 kg, 113.1 mol, 0.2 equiv), was charged to the reactor over 10 minutes with stirring. The reactor was cooled to −20±5° C. and MeMgCl in THF (3M, 18.7 kg, 0.1 equiv) was added to the reactor while maintaining the temperature at −20±5° C. The mixture was stirred for 15 minutes followed by addition of 3-methylcyclopent-2-enone (53.3 kg, 554.6 mol, 1.0 equiv) to the reaction mixture while maintaining the temperature at −20±5° C. The remaining MeMgCl (3M, 203.2 kg, 1.1 equiv) was charged, again maintaining the temperature at −20±5° C. The addition was complete in 2.5 hours. The reaction mixture was stirred at −20±5° C. for 2 hours. The reaction completion was confirmed by GC with the starting material concentration of less than 4%.

Compound 120 (3,3-dimethylcyclopentan-1-one) was isolated from the reaction product mixture as follows. Aqueous HCl solution (6% w/w, 485.3 kg) was added to the reaction product mixture slowly over 1.5 h to adjust the pH to 3 to 4. The mixture was stirred for a further 30 minutes. The THF phase was separated and transferred to another vessel. The aqueous phase was extracted with MTBE (202.7 kg). The MTBE phase separated and combined with the THF phase. The combined organic layer was washed with aqueous NaHCO₃ (26.7 kg, water 293.3 kg), followed by brine (NaCl 117.3 kg, water 522.6 kg). The organic layer was dried over Na₂SO₄ (144.0 kg) for 4 hours, followed by removal of the Na₂SO₄ by centrifugation. The solution was concentrated (at 1 atm) between 50 and 70° C. to a final concentration of 55 to 65 L.

The concentrated solution of each batch were combined and transferred to 20 L reaction flask equipped with a condenser for distillation. By a 3-stage fractional distillation: (1) solvents were removed first (front fraction); (2) compound 120 was removed second in a major distillation fraction (internal temperature of less than 110° C.); and (3) a last distillation fraction. A residue remained after removal of the last distillation fraction. The major distillation fraction, collected between 60-90° C. (P≤−0.09 MPa), afforded product compound 120 as a colorless oil. The isolated product contained 81.5 kg of compound 120, with a 43.6% isolated yield, and 98.6% purity by HPLC. The compound 120 assay yield of the front fraction was 0.2%, the compound 120 assay yield of the last distillation fraction was 2.0%, and the residue contained 0.9% compound 120. The major component identified in the residue was of the structure wherein the concentration was 11.5 A % by HPLC:

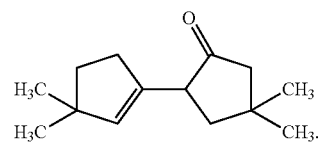

In a second step, compound 130 was prepared from compound 120 in four separate batches as follows:

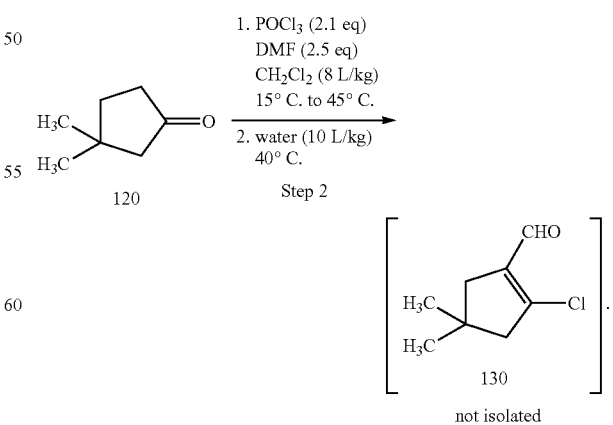

For each batch, a 500 L reactor was charged with DCM (287.3 kg, 8 L/kg) and N,N-dimethylformamide (44.0 kg, 602.1 mol, 2.5 equiv) under a N₂ atmosphere. The reaction mixture was cooled to 13±5° C. and POCl₃ (77.5 kg, 505.4 mol, 2.10 equiv) was added dropwise maintaining the temperature at 13±5° C. After addition was complete, the mixture was stirred for 1 hour at 13±5° C. Compound 120 (3,3-Dimethylcyclopentan-1-one) (27.0 kg, 240.6 mol) was charged to the reaction mixture dropwise maintaining the temperature at 13±5° C. After addition was complete, the mixture was stirred for 1 hour at 20±5° C. The reaction was then heated to 45±5° C. and stirred for 18-24 hours. The reaction completion was confirmed by GC with compound 120 concentration of less than 5%. The reaction mixture was cooled to 25±5° C.

For each batch, a solution of compound 130 (2-chloro-4,4-dimethylcyclopent-1-ene-1-carbaldehyde) was generated from the reaction product mixture as follows. A 1000 L reactor was charged with water (270.0 kg, 10 L/kg) and heated to 40±5° C. The reaction product mixture was added dropwise while maintaining the temperature at 40±5° C. Once addition was complete, the mixture was stirred for 30 minutes at 40±5° C. The reaction mixture was cooled to 25±5° C., and filtered through a pad of Celite®. The organic phase was separated and washed with water (108.0 L×2). The organic phase was then washed with brine (108.0 L), and the organic layer was concentrated to a total volume of 3 L/kg under vacuum below 40° C. NMP (27.8 kg, 1 L/kg) was charged and the mixture, and the mixture was concentrated to 54 L under vacuum below 40° C. The residue was cooled to 25±5° C. to afford crude compound 130 in NMP.

In a third step, compound 160 was prepared from compounds 130 and 10 as follows in four separate batches as follows:

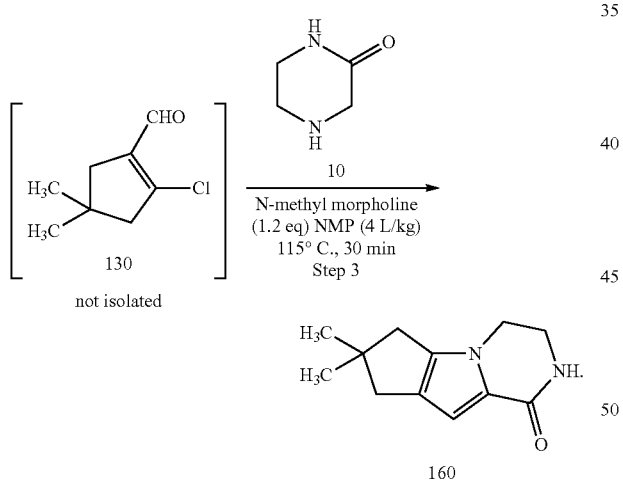

For each batch, a 300 L reactor was charged with NMP (83.2 kg, 3 L/kg), 4-methylmorpholine (29.2 kg, 288.8 mol, 1.2 equiv) and compound 10 (piperazin-2-one) (21.1 kg, 211.8 mol, 0.88 equiv) under a N₂ atmosphere. The reaction mixture was heated to 115±5° C. The solution of crude compound 130 in NMP was added dropwise maintaining the temperature at 115±5° C. The reaction mixture was stirred for 30 minutes at 110±5° C. The reaction completion was confirmed by GC with compound 160 concentration of no more than 5%.

For each batch, solid compound 160 (7,7-dimethyl-3,4,7,8-tetrahydro-2H-cyclopenta[4,5]pyrrolo[1,2-a]pyrazin-1(6H)-one) was obtained as follows. The reaction product mixture was cooled to 90±5° C., and water (135.0 kg, 5 L/kg) was then charged. The mixture was then further cooled to 60±5° C. To a separate 500 L reactor was charged water (135.0 kg, 5 L/kg), followed by addition of the reaction product mixture. The mixture was cooled to 25±5° C. and stirred for at least 3 hours at 25±5° C. Solid compound 160 was collected by centrifuge filtration. The collected solids were slurried in acetone (64.8 kg, 3 L/kg) for at least 3 hours at 25±5° C. The solid was collected by centrifuge filtration to afford wet crude compound 160 (30.1 kg).

The four batches of solid crude compound 160 were combined and slurried in heptane, isolated, and dried. The structure of compound 160 was identified by LCMS and as having a molecular weight of 206.32. The total compound 160 yield for steps 2 and 3 was 75.8 kg, the isolated yield for steps 2 and 3 was 51.1% and the purity was 98.5 A % by HPLC. The primary impurity was identified by LCMS as the dimer below having a molecular weight of 420.55 with a concentration of 1 Area %:

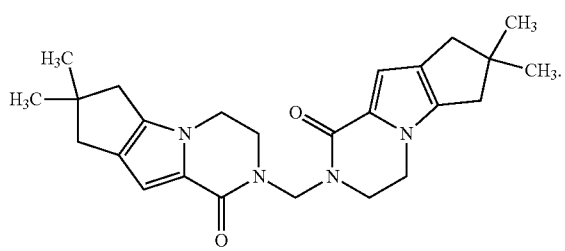 [SMILES: CC1(C)Cc2cc3n(c2C1)CCN(CN1CCn2c(cc4c2CC(C)(C)C4)C1=O)C3=O]

Example 2

Figure 9:
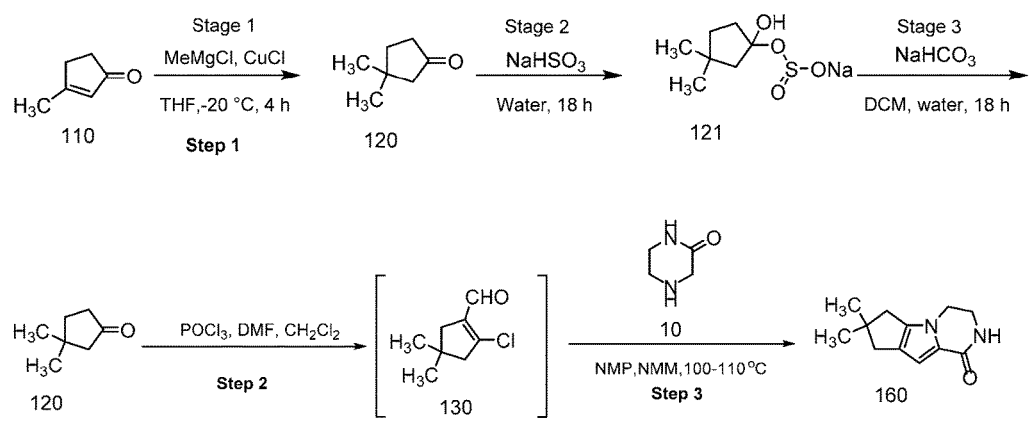
FIG. 9 shows a method for the preparation of compounds 120, 121, 130 and 160.

Compound 160 was prepared according to the reaction scheme in FIG. 9.

In a first step, compound 120 was prepared from compound 110 as follows:

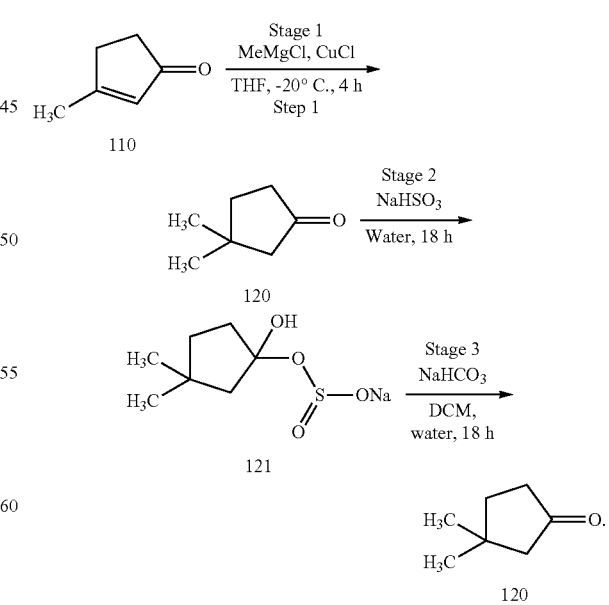

THF (1352 L, 8 volumes) was charged to a reactor under nitrogen and start stirring. Copper(I) chloride (35.49 kg, 0.2 eq) was charged to the reactor and the contents were cooled to −20±5° C. 59.15 kg of methyl magnesium chloride (22% in THF, 3 molar) (0.1 eq) was charged drop-wise to the reaction mixture while maintaining the temperature at −20±5° C. The contents of the reactor were stirred for 15 min at −20±5° C. 169.5 kg (1.0 eq) of Compound 110 (3-methylcyclopent-2-en-1-one) was charged to the reactor at −20±5° C. and the contents were stirred for 15 min at −20±5° C. 657.41 kg methylmagnesium chloride (22% in THF, 3M) (1.1 eq) was added dropwise at −20±5° C. to the reactor and the contents were stirred at −20±5° C. for at least 2 h. The reactor contents were sampled every 1 h and analyzed by GC until the concentration of compound 110 was no more than 4%.

The reaction product mixture was combined with 676 L HCl aqueous solution (4V, 1.3 eq HCl) while maintaining the temperature at 5±5° C., and the contents were stirred for an additional 30 min. To the reactor were then charged 2197 L hexane (13V) and 243 Kg NaCl, and the mixture was warmed to 20±5° C. and stirred for 1 h. 101 kg Celite was charged to the reactor and stirred for 30 min. The mixture was centrifuged and the collected solid compound 120 was washed with 169 L hexane. The filtrate was held for at least 30 minutes and separated. The organic phase was concentrated to about 338 L (2V) at a temperature below 75° C. and at normal pressure. The concentrated organic phase was cooled to 20±5° C. and filtered for form concentrated crude compound 120.

In a separate reactor, 845 L water (5V) was combined with 690 Kg NaHSO₃ (3.77 eq) with stirring. The concentrated crude compound 120 was charged to the reactor at 25±5° C. and the contents were stirred for 18 h at 25±5° C. Solid compound 121 was collected by centrifugation and was slurried in 1183 L hexane (7V) for at least 10 h at 25±5° C. The mixture was centrifuged and the collected solid compound 121 was washed with 338 L DCM (2V).

In a separate reactor, 1690 L water (10V) was combined with the solid compound 121 and stirred for 30 minutes. 845 L DCM (5V) was charged to the reactor. 221.8 Kg NaHCO₃ (1.5 eq) was charged to the reactor in portions at 25±5° C. and the contents were stirred for 18 h at 25±5° C. to form compound 120 in solution. 20 kg Celite was charged to the reactor with mixing and the reactor contents were centrifuged. The centrifugate was held for at least 3 h and a formed emulsion. The emulsion was separated to form an organic phase and an aqueous phase. The aqueous phase was extracted with 169 L DCM (1V) and the organic phases were combined. The combined organic phases were further combined with 338 L brine (2V), and an emulsion occurred. The emulsion was stirred for at least 30 mins and allow to sit for at least 3 h to separate into phases. The phases were separated. The organic phase was concentrated to about 2V at no more than 70° C. under normal pressure to yield 313.5 kg DCM solution comprising compound 120. The concentrated organic phase was cooled to 20±5° C. The concentrated solution contained 41.1% compound 120 as analyzed by GC for a total yield of 64.6%. The compound 120 purity was from 99.2 to 99.7 area % by HPLC.

In a second step, compound 130 was prepared from compound 120 as follows:

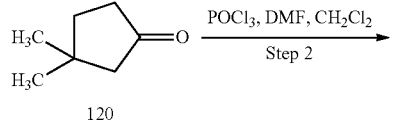

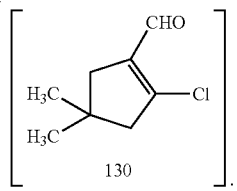

A reactor was prepared by reducing the pressure to ≤0.08 MPa and then purging with nitrogen to atmosphere. The preparation was repeated three times. The reactor was charged with 399 kg of DCM (4.0V) and 163 kg of DMF (2.5 eq) with stirring and cooling to 13±5° C. The reactor was charged with 287 kg of POCl₃ (2.1 eq) dropwise at 13±5° C. and stirred for 1 h at temperature. The reactor was then charged with 100 kg of compound 120 solution (1.0 eq) dropwise at 13±5° C. and stirred at 20±5° C. for 1 h followed by heating to 42±3° C. After 20 hours at 42±3° C. the content of compound 120 in the reaction product mixture as determined by GC was no more than 2.0%. The reaction product mixture was cooled to below 30° C. The reactor was charged with 285 kg of DMF (3.0V) and stirred for 10 min.

A separate reactor was charged with 1000 kg of purified water (10V) and heated to 40±3° C. The admixture of the reaction product mixture and DMF were charged dropwise to the reactor containing the water at 40±3° C. and the contents were stirred for at least 30 min after quenching the solution. The quenched reaction product mixture was cooled to 25±5° C., charged with 40 kg of Celite (0.4 w/w), further charged with 399 kg of DCM (3.0V), and stirred for at least 30 min. The mixture was centrifuged and the collected solids were washed with 133 kg DCM (1.0V). The centrifugate was stirred for at least 30 min and allowed to settle for at least 30 min. The phases were separated and the organic phase was collected. The aqueous phase was extracted with 532 kg DCM (4.0V), the DCM extract was combined with the collected organic phase, and the combined organic phases were washed with 400 kg H₂O (4.0V). The phases were separated and the organic phase was washed with 400 kg H₂O (4.0V). The washed organic phase was further washed with 400 L brine (4.0V). The phases were separated and the organic phase was concentrated to 3±0.5V. 130 kg of petroleum ether (2.0V) was added to the concentrated organic phase that was then concentrated to 3±0.5V. This was repeated two more times. The concentrated organic phase was charged with 103 kg of NMP (1.0V) that was then concentrated to 2.5±0.5V to yield a solution of compound 130.

In a third step, compound 160 was prepared from compound 130 as follows:

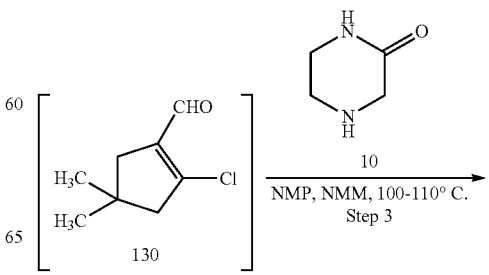

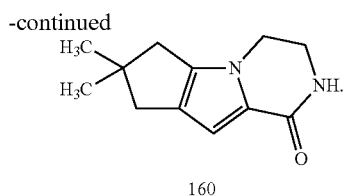

160

A reactor was prepared by reducing the pressure to ≤0.08 MPa and then purging with nitrogen to atmosphere. The preparation was repeated three times. The reactor was charged with 309 kg of NMP (3.0V) and 108 kg of N-methylmorpholine (1.2 eq) with stirring. The reactor was then charged with 79 kg of piperazin-2-one (0.88 eq) and heated to 105±5° C. The solution of compound 130 from the second step was charged to the reactor at 105±5° C. After 30 minutes of reaction at 105±5° C., the content of compound 130 in the reaction product mixture was no more than 5% by GC. The reaction product mixture was cooled to about 90±5° C. and 1000 kg of water (10V) was charged to the reactor. The reactor contents were cooled to 15±5° C. and were stirred for at least 3 h at 15±5° C. The reactor contents were centrifuged and the collected solids were slurried in 1000 kg water (10V) for at least 3 h at 20±5° C. The slurry was centrifuged and the collected solids were slurried with 240 kg acetone (3V) for at least 3 h at 25±5° C. The slurry was centrifuged and the collected solids were washed with 80 kg acetone (1V). The washed solids were dried in a vacuum oven at 35±5° C.

The isolated yield for steps 2 and 3 was 57.3% and the purity for steps 2 and 3 was 99.9 area % by HPLC.

As compared to Example A, it is believed that removal of DCM by solvent switch reduced formation of the dimer impurity.

Formation of the ketone bisulfide adduct of compound 121 allowed for isolation of the adduct as a solid by filtration thereby leaving dark impurities in the mother liquor and provide for a purity of compound 120 on the order of 99% as measured by GC. Furthermore, the yield in the step for forming compound 120 was increased to 64.6%.

Example 3

Figure 10:
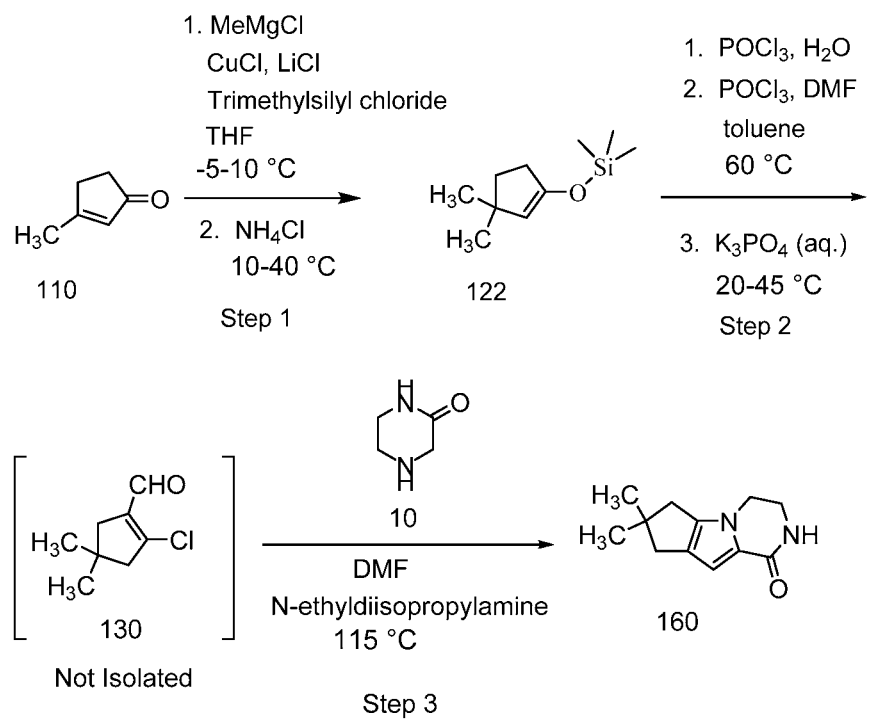
FIG. 10 shows a method for the preparation of compounds 122, 130 and 160.

Compound 160 was prepared according to the reaction scheme in FIG. 10.

In a first step, compound 122 was prepared from compound 110 as follows:

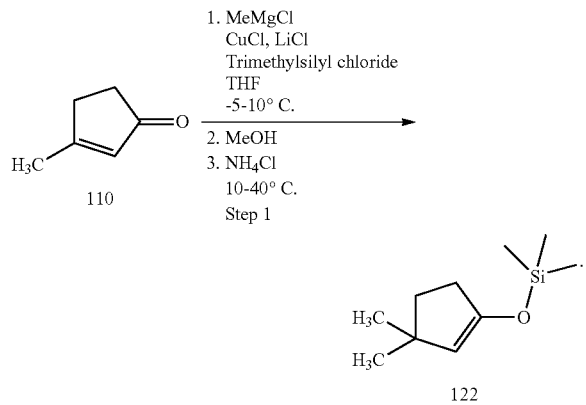

Copper (I) chloride (2.58 g, 0.05 eq) and lithium chloride (2.21 g, 0.1 eq) were dissolved in THF (325 mL, 6.5 relative volume) in a reaction reactor under an inert atmosphere at a temperature of 15-30° C. followed by cooling to −5 to 5° C. Compound 110 (50.0 g, 1.0 eq) and chloromethylsilane (59.33 g, 1.05 eq) were added to the reactor via an addition funnel at −5 to 10° C. Methylmagnesiumchloride (210.76 g, 1.2 eq.) was added to the reactor via an addition funnel at −5 to 10° C. followed by a funnel rinse with THF (25 mL, 0.5 rel. vol.) to the reactor. A suspension formed that was stirred for 0.5 to 1 h at −5 to 10° C. The concentration of compound 110 was no more than 2.0 area % by HPLC.

The suspension was warmed to 15 to 20° C. and stirred for 15 to 30 minutes. Subsequently, methanol (4.16 g, 0.25 eq.) was added at 15 to 20° C. within at least 20 minutes and stirred for at least another 15 minutes The suspension was transferred to a quench reactor and was quenched at 10 to 40° C. onto 12 w/w % ammonium chloride solution (250 mL, 5 rel. vol., 1.1 eq). The reaction reactor was rinsed with toluene (100 mL, 2.0 rel. vol.) into the quench reactor to form an emulsion that was stirred for 30 minutes followed by temperature adjustment to 20 to 30° C.

The phases were separated to obtain organic layer 1 (612.2 g, 695 mL) and aqueous layer 1 (325.1 g, 275 mL). Organic layer 1 was washed with 20 w/w % brine (100 mL, 2 rel. vol.) and the phases were separated to form organic layer 2 (608.6 g, 690 mL) and aqueous layer 2 (114.1 g, 102 mL). Organic layer 2 was concentrated at 65 to 90° C. and 800 to 300 mbar to about 500 mL distillate (10 rel. vol.). The residue was diluted with toluene (100 mL, 2.0 rel. vol.) and concentrated at 65 to 90° C. and 700 to 200 mbar until about 100 mL distillate (2 rel. vol.) is collected. Compound 122 is present in solution in toluene. The solution assay was 53 w/w % compound 122, the yield of compound 122 was 80%, and the purity of compound 122 by HPLC was 89 area %.

In a second step, compound 130 is prepared from compound 122 as follows:

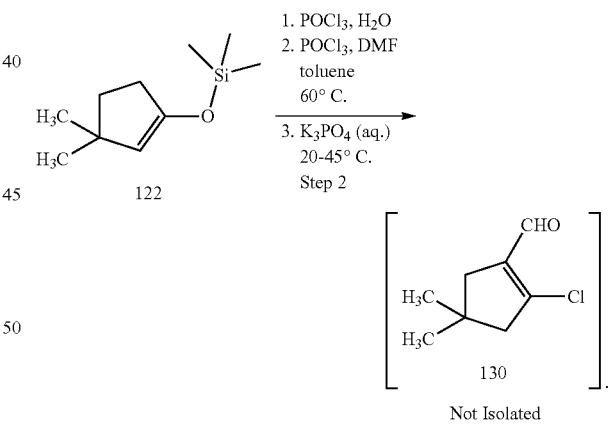

The solution of compound 122 (115.4 g, 136 mL, 2.7 rel. vol., 1 eq.) was charged to a reactor under an inert gas atmosphere and was diluted with toluene (27.5 g, 0.6 rel. vol.) to an adjusted compound 122 assay of 35 w/w %. Water (1.95 g, 0.4 eq.) was added to the reactor followed by phosphorous oxychloride (13.7 g, 0.33 eq.) at a temperature of 10 to 30° C. An emulsion formed that was stirred at temperature for at least 30 minutes upon which water droplets were not detectable. DMF (39.7 g, 2.0 eq.) was added at 10 to 30° C. followed by addition of phosphorous oxychloride (87.3 g, 2.1 eq.) at 10 to 60° C. followed by heating to 55 to 65° C. for 6 to 8 h. An emulsion formed that was cooled to 30 to 40° C. The emulsion was transferred to a quench reactor and was quenched at 20 to 45° C. onto 20 w/w % potassium phosphate solution (375 mL, 453.8 g, 7.5 rel. vol., 1.6 eq.). The reactor was rinsed with toluene (10 mL, 0.2 rel. vol.) to the quench reactor and the emulsion was stirred for 30-60 min and adjusted to 20 to 30° C.

The phases were separated to obtain organic layer 1 (144.3 g, 162 mL) and aqueous layer 1 (575.6 g, 473 mL). Organic layer 1 was washed with a mixture of 20 w/w % potassium phosphate solution (50 mL, 60.5 g, 1.0 rel. vol., 0.2 eq.) and water (50 mL, 1.0 rel. vol.). The organic layer was filtered to obtain compound 130 in solution in toluene (155 mL, 3.1 rel. vol.), the solution having a compound 130 purity of 58 area % by HPLC.

In a third step, compound 160 is prepared from compound 130 as follows:

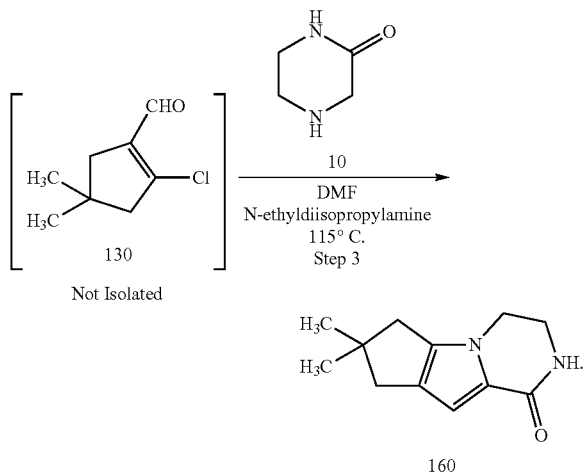

In a reactor, N-ethyldiisopropylamine (42.2 g, 1.2 eq) and piperazin-2-one (compound 10) (21.7 g, 0.8 eq.) are suspended in DMF (150 mL, 3.0 rel. vol.) under an inert gas atmosphere followed by heating to 110 to 115° C. Compound 130 in toluene from step 2 (155 mL, 3.1 rel. vol.) were added at 110 to 115° C. and stirred for 90-120 min at temperature. A reaction product mixture solution resulted that was cooled to 60 to 90° C. Unreacted compound 130 was no more than 1 area % by HPLC. Water (50 mL, 1.0 rel. vol.) was added to the reaction product mixture at 85 to 95° C. followed by cooling to 75 to 85° C. to form a suspension of compound 160. The suspension was cooled to 20 to 30° C., water (200 mL, 4.0 rel. vol.) was added, and the suspension was stirred for at least 1 h. The suspension was filtered to yield wet crude compound 160 (DMF/toluene/water). Crude compound 160 was slurried in acetone (150 mL, 3.0 rel. vol.) at 20 to 30° C. for at least 30 minutes. Wet compound 160 was collected and was washed with acetone (2×50 mL, 2×1.0 rel. vol.) to yield purified wet compound 160 (26 g) that was then dried at 70° C. and 50 mbar.

The yield of compound 160 was: 42% of theoretical based on step 1 (compound 122); 53% of theoretical based on piperazin-2-one; and 34% of theoretical based on compound 110 (3-methylcyclopent-2-en-1-one). The purity of compound 160 was 99.8 area % by HPLC and the assay of compound 160 was 98.0 area % by HPLC.

Example 4

Compound 90 was prepared according to the reaction scheme in FIGS. 3 and 4.

In a first step, compound 70 was prepared from compound 60 as follows;

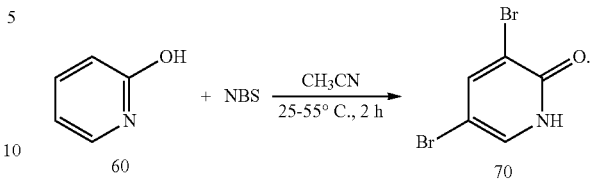

Compound 60 (425.0 kg, 1 eq.) and CH$_3$CN (4713 kg) were charged to a reactor with agitation and the temperature was adjusted to from 5 to 20° C. N-bromosuccinimide (1631.0 kg, 2.05 eq.) was charged to the reactor with agitation over a period of 30 hours while maintaining the temperature below 20° C. The temperature was adjusted to 5 to 15° C. and agitated a temperature for 4 hours. The reaction product mixture was sampled and compound 60 was not detectably by HPLC. The mixture was cooled to −5 to 5° C. over 3 hours and was agitated for 6 hours at temperature. Na$_2$S$_2$O$_3$.5H$_2$O (77 kg in solution in 425 kg water) was charged to the mixture in 90 minutes while maintaining the temperature at −5 to 5° C. The mixture was filtered and compound 70 was isolated as a wet cake by filtration. The wet cake was rinsed with CH$_3$CN (850 kg). The solid compound 70 and water (6800 kg) was charged to a reactor and the mixture was agitated at 45 to 55° C. for 2 hours. The mixture was filtered to isolate compound 70. The solid compound 70 and water (6800 kg) was charged to a reactor and the mixture was agitated at 45 to 55° C. for 2 hours. The mixture was filtered and 912 kg compound 70 (3,5-dibromopyridin-2(1H)-one) was obtained at a yield of 81%. The purity was 99.2 area % by HPLC and 99.9% weight assay by HPLC.

In a second step, compound 90 was prepared from compound 70 as follows:

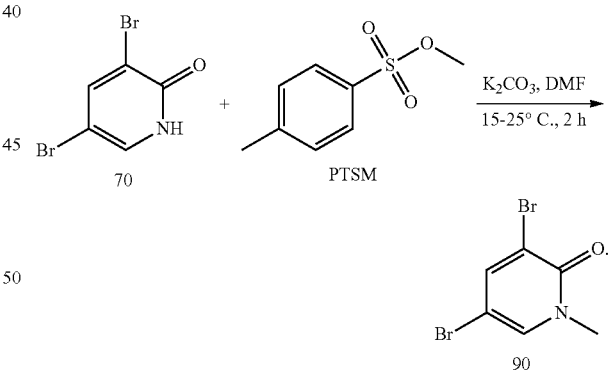

Compound 70 (752 kg, 99.9% assay by HPLC, 1 eq.) and dimethylformamide were charged to a reactor. K$_2$CO$_3$ (728 kg, 1.77 eq.) and water (5654 kg) were charged to the reactor with agitation at 20 to 30° C., and the mixture was cooled to 5 to 10° C. PTSM (843 kg, 1.52 eq.) was added dropwise while maintaining the temperature at 10 to 15° C. The mixture was agitated for 20 hours at 15 to 25° C. The reaction product mixture was sampled and 1% of compound 70 was detectably by HPLC. The reaction mixture was cooled to 0 to 5° C. and agitated at temperature for 3 hours. The mixture was filtered and compound 90 (3,5-dibromo-1-methylpyridin-2(1H)-one) was isolated as a wet cake that was then washed with water (2923 L). Anhydrous ethanol (4496 L) was charged to a reactor and combined with compound 90 wet cake with agitation. The mixture was agitated at 20 to 25° C. for 3 hours, followed by cooling to 0 to 5° C. and agitation for 3 hours. The mixture was filtered to isolate compound 90 that was dried under reduced pressure at a temperature of less than 40° C. for 20 hours to yield 679.3 kg compound 90. The conversion of compound 70 to compound 90 was 99% with a purity of 93 area % including 2.8% byproduct.

Example 5

Compound 154 was prepared according to the reaction scheme in FIGS. 3 and 4.

In a first step, compound 40 was prepared from compound 30 as follows:

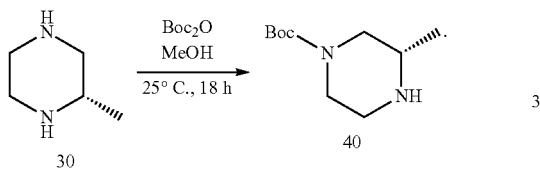

Water (500 g, 5 w/w %) was charged to a reaction flask. Compound 30 (2-methylpiperazine) (100 g, 998.4 mmol, 1 eq.) was charged to the reaction flask with agitation. HCl (36% aqueous, 102.1 g, 1008 mmol, 1.01 eq.) and methanol (200 g) were charged to the reaction flask with agitation. A solution of $Boc_2O$ (222 g, 1008 mmol, 1.01 eq.) in methanol (200 g) was added dropwise to the reaction flask at 15 to 25° C. followed by stirring for 18 hours at 20 to 30° C. The flask contents were evaporated to dryness in vacuo at 40 to 50° C. to form a residue. Water (500 g) was added to the residue and the mixture was stirred for 1 hours. The mixture was filtered and the collected solids were washed with water (50 g). The aqueous filtrate was extracted with ethylacetate (500 mL). The extracted aqueous phase was adjusted to a pH in excess of 12 with 30% NaOH and was then extracted with ethylacetate (500 mL) three times. The organic phase was washed with brine (500 g) twice and was then dried with anhydrous $Na_2SO_4$. The dried mixture was filtered and the collected solids were rinsed with ethylacetate (100 mL). The filtrate was concentrated to dryness in vacuo at 50 to 60° C. and further concentrated under high vacuum (5 mm Hg) at 65 to 75° C. for 3 hours to yield compound 40 (tert-butyl 3-methylpiperazine-1-carboxylate). The purity of compound 40 was 97.7 area %, the assay was 95.9% and the yield was 76.4%.

Compound 40 was prepared under various conditions of temperature, catalyst loading, strict air-free conditions and exposure to a trace amount of air according to the above method. The results are reported in Example 5 Table 1 below where "Exp." refers to experiment and "Cmpd." refers to compound.

TABLE 1

| | | | | Example 5 | | | | |
|---|---|---|---|---|---|---|---|---|
| | | | | Conditions | | | Purity | |
| Exp | Air | Cmpd. 50 | Cmpd. 40 | $Pd(OAc)_2$ | BINAP | T (° C.) | Cmpd. 50 | Cmpd. 154 |
| 1 | trace | 5 mmol | 5 mmol | 0.02 eq. | 0.02 eq. | 70-75 | 65.8 A % | 25.1 A % |
| 2 | trace | 20 mmol | 20 mmol | 0.01 eq. | 0.01 eq. | 90-95 | 31.3 A % | 63.2 A % |
| 3 | trace | 10 mmol | 10 mmol | 0.02 eq. | 0.02 eq. | 90-95 | 0.48 A % | 93.1 A % |
| 4 | none | 6.3 mmol | 6.3 mmol | 0.01 eq. | 0.01 eq. | 90-95 | 1.3 A % | 94 A % |

In a second step, compound 154 was prepared from compounds 40 and 50 as follows:

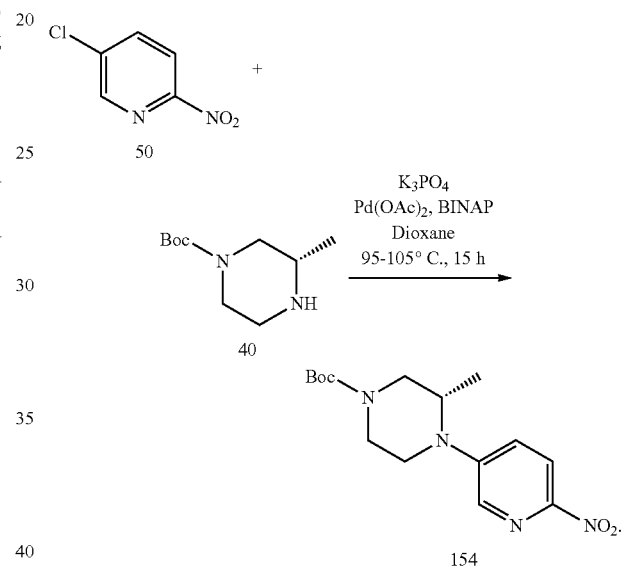

Dioxane (1.5 L, 10 v/w %) was charged to a reaction flask and agitation was started. The reaction flask was evacuated and refilled with $N_2$ three times. Compound 50 (118.7 g, 733.7 mmol, 1.02 eq.), compound 40 (150 g, 718 mmol, 1.0 eq.), and $K_3PO_4$ (318 g, 1468 mmol, 2.09 eq.) were charged to the reaction flask with constant flow of $N_2$. The reaction flask was evacuated and refilled with $N_2$ three times. $Pd(OAc)_2$ (3.4 g, 15.1 mmol, 0.021 eq.) catalyst and BINAP ligand (9.3 g, 14.9 mmol, 0.021 eq) were added to the reaction flask with constant flow of $N_2$. The reaction flask was evacuated and refilled with $N_2$ three times and $N_2$ flow was continued for 1 h. The mixture was heated to 95 to 105° C. and stirred at temperature for 15 h under $N_2$ flow. The reacted mixture was cooled to 50 to 60° C. and filtered at that temperature. The collected solids were washed with hot dioxane. The liquid filtrate was concentrated to dryness in vacuo at 50 to 60° C. to form a residue. i-propanol (300 g) was combined with the residue and the mixture was slurried at −5 to 5° C. for 1 hour and then filtered. The collected solids were washed with cold i-propanol. The wet solids were dried in vacuo at 60 to 70° C. to yield compound 154 (t-butyl (S)-3-methyl-4-(6-nitropyridin-3-yl)piperazine-1-carboxylate). The purity of compound 154 was 99.5 area % by HPLC, the assay was 94.4% and the yield was 80.5%.

Compound 153 was produced in a second method wherein the halogen of compound 50 was bromine according to the following reaction scheme:

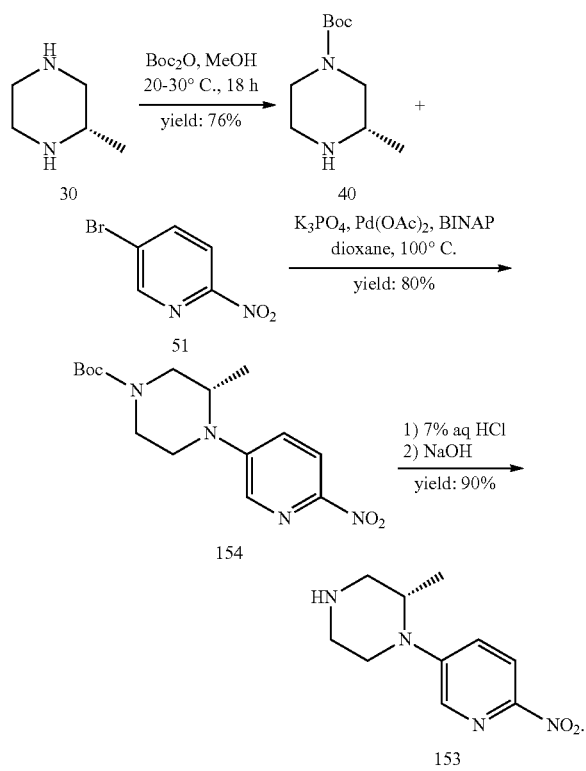

Compound 30 (299.98 g) was charged to a reactor followed by water (1.5 L) under a N₂ blanket. The mixture was stirred at 20 to 30° C. until clear. 37% HCl (299.41 g) was charged to the reactor over a period of about 1 hour under a N₂ blanket to a final pH of about 7.1. The mixture was stirred at 20 to 30° C. for 30 minutes. (Boc)₂O (654.05 g in 1.5 L methanol) was added to the reactor under a N₂ blanket over a period of about 2.5 hours. The mixture was stirred at 20 to 30° C. for 18 hours. The mixture was sampled and tested by HPLC indicating 6.2 area % compound 30 and 90.4% compound 40. (Boc)₂O (26.2 g) was added to the reactor and the mixture was stirred at 20 to 30° C. for 2.5 hours. The mixture was sampled and tested by HPLC indicating 3.2 area % compound 30 and 92.8% compound 40. The reactor jacket temperature was adjusted to 40 to 45° C. and the mixture was concentrated to remove methanol to a final methanol concentration of 0.06%.

Water (1200 mL) was charged to the mixture in the reactor followed by ethyl acetate (600 mL), and the resulting mixture was stirred at 20 to 25° C. for 1 hour. Agitation was stopped and the mixture was allowed to settle and separate to an ethyl acetate layer and an aqueous layer. Ethyl acetate (600 mL) was added to the aqueous layer, and the resulting mixture was stirred at 20 to 25° C. for 30 minutes. Agitation was stopped and the mixture was allowed to settle and separate to an ethyl acetate layer and an aqueous layer. 30% NaOH solution (900 g) was added to the aqueous layer to adjust the pH to about 11. The pH 11 aqueous layer was extracted with ethyl acetate (600 mL) three times. Residual compound 40 in the aqueous layer was 0.02% and compound 40 loss was 0.12%. The ethyl acetate layers were combined and the combined layers were washed with 5% aqueous Na₂SO₄ (900 mL) two times. Compound 40 residual in the Na₂SO₄ layer was 0.83% and compound 40 loss was 2.9%. The ethyl acetate phase was concentrated to 900 mL under reduced pressure at 40 to 50° C. 1,4-dioxane (900 mL) was added and to the concentrate mixture, and the volume reduced to 900 mL under reduced pressure at 40 to 50° C. A solution of compound 40 in dioxane (923.63 g) was obtained having a residual ethyl acetate content of 0.31% and a water content by KF of 2.31%. A portion of the compound A/dioxane solution (30.8 g) was concentrated to dryness under high vacuum at 40 to 50° C. Compound A (16.44 g) was obtained and the compound 40 purity was 93.1% by qNMR and the compound 40 yield was 76.6%.

Compound 40 (200 g, 998 mmol) and compound 51 (206.76 g, 1019 mmol) were charged to a reactor followed by dioxane (1000 mL, 5 vol.). K₃PO₄ (436.7 g) was charged in portions to the reactor at 20 to 30° C. The reactor contents were stirred at 20 to 30° C. for 1 hour while sparging with N₂. Pd(OAc)₂ catalyst (4.65 g) and BINAP ligand (12.84 g) were added to the reactor under a N₂ blanket, the temperature was adjusted to 20 to 30° C. and the mixture in the reactor was stirred at that temperature of 16 hours under a N₂ blanket to form compound 154. The temperature was adjusted to 55 to 65° C. and water (600 mL) was added to the reactor over 15 minutes and the mixture was stirred for 20 minutes at 55 to 65° C. The phases were separated and collected and the aqueous phase was extracted with dioxane (400 mL) at 55 to 65° C. The organic layers were combined and the temperature was adjusted to 20 to 30° C. Compound 154 seed crystals (0.894 g) added to the combined organic layers and the mixture was stirred at 20 to 30° C. for 30 minutes. Water (1200 mL) was slowly added to the mixture followed by stirring at 20 to 30° C. for 10 hours to produce compound 154 crystals. Thereafter, the temperature was reduced to 0 to 10° C. and the mixture was stirred at that temperature for 1.5 hours. The mixture was filtered to collect compound 154 crystals that were then washed with 0 to 10° C. water (400 mL) to produce 741.8 g wet solid compound 154. The solid compound 154 was dried under vacuum at 40 to 50° C. for 24 hours to yield 287.4 g dry compound 154.

2M HCl (278 g) was charged to a reactor and heated to 50 to 60° C. Compound 154 (46 g) was charged to the HCl in portions over 1 hour at 50 to 60° C. followed by stirring at that temperature for 4 hours to produce compound 153. The contents of the reactor were filtered and the collected solids were washed with water (96 g) twice. The aqueous filtrate (mother liquor) was extracted with dichloromethane (122 g). The pH of the extracted filtrate was adjusted to 11 with 30% NaOH (110 g) followed by extraction twice with dichloromethane (304 g per extraction). The organic phases were combined and washed with 5% Na₂SO₄ (230 g). The organic phases were decolorized by filtration through diatomaceous earth and were then concentrated by 3×. The concentrated organic phase was swapped with four times with isopropyl acetate (46 g IPAC per swap). The mixture comprising compound 153 in solution in IPAC was cooled to 0 to 5° C. over 1 hour and stirred at that temperature for 2 hours. n-heptane (230 g) was added over 1 hour at 0 to 5° C. and the mixture was stirred at that temperature for 1 hour. The mixture was concentrated by 7× and was then swapped four times with n-heptane (46 g n-heptane per swap). The mixture comprising solid compound 153 in heptane with trace amounts of IPCA was cooled to 0 to 5° C. over 1 hour and stirred at that temperature for 2 hours. The mixture was filtered to collect compound 153 as a wet cake that was then dried under reduced pressure at 45 to 55° C. to yield compound 153 as a yellow solid (28.5 g, 99.9 area % by HPLC, 88% isolated yield).

Example 5A

In an alternative method to Example 5 above, Compound 154 is prepared as follows:

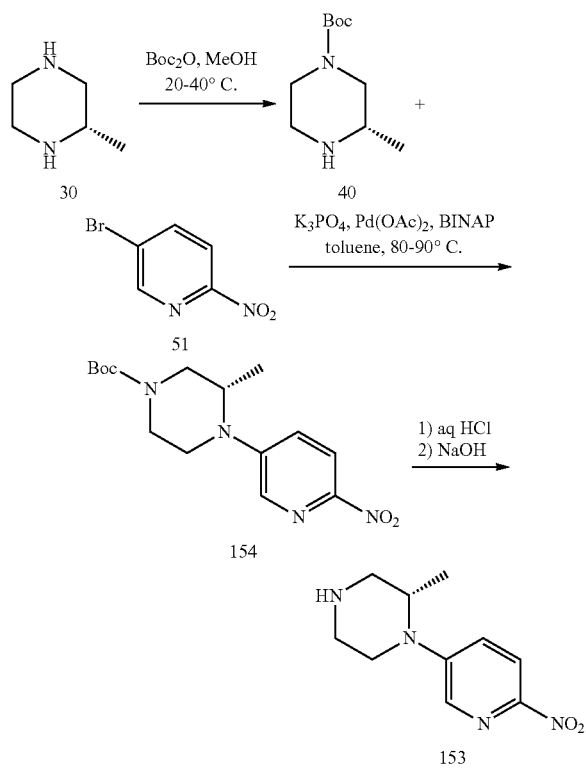

Compound 30 (9.6 kg, 1.0 eq) is dissolved in process water (50 kg, 5.0×). The reaction mixture is stirred for 1.5 h at IT=20~40° C. The reaction mixture is adjusted to IT=10~20° C. 35% HCl (10.0 kg, 1.0×) is added at IT<30° C. to pH=7.0~7.2. Process water (5 kg, 0.5×) is added. The reaction mixture is stirred for 0.5 h at IT=10~20° C. (Boc)₂O/MeOH solution (58.4 kg, 5.84×) and MeOH (5.0 kg, 0.5×) are added at IT<20° C. The reaction mixture is stirred for 16 h at IT=1520° C. Conversion is checked by HPLC (SM1/A %≤3%; SM1/A %=4%). (Boc)₂O/MeOH solution (2.2 kg, 0.22×) and MeOH (5.0 kg, 0.5×) are added at IT<20° C. The reaction mixture is stirred for 3 h at IT=15~20° C. Conversion is checked by HPLC (SM1/A %≤3%; SM1/A %=3%). The mixture is concentrated to 5-7× at IT≤40° C. under reduced pressure. Conversion is checked by HPLC (MeOH %-w/w %≤10%; MeOH %-w/w %=2%). Process water (52 kg, 5.2×) and toluene (18.0 kg, 1.8×) are added. The mixture is stirred for 1 h at IT=20~30° C. and settled down 1.5 h. Two layers are separated. The aqueous layer is extracted by toluene (20.0 kg, 2.0×) at IT=20~30° C. Combined organic layer is checked by HPLC (Residual A: FIO). The aqueous layer is basified with liquid sodium (19.6 kg, 1.96×) at IT<30° C. to pH=10.5~11.5. The basified aqueous solution is extracted by toluene (19.8+20+19.6 kg, 5.94×) three times at IT=20~30° C. Combined aqueous layer is checked by HPLC (Residual A: FIO). The combined organic layer is washed with 10% Na₂SO₄ solution (30*2 kg, 6.0×) two times at IT=20~30° C. Combined aqueous layer is checked by HPLC (Residual A: FIO). The mixture is concentrated to 3-5× below 70° C. under reduced pressure. KF is checked (KF≤3.0%; KF=0.01%). Toluene solution is checked by HPLC.

The toluene solution of Compound 40 (24.0 kg, active A: 11.0 kg, 1.0×) is dissolved in toluene (45 kg, 4.1×). Compound 51 (8.85 kg, 0.80×) and anhydrous potassium phosphate (24.0 kg, 2.2×) are added. The reaction mixture is bubbled with N₂ for 4.5 h at IT=20~30° C. Palladium acetate (0.21 kg, 0.019×) and BINAP (0.55 kg, 0.05×) are added. The reaction mixture is bubbled with N₂ for 1.5 h at IT=20~30° C. Then the reaction mixture is stirred for 20.5 h at IT=80~90° C., then adjusted to IT=40~50° C. Conversion is checked by HPLC (SM2/B %≤1.0%; SM2/B %: N.D.). Then adjusted to IT=35~45° C. 13.5% HCl solution (110.55 kg, 10.05×) and process water (3 kg, 0.27×) are added at IT<55° C. The reaction mixture is stirred for 15 h at IT=50~55° C. and settled down 40 min. The organic phase is checked by HPLC (B %-w/w≤0.3%; B %-w/w=0.02%). The reaction mixture is settled down 1 h at IT=35~45° C. Two layers are separated. The aqueous layer is extracted by triphenylphosphine (0.27 kg, 0.025×) and 2-MeTHF (60 kg, 5.45×) at IT=35~45° C. The aqueous layer is extracted by 2-MeTHF (30 kg, 2.73×) at IT=35~45° C. The organic layer is checked by HPLC (C %-w/w: report; C %-w/w=0.008%). The aqueous layer is extracted by 2-MeTHF (61 kg, 5.55×) and basified with liquid sodium (66 kg, 6.0×) at IT=25-35° C. to pH=11~12. The basified aqueous solution is extracted by 2-MeTHF (33+33 kg, 6.0×) twice at IT=35~45° C. The aqueous layer is checked by HPLC. The combined organic layer is washed with 25% NaCl solution (30 kg, 2.73×) at IT=20~30° C. The aqueous layer is checked by HPLC. The obtained organic solution is discolored by circulating through CUNO for 16 h at IT=20~30° C. 2-MeTHF (16 kg, 1.45×) is added by CUNO. The solution is concentrated to 3.0-4.5× at IT≤45° C. under reduced pressure and switched into IPAc solution (17+17+17+17 kg, 6.18×) four times. Residual 2-MeTHF is checked by HPLC (residual 2-MeTHF: report; residual 2-MeTHF=0.6%). The mixture is stirred for 3 h at IT=0~10° C. n-heptane (80 kg, 7.3×) is added at IT=0~10° C. The mixture is stirred for 1 h at IT=0~10° C. The solution is concentrated to 6-7× at IT≤45° C. under reduced pressure and switched into n-heptane solution (17+17+17 kg, 4.64×) three times. The supernatant is checked by HPLC (residual IPAc≤10.0%, residual 2-MeTHF≤1.0%; residual IPAc=3.6%, residual 2-MeTHF=0.3%). The mixture is stirred for 2.5 h at IT=0~10° C. The wet cake is checked by HPLC. Solid is collected by filter and washed with 2-MeTHF (10 kg, 0.91×). The last solid is collected by centrifuging and washed with n-heptane (7 kg, 0.64×). The pure wet product is dried for 13.5 h at IT=40~50° C. under reduced pressure till IPC is fulfilled. The product was discharged to give 9.08 kg of Compound 153.

Example 6

Compound 153 was prepared according to the reaction scheme in FIGS. 3 and 4.

Compound 153 was prepared from compound 154 as follows:

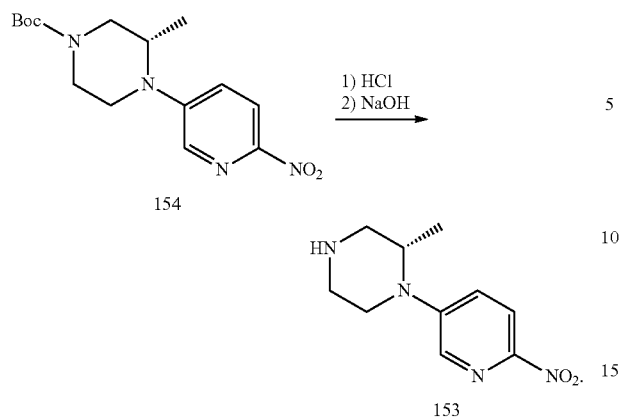

154

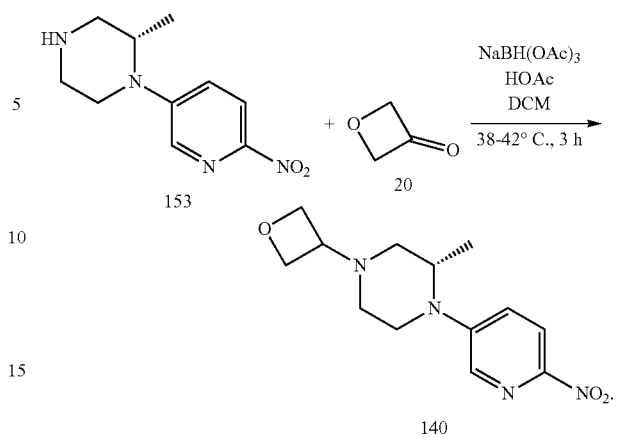

153

153

140

Water (800 g) was charged to a 2000 mL reaction flask. 36% HCl (236 g, 2.33 mmol, 4.08 eq.) was charged to the reaction flask with agitation and the mixture was heated to 50 to 60° C. Compound 154 (195 g, 94.4% assay, 571 mmol, 1 eq.) was added in portions at 50 to 60° C. and the mixture was stirred at 50 to 60° C. for 3 hours. The mixture was cooled to 15 to 25° C. and was extracted with dichloromethane (1 L). The aqueous phase pH was adjusted to greater than 11 with aqueous 30% NaOH and was then extracted with dichloromethane (1.5 L) twice. The dichloromethane phases were combined and washed with water (1 L) twice. The dichloromethane phase was dried with anhydrous MgSO$_4$. The mixture was filtered and the collected solid was washed with dichloromethane. The filtrate and wash were combined and yielded 2814.2 grams of compound 153 in solution in dichloromethane (4.18% compound 153 assay; 92.7% yield; 0.13% water by KF).

Compound 153 was prepared using various solvent systems according to the above method. The results are reported in Example 6 Table 1 below where: "Exp." refers to experiment; "C 153" refers to compound 153; "C 154" refers to compound 154; "A %" refers to area % by HPLC; "Crude" refers to the assay in area % of the referenced compounds in the reaction product mixture and prior to work-up; and the purity and yield of compound 153 is after work-up. Experiment 1 resulted in about 6 A % of an impurity and reactions 2 to 5 gave clean reactions.

The dichloromethane solution from Example 6 (2814.2 g, 4.18 A % compound 153, 529.3 mmol compound 153, 1 eq. compound 153) was charged to a reactor and agitation was started. Acetic acid (47.7 g, 99%, 787 mmol, 1.5 eq.) and anhydrous MgSO$_4$ (28 g, 1.0 w/w %) were added to the reactor followed by oxetan-3-one (compound 20) (61.1 g, 848 mmol, 1.6 eq.). The mixture was heated to 30 to 40° C. and NaBH(OAc)$_3$ (338 g, 97%, 1547 mmol, 2.9 eq.) was added in portions at 30 to 40° C. The mixture was stirred for 2 h at 38 to 45° C. The mixture was cooled to less than 20° C. and water (1070 g) was charged to the reactor. The mixture formed layers that were separated into an organic layer and an aqueous layer. The aqueous layer was extracted with dichloromethane (1000 g). The organic layers were combined and were washed with water (800 g) twice. The organic layer was dried with anhydrous MgSO$_4$ and the resulting mixture was filtered. The collected solids were washed with dichloromethane. The dried organic layer and dichloromethane wash were combined and then concentrated in vacuo to below 50° C. to almost dryness to form a residue of compound 140 ((S)-2-methyl-1-(6-nitropyridin-3-yl)-4-(oxetan-3-yl)piperazine). Petroleum ether (350 mL) was added to the residue and the mixture was stirred at 15 to 25° C. for 1 hour. The mixture was filtered and the collected compound 140 solids were dried in vacuo at 50 to 60° C. for 5 hours. The compound 140 purity was 98.7 area %, the assay was 98.9%, and the yield was 91.3%.

Compound 140 was prepared from various equivalent ratios of compound 20 to compound 153 according to the above method. The results are reported in Example 7 Table 1 below where "Exp." Refers to experiment number; "C 153" refers to compound 153 HCl salt or free base, and

|  | C 154 |  | Conditions |  | Crude |  | C 153 |  |  |
|---|---|---|---|---|---|---|---|---|---|
| Exp. | mmol | Solvent | T (° C.) | Time | C 154 | C 153 | Amount | Purity | Yield |
| 1 | 100 | Dioxane/DCM | 15-25 | 10 h | 0.92 A % | 87.3 A % | 26 g | 90.4 A % | 88% |
| 2 | 100 | IPA/MeOH | 15-25 | 10 h | 0.03 A % | 99.4 A % | 25.6 g | 99.8 A % | 86.8% |
| 3 | 10 | MeOH | 15-25 | 20 h | NA | 94.8 A % | — | — | — |
| 4 | 20 | EtOH | 15-25 | 40 h | 0.76 A % | 98.9 A % | — | — | — |
| 5 | 50 | H$_2$O | 50-60 | 4 h | NA | 97.6 A % | 10 g | 99.8 A % | 90% |

Example 7

Compound 140 was prepared according to the reaction scheme in FIGS. 3 and 4.

Compound 140 was prepared from compounds 153 and 20 as follows:

wherein the amount of compound 153 in each example reaction was 1 equivalent; "C 140" refers to compound 140; "eq." refers to equivalents; "C 20" refers to compound 20; "A %" refers to area percent by HPLC; "Crude" refers to the assay in area % by HPLC of the referenced compounds in the reaction product mixture and prior to work-up; and the purity and yield of compound 140 is after work-up.

TABLE 1

Example 7

| | | | Crude | | C 140 | | |
|---|---|---|---|---|---|---|---|
| Exp. | C 153 | C 20 | C 140 | C153 | Amount | Purity | Yield |
| 1 | 76 mmol (HCl salt) | 1.8 eq. | 98.1 A % | NA | 12 g | 99.4 A % | 84.0% |
| 2 | 7 mmol (HCl salt) | 1.5 eq. | 94.9 A % | 0.51 A % | NA | NA | NA |
| 3 | 7 mmol (HCl salt) | 1.2 eq. | 80.1 A % | 7.8 A % | NA | NA | NA |
| 4 | 8.6 mmol (free base) | 1.5 eq. | 97.2 A % | 1.2 A % | 2.03 g | 99.7 A % | 86.0% |
| 5 | 43 mmol (free base) | 1.6 eq. | 95.9 A % | 0.82 A % | 10.2 g | 98.2 A % | 85.7% |

Compound 140 was prepared compound 153 in solution in dichloromethane at a concentration of about 4 w/w % to about 5 w/w % according to the above method. The results are reported in Example 7 Table 2 where "Exp." Refers to experiment number; "C 153" refers to compound 153; "C 140" refers to compound 140; "eq." refers to equivalents; "C 20" refers to compound 20; "A %" refers to area percent by HPLC; "Crude" refers to the assay in area % HPLC of the referenced compound in the reaction product mixture and prior to work-up; and the purity and yield of compound 140 is after work-up.

TABLE 2

Example 7

| | | | Crude | | C 140 | | |
|---|---|---|---|---|---|---|---|
| Exp. | C 153 | C 20 | C 140 | C153 | Amount | Purity | Yield |
| 1 | 15.5 mmol | 1.5 eq. | 97.7 A % | 0.49 A % | 3.55 g | NA | 82.3% |
| 2 | 125 mmol | 1.6 eq. | 96.2 A % | 0.44 A % | 28.8 g | 98.6 A % | 82.8% |

The results indicate that compound 140 can be prepared from compound 153 in solution in dichloromethane at high yield and purity.

Example 8

Compound 141 was prepared according to the reaction scheme in FIGS. 3 and 4.

Compound 141 was prepared from compound 140 as follows:

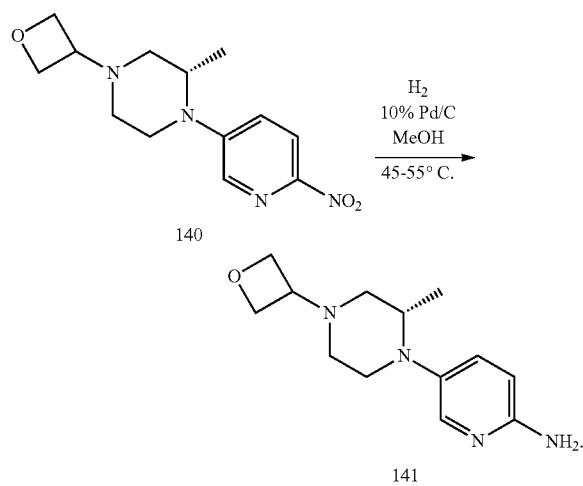

Methanol (675 mL) was charged to a reaction flask. Compound 140 (135 g, 98.9 A %, 537.7 mmol, 1 eq.) was charged to the reaction flask with agitation followed by 10% palladium on carbon catalyst (27 g, 20 w/w %, 59% wet). The reaction flask was evacuated and filled with $N_2$ three times and was then evacuated and filled with $H_2$ three times. The mixture was heated to 45 to 55° C. for 15 hours. The mixture was cooled to 20 to 25° C. and was then filtered. The filtrate was concentrated in vacuo at a temperature of less than 60° C. to almost dryness to form a residue. The residue was combined with dioxane (675 mL) and the resulting mixture was concentrated in vacuo at a temperature of less than 60° C. to almost dryness to form a residue. The residue was diluted with dioxane (1200 mL) to form a solution of compound 141 in dioxane (1295.5 g). The compound 140 yield was 90.3%, the assay was 8.3%, and the methanol residue was 0.13% as measured by GC.

Various solvents were evaluated for the preparation of compound 141 from compound 140 according to the above method. The results are summarized in Example 8 Table 1 below where "Exp." refers to experiment; "C 140" refers to compound 140; "C 141" refers to compound 141; "Pd/C" refers to palladium on carbon catalyst and the 10% Pd/C catalyst was 59% wet; and "Crude" refers to the assay in area % HPLC purity of the referenced compound in the reaction product mixture and prior to work-up (filtration).

TABLE 1

Example 8

| | | Conditions | | | | |
|---|---|---|---|---|---|---|
| | | | | Rx | Crude | |
| Exp. | C 140 | 10% Pd/C | Solvent | Time | C 140 | C 141 |
| 1 | 3.6 mmol | 2 w/w % | Ethanol | 16 h | 56.8 A % | 31.9 A % |
| 2 | 3.6 mmol | 2 w/w % | Dioxane | 16 h | 73.2 A % | 21.1 A % |
| 3 | 3.6 mmol | 5 w/w % | Dioxane | 16 h | 25.5 A % | 72 A % |
| 4 | 54 mmol | 2 w/w % | Methanol | 10 h | 0.13 A % | 90.1 A % |

Palladium on carbon catalyst loading was evaluated for the preparation of compound 141 from compound 140 according to the above method. The results are summarized in Example 8 Table 2 below where "Exp." refers to experiment; "C 140" refers to compound 140 where the compound 140 purity was 98.4 A %; "C 141" refers to compound 141; "Crude" refers to the assay in area % by HPLC of the referenced compound in the reaction product mixture and prior to work-up (filtration).

TABLE 2

Example 8

| Exp. | C 140 | Pc/C loading | Crude C 141 | Impurity 1 | Impurity 2 |
|---|---|---|---|---|---|
| 1 | 15 g | 2 w/w % | 90.1 A % | 2 A % | 4.1 A % |
| 2 | 5 g | 5 w/w % | 95.8 A % | 0.6 A % | 2 A % |
| 3 | 166 g | 10 w/w % | 97.5 A % | 0.43 A % | 0.77 A % |
| 4 | 5 g | 20 w/w % | 98.2 A % | 0.18 A % | 0.27 A % |

Recovery and reuse of palladium on carbon catalyst was evaluated for the preparation of compound 141 from compound 140 according to the above method where the starting amount of compound 140 in each of experiments 1 to 4 below was 35.9 mmol. The results are summarized in Example 8 Table 3 below where "Exp." refers to experiment; "C 140" refers to compound 140 where the compound 140 purity was 98.4 A %; "Pd/C" refers to palladium on carbon catalyst; "Crude" refers to the compound 140 assay in area % by HPLC of the referenced compound in the reaction product mixture and prior to work-up (filtration); and "RT" refers to reaction time in minutes.

TABLE 3

Example 8

| | | IPC | | | |
|---|---|---|---|---|---|
| Exp. | 10% Pd/C | RT: 4.93 | RT: 5.21 | RT: 5.32 | RT: 6.89 | RT: 7.39 |
| 1 | 2.0 g, 20 w/w % | 98.3 A % | 0.69 A % | 0.13 A % | 0.48 A % | 0.1 A % |
| 2 | Recycle from Exp. 1 + 0.2 g fresh catalyst | 98.2 A % | 0.35 A % | 0.12 A % | 0.71 A % | 0.03 A % |
| 3 | Recycle from Exp. 2 + 0.2 g fresh catalyst | 98 A % | 0.47 A % | 0.14 A % | 0.78 A % | 0.08 A % |
| 4 | Recycle from Exp. 2 + 0.2 g fresh catalyst | 97.9 A % | 0.52 A % | 0.14 A % | 0.91 A % | 0.06 A % |

The solubility of compound 141 was evaluated in various solvents. In the evaluation, a compound 141 sample was place into a 1.5 mL vial, 1 mL of the solvent was added, and the mixture was sonicated at 25° C. for 5 minutes. The mixture was then centrifuged, the upper supernatant was filtered through a microfilter, a filtrate aliquot was taken, diluted with acetonitrile, filtered, and injected into an HPLC column. The results are summarized in Example 8 Table 4 below where the purity of compound 141 was greater than 98 area % by HPLC.

TABLE 4

Example 8

| Experiment | Solvent | Solubility (mg/mL at 25° C.) |
|---|---|---|
| 1 | Methanol | 221.4 |
| 2 | Ethanol | 153.5 |
| 3 | Water | 30.7 |
| 4 | Isopropanol | 222.2 |
| 5 | Ethyl acetate | 82.3 |
| 6 | Dichloromethane | 268.7 |
| 7 | Toluene | 20.6 |

TABLE 4-continued

Example 8

| Experiment | Solvent | Solubility (mg/mL at 25° C.) |
|---|---|---|
| 8 | tert-Butyl methyl ether | 7.39 |
| 9 | Acetonitrile | 97.7 |
| 10 | Tetrahydrofuran | 175.1 |
| 11 | Methyl tetrahydrofuran | 83 |
| 12 | Petroleum ether | 0.26 |
| 13 | Heptane | 0.32 |
| 14 | Acetone | 153.8 |
| 15 | Dimethylformamide | 199.5 |

Example 9

Compound 180 was prepared according to the reaction scheme in FIGS. 3 and 4.

Compound 180 was prepared from compound 140 and compound 90 as follows:

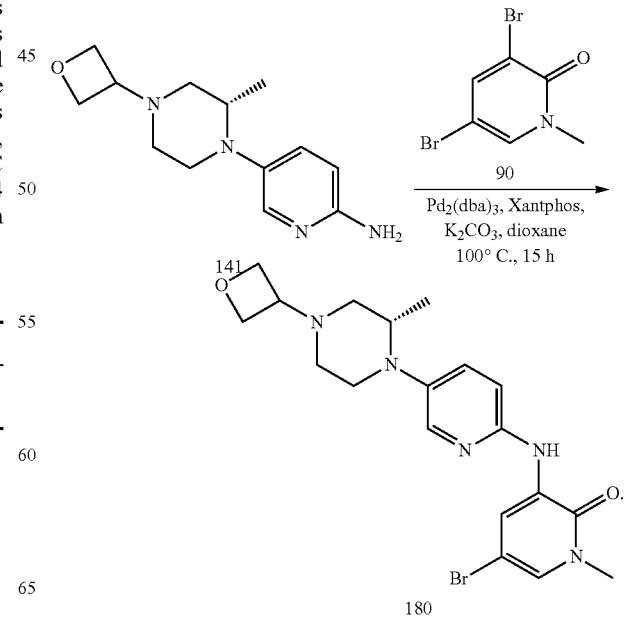

The solution of compound 141 in dioxane from Example 8 (1295.5 g, 8.3% assay, 433 mmol, 1 eq.) was charged to a reaction flask. Compound 90 (119.5 g, 96.7% assay, 433 mmol, 1 eq.) and $K_2CO_3$ (121 g, 99% assay, 17.3 mmol, 2 eq.) were charged to the reaction flask with agitation. The reaction flask was evacuated and refilled with $N_2$ three times. $Pd_2(dba)_3$ catalyst (9.05 g, 99% assay, 8.66 mmol, 0.02 eq.) and Xantphos ligand (10.2 g, 98% assay, 17.3 mmol, 0.04 eq.) were charged to the reaction flask with agitation. The reaction flask was evacuated and refilled with $N_2$ three times and the mixture was heated to 105 to 115° C., and the mixture was stirred under $N_2$ for 24 hours. The mixture was cooled to 65 to 75° C. and filtered. The collected solids were rinsed with hot dioxane. The filtrate and dioxane wash were combined and concentrated to almost dryness in vacuo at 55 to 65° C. to form a residue.

Methanol (550 mL) was combined with the residue, the mixture was stirred at 0° C. for 2 hours, the mixture was filtered to collect crude compound 180 as a solid, and the collected crude compound 180 was washed with cold methanol. The crude compound 180 was dried in vacuo at 55 to 65° C. for 1 hour. The crude product was weighed and assayed by HPLC to yield 151 g compound 180 having a purity of 97.6 area %. The crude was combined with dioxane (211 g) and the mixture was heated to reflux and stirred at reflux for 15 minutes. i-propanol (500 mL) was added dropwise to the mixture while maintaining reflux. The mixture was cooled to 15 to 25° C. and stirred for 1 hour at that temperature. The mixture was filtered and the collected compound 180 solids were rinsed with i-propanol and were dried in vacuo at 60 to 70° C. for 5 hours. Compound 180 (188 g) was collected having a purity of 99.1 area % by HPLC, an assay of 97.6%, and an assay yield of 74.1%.

$K_3PO_4$ was evaluated for the preparation of compound 180 from compounds 141 and 90 according to the above method. The results are presented in Example 9 Table 1 below where "Exp." refers to experiment; "C 141" refers to compound 141; "C 180" refers to compound 180; "C 90" refers to compound 90; "catalyst" refers to $Pd_2(dba)_3$ catalyst; and "Crude" refers to the assay in area % of the referenced compound in the reaction product mixture after a reaction time of 14.3 minutes and prior to work-up.

TABLE 1

Example 9

| | | | | IPC | | |
|---|---|---|---|---|---|---|
| Exp. | C 141 | C 90 | Base | C 141 | C 90 | C 180 |
| 1 | 8 mmol | 8 mmol | $K_2CO_3$, 2 eq. | 0.78 A % | 3.3 A % | 74.9 A % |
| 2 | 8 mmol | 8 mmol | $K_3PO_4$, 2 eq. | 0.74 A % | 3 A % | 74.6 A % |

The solvents dioxane and toluene were evaluated as solvents for palladium-catalyzed coupling reactions for the preparation of compound 180 from compounds 141 and 90 according to the above method where the reaction time was 15 hours. The results are presented in Example 9 Table 2 below where the amount of compounds 90 and 141 was 24.2 mmol for each experiment and where the equivalents of catalyst and ligand are based on equivalents of compounds 141 and 90. In the table, "Exp" refers to experiment number.

TABLE 2

Example 9

| | | | | Compound 180 | | |
|---|---|---|---|---|---|---|
| Exp. | Solvent | $Pd_2(dba)_3$ | Xantphos | Amount | Purity | Yield |
| 1 | Dioxane | 0.02 eq. | 0.04 eq. | 7.4 g | 98.9 A % | 70.5% |
| 2 | Toluene | 0.02 eq. | 0.04 eq. | 4.7 g | 94.8 A % | 44.8% |

The effect of methanol was evaluated on palladium-catalyzed coupling reactions for the preparation of compound 180 from compounds 141 and 90 according to the above method. The results are presented in Example 9 Table 3 below where the amount of compounds 90 and 141 was 34.6 mmol for experiments 1 to 3 and was 2 mmol for experiment 4. In the table, "Exp" refers to experiment number; and "RT" refers to reaction time.

TABLE 3

Example 9

| | | IPC | | |
|---|---|---|---|---|
| Exp. | MeOH residue | Compound 141 RT = 4.95 min | Compound 180 RT = 9.58 min | Compound 90 RT = 9.37 min |
| 1 | 0.1 w/w % | 1.13 A % | 76 A % | 4.48 A % |
| 2 | 0.5 w/w % | 2.22 A % | 72.6 A % | 10.8 A % |
| 3 | 1 w/w % | 2.38 A % | 75.7 A % | 3.22 A % |
| 4 | 5 w/w % | 10 A % | 74.2 A % | 10.2 A % |

By controlling methanol level in the reaction system, compound 180 can be prepared from a solution of compound 141, and without isolation of compound 141 as a residue.

The solubility of compound 180 was evaluated in various solvents. In the evaluation, a compound 180 sample was placed into a 1.5 mL vial, 1 mL of the solvent was added, and the mixture was sonicated at 25° C. for 5 minutes. The mixture was then centrifuged, the upper supernatant was filtered through a microfilter, a filtrate aliquot was taken, diluted with acetonitrile, filtered, and injected into an HPLC column. The results are summarized in Example 9 Table 4 below where the purity of compound 180 was greater than 98 area % by HPLC.

TABLE 4

Example 9

| Experiment | Solvent | Solubility (mg/mL at 25° C.) |
|---|---|---|
| 1 | Methanol | 1.35 |
| 2 | Ethanol | 1.52 |
| 3 | Water | 0.52 |
| 4 | Isopropanol | 2.65 |
| 5 | Ethyl acetate | 4.53 |
| 6 | Dichloromethane | 50.6 |
| 7 | Toluene | 9.81 |
| 8 | tert-Butyl methyl ether | 1.25 |
| 9 | Acetonitrile | 2.3 |
| 10 | Tetrahydrofuran | 24 |
| 11 | Methyl tetrahydrofuran | 7.19 |
| 12 | Petroleum ether | 0.03 |
| 13 | Heptane | 0.03 |
| 14 | Acetone | 3.73 |
| 15 | Dimethylformamide | 20.8 |
| 16 | Dioxane | 44.7 |

Compound 180 (5 g, 94.3 A %) was crystallized from various solvent systems in a number of experiments. The results are summarized in Example 9 Table 5 below.

TABLE 5

Example 9

| Exp. | Solvent (mL) | Solvent (mL) | Crystallized compound 180 | | |
|---|---|---|---|---|---|
| | | | Weight | Assay | Yield |
| 1 | DCM (10 mL) | MeOH (50 mL) | 4.3 g | 96.4 A % | 87.9% |
| 2 | DCM (6.25 mL) | MeOH (37.5 mL) | 4.38 g | 95.8 A % | 89% |
| 3 | Dioxane (9 mL) | EtOH (22 mL) | 4.27 g | 94.9 A % | 85.9% |
| 4 | Dioxane (7 mL) | i-PrOH (21 mL) | 4.61 g | 94.9 A % | 92.8% |

Example 10

Figure 2:
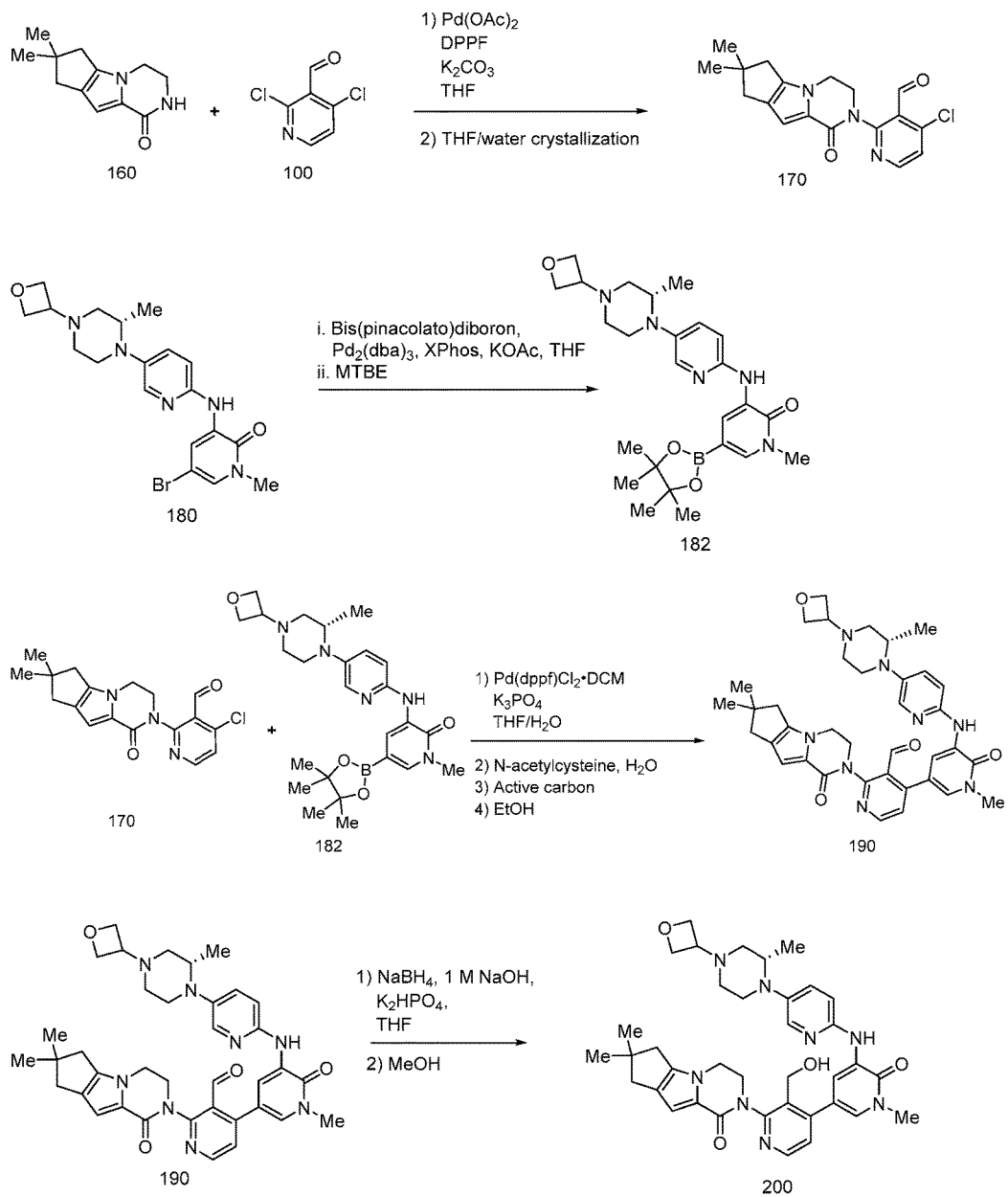
FIG. 2 shows a method for the preparation of compounds 170 and 182, and another method for the preparation of compounds 190 and 200.

In Example 10, compound 200 was prepared according to the methods depicted in FIGS. 1 and 2.

Example 10A

Compound 100 was prepared from compound 95 as follows:

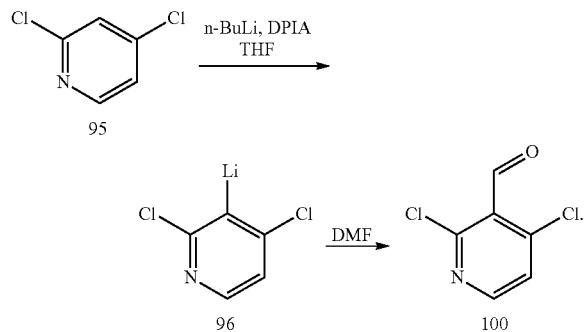

In a first method for preparing compound 100, a solution of n-BuLi (2.5M n-BuLi in hexane, 50.9 kg, 1.1 eq, addition rate of 44.3 g/min) and a solution of DIPA (diisopropylamine 26.7 kg in 70.6 kg of THF, 1.58 eq, addition rate of 84.7 g/min) were pumped into a tubular reactor via Y-mixer (stainless steel, Mixer I) with a residence time of 20-30 sec at −30° C. The resulting BuLi/DIPA mixture and a solution of compound 95 (2,4-dichloropyridine 24.7 kg in 45.9 kg of THF, 1.0 eq, addition rate 61.4 g/min) were pumped into a second tubular reactor via Y-mixer (stainless steel, Mixer II) with a residence time of 20-30 sec at −30° C. to form a solution of lithiated 2,4-dichloropyridine compound 96. The solution of compound 96 and a solution of DMF (dimethylformamide 34.2 kg, 2.8 eq, addition rate of 29.1 g/min) were pumped into a third tubular reactor via Y-mixer (stainless steel, Mixer III) with a residence time of 20-30 sec at −30° C. The reaction mixture was flowed through the outlet and collected in a quench reactor at 0-5° C., in which a quench solution (200.9 kg of 17% HCl solution, 5.5 eq) was filled in advance.

The quenched solution was heated at 20 to 25° C., and the phases were separated. The aqueous layer was mixed with toluene (171.3 kg), and the phases were separated. The two organic layers were combined, and washed with brine and water. The organic layer was concentrated at 50 to 60° C. and cooled to 40° C. Heptane (260.9 kg) was slowly added while maintaining a temperature of 40° C. A thick slurry was formed during heptane addition. It was cooled and aged for 2 hours at −20 to −15° C. The product was dried at full vacuum (Tj≤40° C.). 22.05 kg of compound 100 was obtained (75% yield from 2,4-dichloropyridine) as a brownish solid.

In a second method for preparing compound 100, n-BuLi (2.5 M in hexane, 90.3 kg, 332.0 mol, 1.4 eq) was added dropwise into a solution of DIPA (37.8 kg, 373.6 mol, 1.58 eq) in 100.0 kg of THF at between −30 to −15° C. over 60 min with stirring in a 500 L of stainless-steel reactor. The reaction mixture was stirred for 1-1.5 hr at between −30 to −15° C. and then cooled down to between −85 to −75° C. A solution of compound 95 (35.0 kg, 236.5 mol, 1.0 eq) in 65.0 kg of THF was added dropwise into the solution at less than −70° C. over about 60 min. The resulting solution was stirred at −80 to −70° C. for 1-2 hr. Then the reaction mixture was cooled down to −90° C. to −85° C., DMF (24.5 kg, 335.2 mol, 1.4 eq) was added at less than −70° C. over about 30-60 min. The reaction solution was added into aqueous HCl solution (16.9 w %, 284.0 kg) for quenching at less than 20° C. The quenched solution was extracted with ethyl acetate three times (95.0 kg+95.0 kg+35.0 kg). The combined organic layers were washed with brine (100.0 kg) and dried over with Na2SO4 (30.0 kg).

Three batches of organic phases were combined and concentrated under reduced pressure to 100 L volume at 60-65° C. Then the residue was cooled down to 35-40° C. and added petroleum ether (260.0 kg). The suspension was stirred for 1 h at less than 20° C., centrifuged and dried under vacuum at 40° C. for 4 h to afford 101.4 kg of the desired product as an off-white solid with 99.89% GC purity and 96.65 w % qNMR in 69.9% yield.

The effect of temperature and HCl concentration on compounds, 95, 96 and 100 were evaluated. The results are reported in Example 10 Table 1 below where "Exp." refers to experiment number, "Temp" refers to reaction temp in ° C., "Amt HCl" refers to the ratio of HCl volume (in liters) to compound 95 weight (in kg), "[HCl]" refers to HCl concentration (molar), "C 95" refers to compound 95 HPLC purity in area %, "C 96" refers to compound 96 HPLC purity in area %, and "C 100" refers to compound 100 HPLC purity in area %.

TABLE 1

Example 10

| Exp | Temp (° C.) | Amt HCl | [HCl] | C 95 | C 96 | C 100 |
|---|---|---|---|---|---|---|
| 1a | −10 to 0 | 5 V | 5M | 1.2 A % | 87.2 A % | 2.8 A % |
| 1b | | | 8M | 1.3 A % | 82.2 A % | 4.5 A % |
| 1c | | | 12M | 1.3 A % | 72.3 A % | 8.8 A % |
| 1d | | 7 V | 5M | 1.2 A % | 90.3 A % | 1.7 A % |
| 1e | | | 8M | 1.3 A % | 79.6 A % | 5.2 A % |
| 1f | | | 12M | 0.9 A % | 74.3 A % | 4.7 A % |
| 1g | | 10 V | 5M | 1.6 A % | 88.9 A % | 1.7 A % |
| 1h | | | 8M | 0.9 A % | 82.5 A % | 6.8 A % |
| 1i | | | 12M | 1.4 A % | 73.3 A % | 7.5 A % |
| 2a | 0 to 15 | 5 V | 5M | 1.1 A % | 85.3 A % | 3.6 A % |
| 2b | | | 8M | 0.9 A % | 80.6 A % | 4.2 A % |
| 2c | | | 12M | 1.9 A % | 72.9 A % | 8.7 A % |
| 2d | | 7 V | 5M | 0.9 A % | 89.2 A % | 1.2 A % |
| 2e | | | 8M | 1.3 A % | 86.4 A % | 5.6 A % |
| 2f | | | 12M | 1.8 A % | 74.3 A % | 7.2 A % |
| 2g | | 10 V | 5M | 0.9 A % | 88.1 A % | 2.5 A % |
| 2h | | | 8M | 1.6 A % | 84.4 A % | 2.6 A % |
| 2i | | | 12M | 1.3 A % | 79.3 A % | 6.0 A % |
| 3a | 10 to 25 | 5 V | 5M | 1.1 A % | 80.9 A % | 3.3 A % |
| 3b | | | 8M | 1.3 A % | 79.2 A % | 7.9 A % |
| 3c | | | 12M | 1.1 A % | 74.0 A % | 9.2 A % |
| 3d | | 7 V | 5M | 0.9 A % | 81.9 A % | 2.9 A % |
| 3e | | | 8M | 1.1 A % | 74.4 A % | 7.2 A % |
| 3f | | | 12M | 1.3 A % | 71.0 A % | 8.8 A % |
| 3g | | 10 V | 5M | 1.4 A % | 82.6 A % | 3.1 A % |

TABLE 1-continued

Example 10

| Exp | Temp (° C.) | Amt HCl | [HCl] | C 95 | C 96 | C 100 |
|---|---|---|---|---|---|---|
| 3h | | | 8M | 0.9 A % | 71.2 A % | 5.7 A % |
| 3i | | | 12M | 1.3 A % | 74.3 A % | 7.7 A % |

Example 10A-1

An alternative preparation of compound 100 is as follows (from compound 95 according to the same general reaction scheme shown above in Example 10A):

A solution of n-BuLi (2.5M n-BuLi in hexane, 467.9 kg, 1.1 eq) and a solution of DIPA (diisopropylamine 245.2 kg in 648.7 kg of THF, 1.58 eq) were pumped into a tubular reactor via Y-mixer (stainless steel, Mixer I) with a residence time of 20-30 sec at −20° C. to 0° C. The resulting mixture and a solution of compound 95 (2,4-dichloropyridine 227 kg in 421.4 kg of THF, 1.0 eq) were pumped into a second tubular reactor via Y-mixer (stainless steel, Mixer II) with a residence time of 20-30 sec at −30° C. to −20° C. to form a solution of lithiated 2,4-dichloropyridine compound 96. The solution of compound 96 and a solution of DMF (dimethylformamide 313.9 kg, 2.8 eq) were pumped into a third tubular reactor via Y-mixer (stainless steel, Mixer III) with a residence time of 20-30 sec at −30° C. to −20° C. The reaction mixture was flowed through the outlet and collected in a quench reactor at 0-5° C., in which a quench solution (1847 kg of 17% HCl solution, 5.5 eq) was filled in advance.

The quenched solution was heated at 20 to 25° C., and the phases were separated. The aqueous layer was mixed with toluene (1574 kg), and the phases were separated. The two organic layers were combined, and washed with brine (2.3V), twice with 4.8% NaHCO₃ (5V) and water (0.8V). The organic layer was concentrated at up to 60° C. and cooled to 40° C. Heptane (2398 kg) was slowly added while maintaining a temperature of 40° C. A thick slurry formed during heptane addition, which was then cooled and aged for 2 hours at −20 to about −15° C. The slurry was filtered, washed with a mixture of toluene (30.8 kg) and heptane (153.7 kg), and then washed with hexane (171.8 kg). The product was dried at full vacuum (Tj≤30° C.) for 12 hours. 234.6 kg of compound 100 was obtained (86.9% yield from 2,4-dichloropyridine) as a light yellow solid.

Example 10B

Compound 170 was prepared from compounds 160 and 100 as follows:

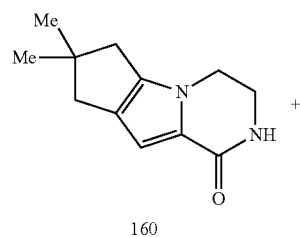

160

+

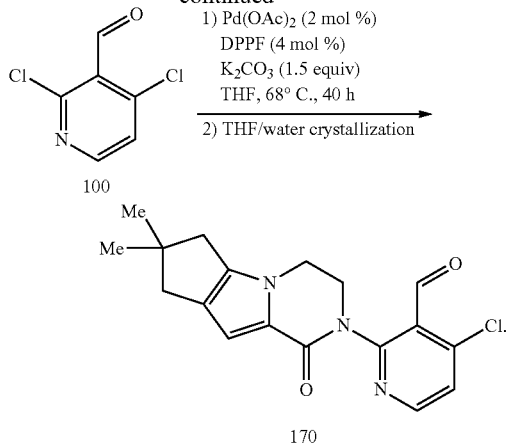

Potassium carbonate (20.3 g, 1.5 eq., 147 mmol), compound 100 (19 g, 1.1 eq., 108 mmol), compound 160 (20 g, 1 eq., 97.9 mmol), DPPF ligand (2.2 g, 0.04 eq., 3.9 mmol), and Pd(OAc)₂ catalyst (0.44 g, 0.02 eq., 2 mmol) were charged to a reactor. THF (200 mL, 10 mL/g) was charged to the reactor with agitation. The reactor was evacuated and filled with N₂ three times and the contents were then heated to 68° C. with reflux. The reactor was sampled at 22 hours and the compound 160 content was 0.9 area % by HPLC. The reactor contents were cooled to 65° C. and water (200 mL, 10 mL/g) was charged to the reactor over 4 hours and the reactors contents were then held at 20° C. for a minimum of 3 hours. The reactor contents were filtered and compound 170 was collected as a solid. The solid compound 170 was rinsed with THF/water (1:1 mixture, 200 mL, 10 mL/g). The washed solids were dried under vacuum with N₂ purge at 22° C. for a minimum of 3 hours. A yield of 84% was obtained with 99 area % by HPLC (245 nm), 79 ppm Pd and 0.2% residue on ignition ("ROI"). Of the impurities, 0.51 A % regioisomer and 0.33% bis-coupling product were found:

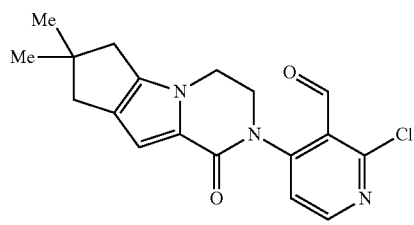

Regioisomer

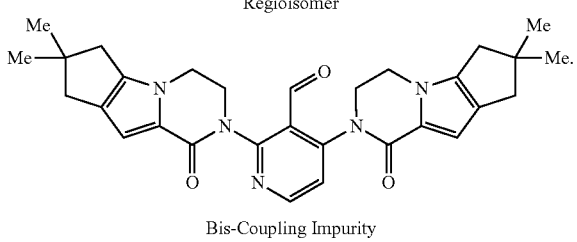

Bis-Coupling Impurity

The method was repeated on a 40 g scale (based on compound 160). The coupling reaction was performed using compound 100 (1.1 eq.), Pd(OAc)₂ (0.02 eq.), dppf in THF (0.04 eq., 10 mL/g) at 68° C. for 28 h to reach 98.4% conversion. Water was added (350 mL) to the reaction mixture over 3 h and aged at 65° C. for 10 h, cooled to 20°

C. in 1.5 h and aged for 16 h. After filtration and drying, a beige solid compound 170 was obtained (57.2 g, 85%, 98.6 A %, 0.55 A % regioisomer, 0.48 A % bis-coupling impurity, 87 ppm Pd and 0.3% ROI).

The method was repeated on a 609 g scale (based on compound 160). Potassium carbonate (0.6114 kg, 1.5 eq., 4.34 mol), compound 100 (0.7769 kg, 1.5 eq., 4.41 mol), compound 160 (0.6099 kg, 1 eq., 2.99 mol), DPPF ligand (0.0662 kg, 0.04 eq., 0.119 mmol), and Pd(OAc)$_2$ catalyst (0.0137 kg, 0.02 eq., 0.061 mmol) were charged to an isolator. A reactor was evacuated and filled with N$_2$ three times and charged with the contents of the isolator. THF (10.35 kg, 20 L/kg) was charged to the reactor with agitation. The reactor contents were heated to 68° C. with reflux. The reactor was sampled at 40 hours and the compound 160 content was 0.3 area % by HPLC. The reactor contents were cooled to 65° C. and water (6.01 kg, 10 L/kg) was charged to the reactor over 3 hours and the reactor contents were then held at 20° C. for a minimum of 3 hours. The reactor contents were filtered and compound 170 was collected as a solid. The solid compound 170 was rinsed with THF/water (1:1 mixture, 6 L, 10 mL/g). The washed solids were dried under vacuum with N$_2$ purge at 22° C. for a minimum of 10 hours. A 84% yield (0.8576 kg) was obtained with 99.2 A % by HPLC (245 nm), 24 ppm Pd and less than 0.1% ROI.

Example 10C

Compound 182 was prepared from compound 180 as follows:

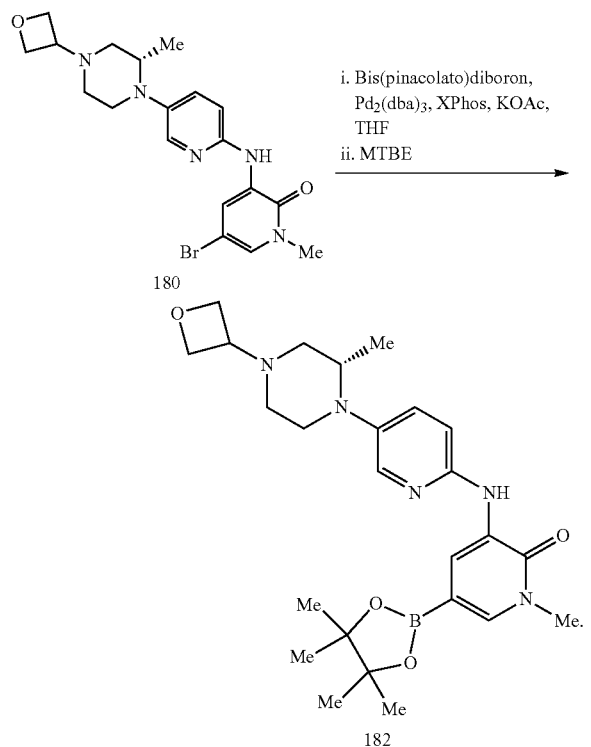

Compound 180 (1.2 kg, 2.763 mol, 1 eq.), bis(pinacolato)diboron (1.052 kg, 4.145 mol, 1.5 eq.), KOAc (0.542 kg, 5.526 mol, 2 eq.) were charged to an inerted reactor. Excess THF (15 L) was charged to a holding vessel and was sparged subsurface with N$_2$ for at least 1 hour to form degassed THF. Degassed THF (9.78 kg, 11 L) was charged to the reactor with agitation. Pd$_2$(dba)$_3$ (6.52 g, 6.91 mmol, 0.0025 eq.), XPhos (8.15 g, 16.58 mmol, 0.006 eq.) and degassed THF (0.445 kg, 0.5 L) were combined with agitation to form a mixture in a catalyst preparation vessel. The catalyst mixture was then added to the reactor with agitation. The contents of the reactor were sparged subsurface with N$_2$ for a minimum of 1 hour. The contents of the reactor were heated to 60 to 70° C. and aged for a minimum of 12 hours. The contents of the reactor were sampled and evaluated for compound 170 content by HPLC, and the reaction was continued until the compound 170 content was 0.9 area % by HPLC. The reactor contents were cooled to 20 to 30° C. to form a crude reaction mixture comprising compound 182. Water (3.6 kg, 3 L/kg) was charged to the reactor and the reactor contents were agitated for a minimum of 10 minutes. The aqueous layer was removed from the reactor. The organic layer remaining in the reactor may be optionally washed with brine. The reactor contents were heated to 55 to 65° C. and vacuum distilled to 4 L (3.3 L/kg). THF (7.11 kg, 8 L, 6.7 L/kg) was charged to the reactor, and the reactor contents were heated to 55 to 65° C. and vacuum distilled to 4 L (3.3 L/kg). The THF/distillation step was repeated. The THF/distillation step may be further repeated, as necessary, to reduce the water content in the reactor contents to no more than 3%. The reactor contents were filtered through celite (0.2 kg) followed by a THF rinse (1.1 kg, 1.2 L, 1 L/kg) to produce a filtrate comprising compound 182. The filtrate was heated to 55 to 65° C. and was vacuum distilled at a temperature of at least 40° C. to a reduced volume of 2 to 3 L. MTBE (8.9 kg, 10 L/kg) was charged to the reduced volume and the resulting mixture was vacuum distilled at a temperature of at least 40° C. to a reduced volume of 2 to 3 L. MTBE (8.9 kg, 10 L/kg) was charged to the reduced volume and the resulting mixture comprising compound 182 was aged at 50 to 60° C. for 2 hours followed by cooling to 0 to 10° C. and aging for a minimum of 2 hours. The mixture was filtered and compound 182 was collected as a filter cake. The filter cake was washed with MTBE (1.86 kg, 2 L/kg) twice. The isolated compound 182 solids were dried under reduced pressure at 50° C. with N$_2$ sweep for a minimum of 15 hours to provide compound 182 (1.334 kg, 90.3 w/w %, 6.2 wt % THF, 2 wt % MTBE, 1.2% ROI, 90.6% yield).

The major impurities were a DesBr impurity and a Dimer impurity as follows:

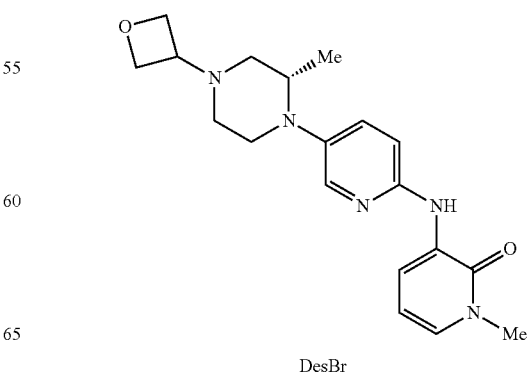

DesBr

-continued

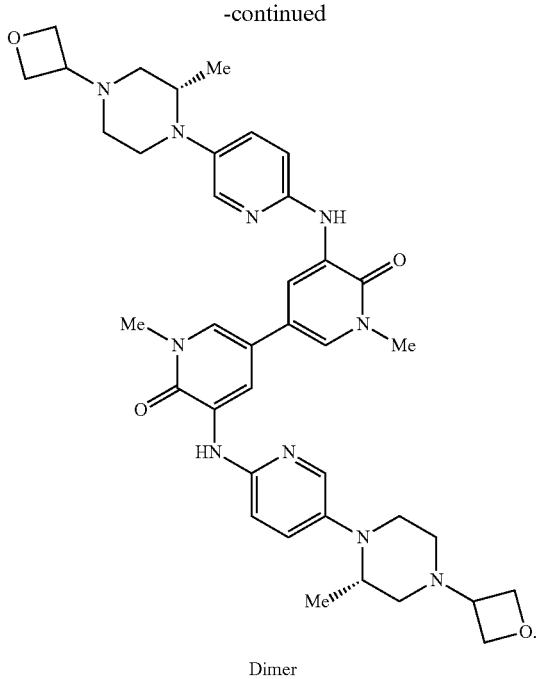

Dimer

The crude reaction mixture contained from 0.5% to 1% DesBr and from 0.1% to 0.5% dimer and the isolated solids contained from 0.1% to 0.4% DesBr and from 0 to 0.1% dimer.

The above method for preparing compound 180 from compound 170 was repeated without the MTBE charge and distillation step. Compound 180 at 92.7 w/w % comprising 2.4 wt % THF, 6.7 wt % MTBE, 0.6% ROI and 90.1% yield was produced.

Example 10D

Compound 190 was prepared from compounds 170 and 182 as follows:

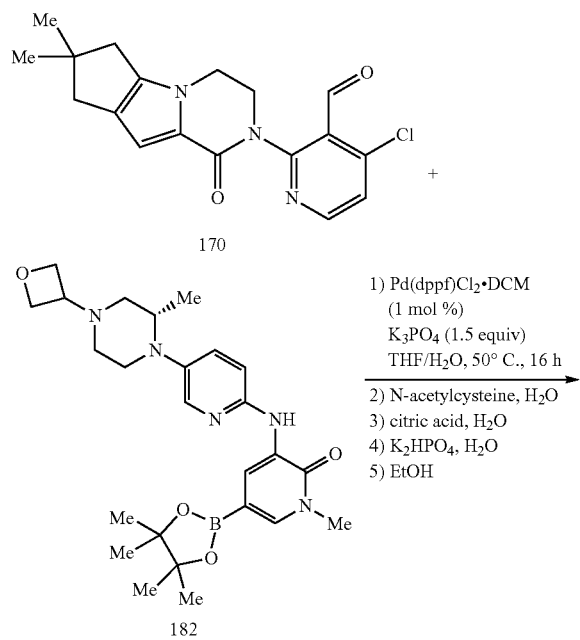

-continued

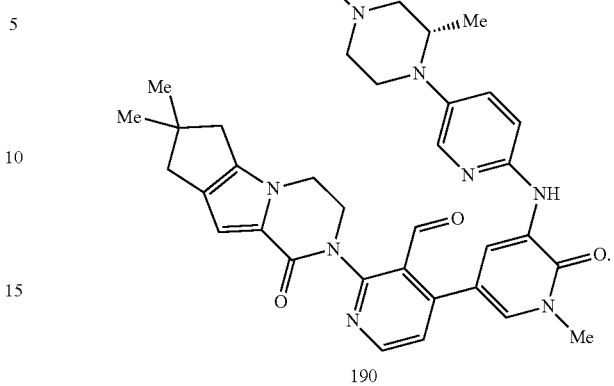

190

In a first evaluation, compound 170 (50 g, 144 mmol, 1 eq.) and compound 182 (83.51 g, 158.4 mmol, 1.1 eq.) were charged to a reactor and the reactor was inerted by cycling from vacuum to $N_2$ three times. Potassium phosphate tribasic monohydrate (51.79 g, 216 mmol, 1.5 eq.) and water (100 mL, 100 g, 2 mL/g) were charged to a vessel to form a solution and the vessel was inerted by cycling from vacuum to $N_2$ three times. The potassium phosphate solution was charged to the reactor under $N_2$, the reactor was inerted by cycling from vacuum to $N_2$ three times, and the reactor contents were agitated for a minimum of 10 minutes. 1,1'-Bis(diphenlphosphino)ferrocene Palladium(II)dichloride dichloromethane complex (1.2 g, 0.01 equiv, 1.44 mmol) was charged to the reactor and the reactor was inerted by cycling from vacuum to $N_2$ three times. The reactor contents were heated to 45 to 55° C. for a minimum of 8 hours to form crude compound 190. A sample was taken after 16 hours and indicated less than 0.1 area % compound 170.

The reactor contents were cooled to 20 to 25° C., 6 wt. % N-acetyl-L-cysteine (100 mL, about 0.25 eq.) was charged to the reactor, and the reactor contents were stirred for at least 15 minutes. An aqueous phase was separated and removed from the reactor leaving an organic phase in the reactor. The organic phase was combined with 26 wt. % aqueous brine solution (100 mL, 2 mL/g) with agitation. An aqueous phase was separated and removed from the reactor leaving an organic phase in the reactor. The reactor contents were distilled to 250 mL (5 mL/kg) under vacuum at 45 to 60° C.

THF (250 mL, 5 mL/g) was charged to reactor and the reactor contents were distilled to 250 mL (5 mL/kg) under vacuum at 45 to 60° C. The THF addition and distillation step was repeated except the final volume was 300 mL (6 mL/g). THF (200 mL, 4 mL/g) was charged to the reactor and the reactor contents were found to have a water content of 1.7%. The reactor contents were cooled to 35 to 45° C., Ecsorb C-948 activated carbon (10 g, 20% g/g) was charged to the reactor, the reactor contents agitated for 16 hours at 35 to 45° C. The reactor contents were cooled to 15 to 25° C. and the reactors contents were filtered through celite. The reactor was rinsed forward through the filter with THF (50 mL, 1 mL/g) three times. The filtrates were combined, heated in a reactor to 55 to 65° C., and distilled to 250 mL under vacuum. Ethanol (250 mL, 5 mL/g) was added to the reactor followed by distillation to 250 mL under vacuum at 45 to 65° C. This step was repeated. Ethanol (250 mL, 5 mL/g) was charged to the reactor followed by distillation to 450 mL. Precipitated compound 190 solids were observed. Compound 190 seed crystals may optionally be added at this point. The reactor contents were assayed for THF/ethanol ratio and the result was 0.5%. The reactor contents were aged at 55 to 65° C. for at least 2 hours, the contents were cooled to 15 to 25° C. over 2 hours, and the contents were aged at 15 to 25° C. for a minimum of 6 hours to crystallize compound 190. Crystallized compound 190 was collected by filtration. The collected compound 190 solids were washed with ethanol (100 mL, 2 mL/g) three times. The compound 190 solids were dried under vacuum at 45 to 55° C. for at least 16 hours to provide 88.7 g compound 190 (93% yield), 99.6 area % purity, 98.7 w/w %, 0.18 area % dimer impurity and 0.08 area % regioisomer impurity. The dimer and regioisomer structures are as follows:

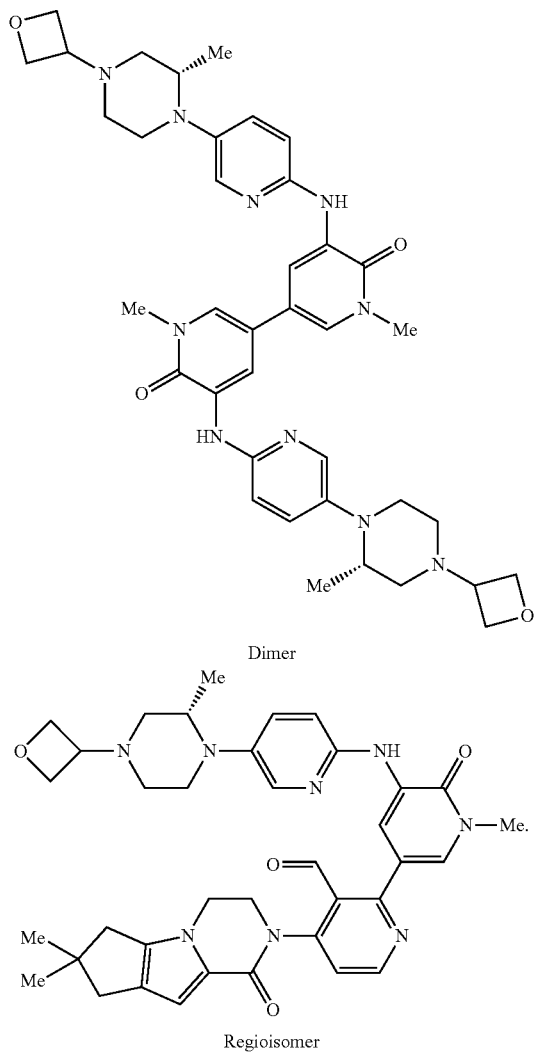

In a second evaluation, crude compound 190 was prepared generally in accordance with the method of the first evaluation above starting with 0.75 kg of compound 170. A sample taken after 16 hours and prior to work-up indicated less than 0.1 area % compound 170. Crude compound 190 was worked up as follows. The reactor contents were cooled to 20 to 25° C., 6 wt. % N-acetyl-L-cysteine (1.5 L, 1.5 kg, about 0.25 eq.) was charged to the reactor, and the reactor contents were stirred for at least 15 minutes. An aqueous phase was separated and removed from the reactor leaving an organic phase in the reactor. 5 wt % aqueous citric acid solution (0.75 L, 0.75 kg, 1 L/kg) was charged to the reactor. 26 wt % aqueous brine solution (0.75 L, 0.9 kg, 1 L/kg) was added to the reactor with agitation. An aqueous phase was separated and removed from the reactor leaving an organic phase in the reactor. 26 wt % aqueous brine solution (2.25 L, 2.7 kg, 3 L/kg) was added to the reactor with agitation. An aqueous phase was separated and removed from the reactor leaving an organic phase in the reactor. 26 wt % aqueous brine solution (1.5 L, 1.8 kg, 2 L/kg) was added to the reactor with agitation. An aqueous phase was separated and removed from the reactor leaving an organic phase in the reactor. 60 wt % $K_2HPO_4$ aqueous solution (0.75 L, 1 L/kg) and 26 wt % aqueous NaCl solution (2.25 L, 2.7 kg, 3 L/kg) were charged to the reactor and the contents were agitated for a minimum of 10 minutes. An aqueous phase was separated and removed from the reactor leaving an organic phase in the reactor.

THF (7.5 L, 10 L/kg) was charged to the reactor and the reactor contents were heated to 55 to 65° C. and distilled to 6 L under vacuum. THF (3.75 L, 5 L/kg) was charged to the reactor and the reactor contents were distilled to 6 L under vacuum. The reactor contents were cooled to 30 to 40° C. and were filtered through celite. The reactor was rinsed forward through the filter with THF (1.5 L, 1.35 kg, 2 L/kg). The filtrates were combined, and heated in a reactor to 55 to 65° C. and distilled to 4 L under vacuum. Ethanol (5.25 L, 4.14 kg, 7 L/kg) was added to the reactor followed by distillation to 4 L under vacuum at 45 to 65° C. This step was repeated except distillation was to 6 L. Precipitated compound 190 solids were observed. Compound 190 seed crystals may optionally be added at this point. Ethanol (5.25 L, 4.14 kg, 7 L/kg) was added to the reactor followed by distillation to 6 L under vacuum at 45 to 65° C. The reactor contents were assayed for THF/ethanol ratio and the result was 0.1%. The reactor contents were aged at 55 to 65° C. for at least an hour, the contents were cooled to 15° C. over 4 hours, and the contents were aged at 15° C. for a minimum of 6 hours to crystallize compound 190. Crystallized compound 190 was collected by filtration. The collected compound 190 solids were washed with ethanol (1.5 L, 1.18 kg, 2 L/kg) three times. The compound 190 solids were dried under vacuum at 45 to 55° C. for at least 16 hours to provide 1.26 kg compound 190 (88% yield), 99.4 area % purity, 98.3 w/w %, 0.15 area % dimer impurity and 0.04 area % regioisomer impurity.

Example 10E

Compound 200 was prepared from compound 190 as follows:

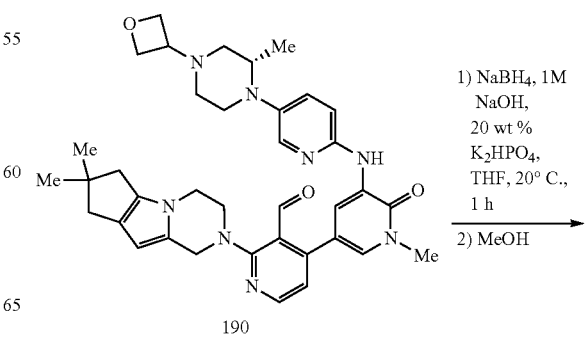

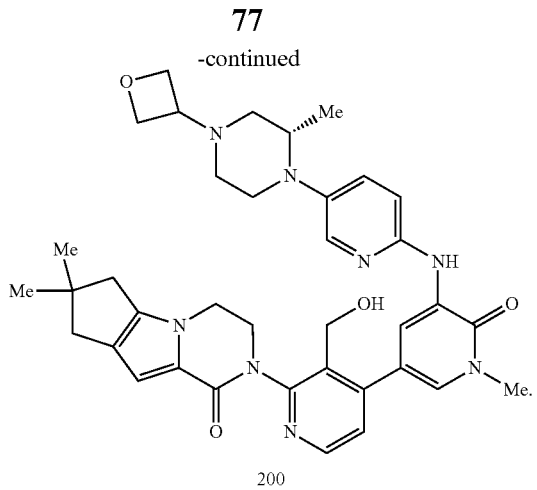

200

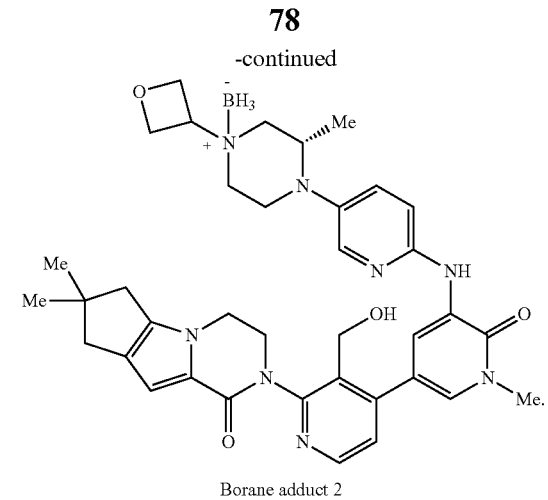

Borane adduct 2

Compound 190 (1.16 kg, 1.75 mol, 100 wt. %) was charged to a reactor. THF (7.2 L, 6 L/kg) was sparged in a vessel subsurface with $N_2$ for at least 30 minutes to form degassed THF. The degassed THF was charged to the reactor with agitation. 20 wt % aqueous $K_2HPO_4$ (0.6 L, 0.5 L/kg) was sparged in a vessel subsurface with $N_2$ for a minimum of 15 minutes, and was then charged to the reactor followed by agitation at 20 to 26° C. for at least 20 minutes. Sodium hydroxide 1M aqueous solution (0.6 L, 0.5 kg) was sparged in a vessel subsurface with $N_2$ for a minimum of 20 minutes, and sodium borohydride (34.2 g, 0.5 eq., 0.91 mol) was then combined with the sodium hydroxide. The sodium hydroxide/sodium borohydride admixture was then charged to the reactor while maintaining the contents of the reactor at from 20 to 30° C. The reactor contents were agitated under a $N_2$ blanket at 20 to 26° C. for at least 1 hour to produce a mixture comprising crude compound 200. The concentration of compound 190 in the mixture was 0.1 area %.

16 wt % aqueous $KH_2PO_4$ (1.44 L, 1.2 L/kg) was charged to a vessel and sparged subsurface with $N_2$ for at least 15 minutes to form a degassed solution. The mixture comprising crude compound 200 in the reactor was heated to 25 to 35° C. and the degassed solution of $KH_2PO_4$ was charged to the reactor at 25 to 35° C. followed by heating to 35 to 45° C. and agitation at temperature for at least 1 hour. The temperature was reduced to 20 to 26° C. and an aqueous phase was separated and removed from the reactor leaving an organic phase in the reactor. 15 wt % aqueous NaCl solution (3.6 L, 3 L/kg) was charged to the reactor, the contents were heated to 45 to 55° C., and the contents were agitated for at least 1 hour. The reactor contents were sampled and evaluate for borane adduct content which was determined to be 0.1 area % where the borane adduct is believed to be of the structures:

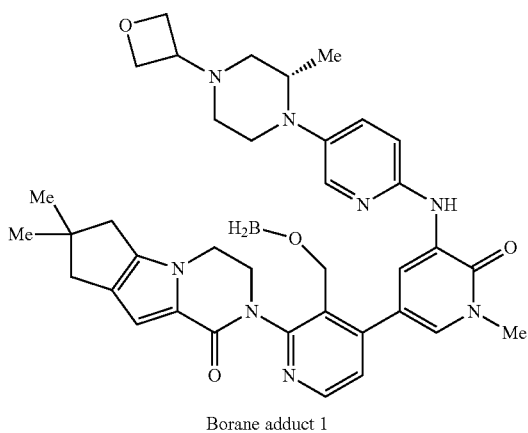

Borane adduct 1

The reactor contents were cooled to 20 to 26° C. and an aqueous phase was separated and removed from the reactor leaving an organic phase in the reactor. The reactors contents were heated to 35 to 45° C. and were filtered through celite. The reactor was rinsed forward through the filter with THF (2.4 L, 2 L/kg). The filtrates were combined in a reactor and were distilled under vacuum at 35 to 40° C. to a total volume of 3 L/kg. Methanol (8.4 L, 7 L/kg) and compound 200 seed crystals (6.1 g, 0.5 wt % in a slurry of 50 mL methanol) were charged to the reactor, and the reactor contents were aged at 30 to 40° C. for 1 hour. The reactor contents were distilled under vacuum to a total volume of 5 L/kg. The reactor contents were heated to 55° C. and aged for at least 1 hour followed by cooling to 15° C. over 4 hours. The reactor contents were held at 15° C. for at least 6 hours to crystallize compound 200. The reactor contents were filtered to collect compound 200 solids and the reactor was washed forward through the compound 200 solids collected on the filter with methanol (2.4 L, 2 L/kg) twice. The compound 200 solids were dried under vacuum with a $N_2$ purge for 12 hours to provide crude compound 200 (991.2 g, 85.2% isolated yield).

Example 10F

Crude compound 200 (0.778 kg, 1.17 mol), ethanol (4.14 kg, 6.75 L/kg) and toluene (1.52 kg, 2.25 L/kg) were charged to a reactor and agitation was started. Crude compound 200 had an assay of 98.4 w/w %, and a purity of 99.6 area % by HPLC. The reactor contents were heated to 65 to 85° C. until a clear solution was obtained. The solution was cooled to 60 to 70° C. and compound 200 seed crystals (7.4 g, 1 wt %, in 200 mL ethanol) were charged to the reactor. The reactor contents were aged for at least 1 hour and ethanol (10.24 kg, 15 L/kg) was added to the reactor of a minimum of 2 hours. The reactor contents were cooled to 5 to 15° C. over a minimum of 4 hours and held overnight to crystallize compound 200. The crystallized compound 200 was filtered and the collected compound 200 solids were dried under vacuum with $N_2$ purge at 50° C. for 22 hours to provide purified compound 200 (641.5 g, 82.4% yield). Purified compound 200 had an assay of 97.6 w/w % and a purity of 99.9 area % by HPLC.

Example 11

Alternatively, compound 200 may be prepared from compound 170 and compound 182 as follows:

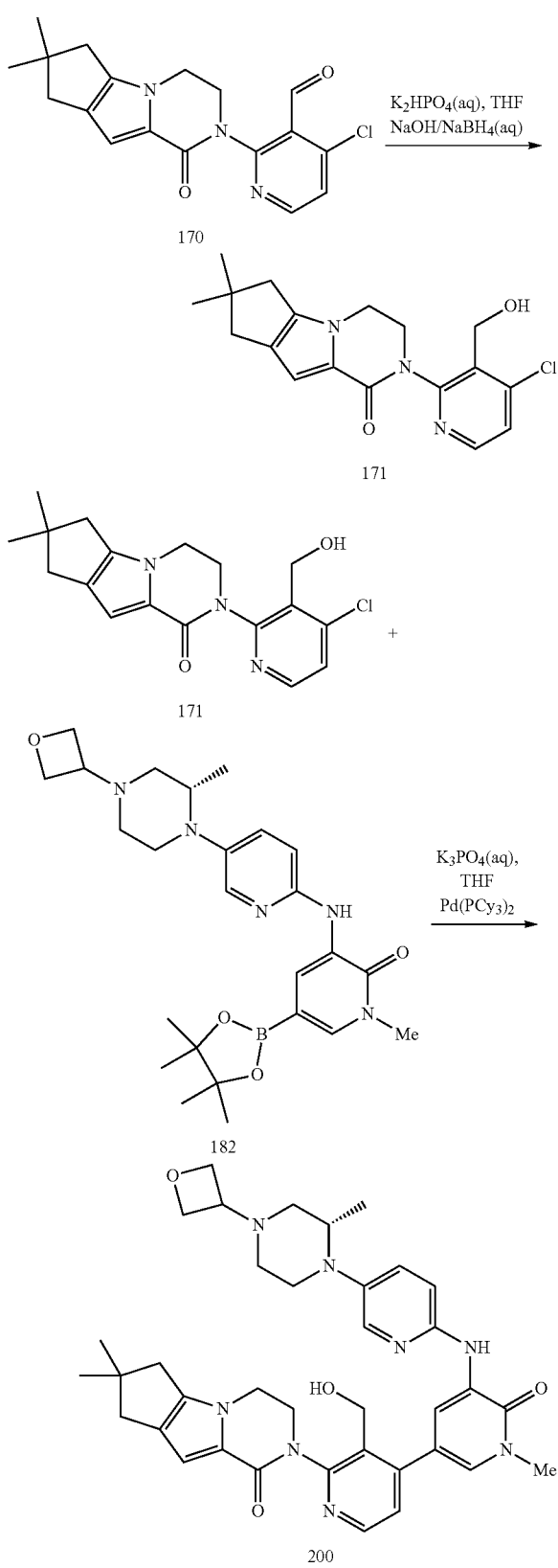

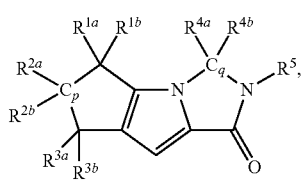

phosphate dibasic (23.8 g, 136 mmol, 0.469 equiv) and water (42.5 mL). The mixture was heated to 58° C. and a solution of 12% w/w NaBH4 (aq)/40% w/w in NaOH (aq) (27.5 g, 20.0 mL, 87.3 mmol, 0.30 equiv) was added over 40 minutes. Upon completion of the reaction (typically 2-3 hours), the mixture was quenched by the addition of 85% aq. phosphoric acid (30.8 g, 18.3 mL, 267 mmol, 0.918 equiv). The mixture was diluted with water (50 mL) and toluene (290 mL) and stirred for 10 minutes. The phases are separated, the organic layer was washed with aqueous sodium hydroxide 1 M (40 mL) and the layers were separated. The organic layer was solvent swapped to toluene at atmospheric pressure and the resulting suspension was cooled to 0° C. The crystals were filtered off, washed twice with each 115 mL toluene and dried under reduced pressure. Compound 171 was isolated as off-white crystals in 78% yield.

A 100-mL double-jacketed reactor was charged with Compound 171 (10.0 g, 28.9 mmol, 1.00 equiv), Compound 182 (15.3 g, 31.8 mmol, 1.10 equiv), potassium phosphate tribasic (9.21 g, 43.4 mmol, 1.10 equiv), THF (71 mL), and water (20 mL) under inert atmosphere. The mixture was degassed under stirring by repeated vacuum-nitrogen cycles. A solution of Pd(PCy$_3$)$_2$ (193 mg, 0.289 mmol, 1.00 mol %) in THF (5 mL) was added. The mixture was heated to 50° C. and stirred at this temperature until the desired conversion is reached. The reaction mixture was cooled to 45° C. and a solution of N-acetyl cysteine (1.18 g, 7.23 mmol, 0.25 equiv) in water (60 mL) is added. After stirring for 30 minutes, the layers were separated and the organic layer was washed twice with each 16 mL aq. NaOH 1M and once with water (33 mL). The organic layer was dried azeotropically by THF distillation at constant volume at 300 mbar and subsequently filtered over charcoal at 45° C. Following solvent swap to ethanol, crystallization of Compound 200 was observed. The crystals were filtered off and dried under reduced pressure, giving 13.4 g (70% yield) of Compound 200 as off-white crystals.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:
1. A method for preparing a tricyclic lactam of formula 400, stereoisomers thereof, geometric isomers thereof, tautomers thereof, and salts thereof, the method comprising forming a reaction mixture comprising an organic solvent, an organic base, and formulas 300 and 310

A 500-mL double jacketed reactor was charged with compound 170 (100 g, 291 mmol, 1.00 equiv) and THF 8600 mL). To this stirred suspension were added potassium

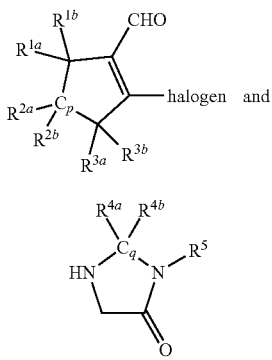

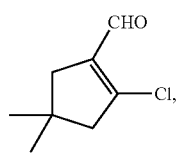

and formula 310 is piperazine-2-one of formula 10:

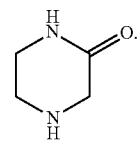

and reacting the reaction mixture to form a reaction product mixture comprising the tricyclic lactam of formula 400, wherein:

$R^{1a}$, $R^{1b}$, $R^{2a}$, $R^{2b}$, $R^{3a}$, $R^{3b}$, $R^{4a}$ and $R^{4b}$ are independently selected from H, and $C_{1-6}$ alkyl; $R^5$ is selected from H, $C_{1-6}$ alkyl, cycloalkyl, aryl, substituted aryl, benzyl, substituted benzyl, heteroaryl, and substituted heteroaryl;

p is 1, 2, 3 or 4; and q is 1, 2, 3 or 4.

2. The method of claim 1 wherein p is 1 or 2, and q is 1 or 2.

3. The method of claim 1 wherein the organic base is a tri-$C_{1-6}$ alkyl amine.

4. The method of claim 3, wherein the organic base is selected from 4-methylmorpholine and N-ethyldiiopropylamine.

5. The method of claim 1 wherein the solvent is a polar aprotic solvent.

6. The method of claim 5 wherein the solvent is selected from N-methylpyrrolidone and dimethylformamide.

7. The method of claim 1 wherein halogen is Cl.

8. The method of claim 1 wherein p is 1 and q is 2.

9. The method of claim 1 wherein $R^{1a}$, $R^{1b}$, $R^{3a}$, $R^{3b}$, $R^{4a}$, $R^{4b}$ and $R^5$ are H, and $R^{2a}$ and $R^{2b}$ are —$CH_3$.

10. The method of claim 1 wherein the reaction mixture comprises from about 0.25 to about 2 moles per liter of formula 300; between 1 and 2 equivalents base; and between 0.7 and 1 equivalents of formula 310.

11. The method of claim 1 wherein the tricyclic lactam of formula 400 is species formula 160 of the structure:

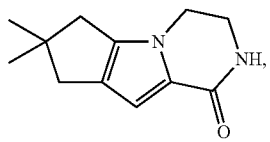

formula 300 is the species of formula 130 of the structure:

12. The method of claim 1 wherein formula 300 is prepared by forming a reaction mixture comprising a polar aprotic solvent, a non-polar solvent, phosphorous oxychloride and formula 320:

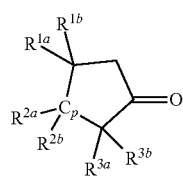

and reacting the reaction mixture to form a reaction product mixture comprising formula 300.

13. The method of claim 12 wherein the polar aprotic solvent is dimethylformamide, the non-polar solvent is dichloromethane, the mole ratio of phosphorous oxychloride to formula 320 is from about 1.5:1 to about 2.7:1, and the mole ratio of the polar aprotic solvent to formula 320 is from about 1.5:1 to about 3.5:1.

14. The method of claim 12 wherein compound 320 is the subgenus compound 321 wherein $R^{1a}$ and $R^{1b}$ are each independently selected from the group consisting of H and $C_{1-6}$ alkyl;

$R^{2a}$ is —$CH_3$;

$R^{2b}$ is selected from the group consisting of H and $C_{1-6}$ alkyl;

$R^{3a}$ and $R^{3b}$ are each H;

p is 1; and wherein compound 321 is prepared by forming a reaction mixture comprising a polar aprotic solvent, methyl magnesium chloride, copper (I) chloride and compound 330 and reacting the reaction mixture to form a reaction product mixture comprising compound 321 according to the following reaction scheme:

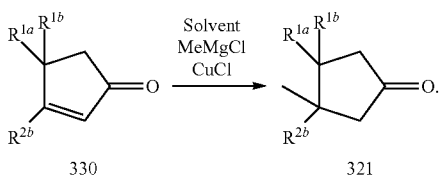

15. The method of claim 12 wherein
$R^{1a}$, $R^{1b}$, $R^{3a}$ and $R^{3b}$ are H, p is 1, and $R^{2a}$ and $R^{2b}$ are —CH$_3$,
wherein compound 321 is the species of compound 120 prepared by forming a reaction mixture comprising a polar aprotic solvent, methyl magnesium chloride, copper (I) chloride and compound 110:

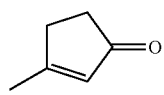

and reacting the reaction mixture to form a reaction product mixture comprising compound 120

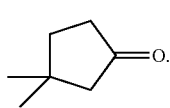

16. The method of claim 15 wherein the solvent is tetrahydrofuran, the mole ratio of methyl magnesium chloride to compound 110 in the reaction mixture is between 1:1 and 2:1, and the mole ratio of copper (I) chloride to compound 110 in the reaction mixture is from about 0.1:1 to about 0.5:1.

17. The method of claim 12 further comprising purifying compound 320, the purification comprising:
(i) forming a first reaction mixture comprising crude compound 320, an organic solvent that is not miscible with water, and an aqueous solution of sodium bisulfite, and reacting the first reaction mixture to form a first reaction product mixture comprising the solid ketone bisulfite adduct of compound 340:

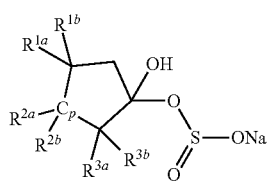

(ii) isolating solid compound 340 from the first reaction product mixture,
(iii) forming a second reaction mixture comprising isolated compound 340, water, a low boiling solvent that is not miscible with water, and sodium bicarbonate, and reacting the second reaction mixture to form a second reaction product mixture comprising a first phase comprising dichloromethane and the predominant amount of purified compound 320 is in solution in the first phase, and a second phase comprising water, and
(iv) separating the first phase comprising the purified compound 320 from the aqueous phase.

18. The method of claim 17 wherein:
(i) crude compound 320 is in solution in organic solvent that is not miscible with water, the ratio of water volume to the crude compound 320 weight in the first reaction mixture is from about 1:1 L/kg to about 10:1 L/kg, and the equivalent ratio of sodium bisulfite to compound 320 in the first reaction mixture is from about 2:1 to about 5:1;
(ii) the second reaction mixture comprises a ratio of water volume to isolated solid 340 weight of from about 5:1 L/kg to about 15:1 L/kg, the ratio of water volume to the low boiling solvent volume that is not miscible with water in the second reaction mixture is from about 1:1 to about 3:1, and the equivalent ratio of sodium bicarbonate to compound 340 in the second reaction mixture is between 1:1 and 2:1, and
(iii) the yield of purified compound 320 is at least 60% based on compound 330 and the purity of purified compound 330 is at least 98%.

19. The method of claim 17 wherein the organic solvent that is not miscible with water in the first reaction mixture is a hexane, and wherein the low boiling solvent that is not miscible with water in the second reaction mixture is dichloromethane.

20. The method of claim 1 wherein,
$R^{1a}$ and $R^{1b}$ are each independently selected from the group consisting of H and $C_{1-6}$ alkyl;
$R^{2a}$ is —CH$_3$;
$R^{2b}$ is selected from the group consisting of H and $C_{1-6}$ alkyl;
$R^{3a}$ and $R^{3b}$ are each H;
p is 1; and
wherein compound 300 is prepared by:
(i) forming a first reaction mixture comprising a first polar aprotic solvent, methyl magnesium chloride, copper (I) chloride, lithium chloride, chlorotrimethylsilane, and compound 330:

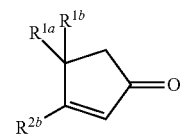

and reacting compound 330 to form a first reaction product mixture comprising compound 335 where $R^{2a}$ is —CH$_3$

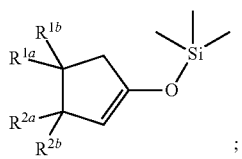

(ii) quenching the first reaction product mixture with methanol as a first quenching agent;

(iii) further quenching with a second quenching agent in aqueous solution and adding a non-polar water-immiscible solvent to the quenched reaction product mixture;
(iv) separating the phases and collecting the organic phase comprising the predominant amount of compound 335 and concentrating the organic phase to obtain compound 335 in solution;
(v) forming a second reaction mixture comprising a second polar aprotic solvent, phosphorous oxychloride, and the solution of compound 335, and reacting the second reaction mixture to form a second reaction product mixture comprising compound 301 of the structure

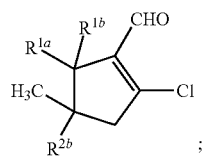

301

(vi) quenching the second reaction product mixture with a third quenching agent in aqueous solution; and
(vii) separating the phases and collecting the organic phase comprising the predominant amount of compound 301 in solution.

21. The method of claim 20 wherein the first polar aprotic solvent is tetrahydrofuran, the second quenching agent is ammonium chloride, the non-polar water-immiscible solvent is toluene, the second polar aprotic solvent is dimethylformamide, and the third quenching agent is potassium phosphate.

22. The method of claim 20 wherein:
(i) the first reaction mixture comprises: from about 0.25 to about 2 moles per liter of compound 330; a stoichiometric excess of methylmagnesium chloride as compared to compound 330; a mole ratio of methylmagnesium chloride to compound 330 of between 1:1 and 1.5:1; a stoichiometric excess of chlorotrimethylsilane as compared to compound 330; a mole ratio of chlorotrimethylsilane to compound 330 of between 1:1 and 1.2:1; a mole ratio of copper (I) chloride to compound 330 of from about 0.05:1 to about 0.2:1; and a mole ratio of lithium chloride to compound 330 of from about 0.05:1 to about 0.2:1,
(ii) the second reaction mixture comprises: from about 0.5 to about 2 moles per liter compound 335; and a mole ratio of phosphorous oxychloride to compound 335 of from about 1.5:1 to about 3.1:1, and
(iii) the yield of compound 300 based on compound 330 is at least 70%, and the purity of compound 301 is at least 85%.

23. The method of claim 20 wherein $R^{1a}$ and $R^{1b}$ are each H and $R^{2b}$ is —$CH_3$.

24. The method of claim 11 further comprising preparing compound 170 by:
(i) forming a reaction mixture comprising compound 160, a stoichiometric excess of compound 100, a palladium catalyst and a catalyst ligand, a base and a polar aprotic solvent, and
(ii) reacting the reaction mixture to form a reaction product mixture comprising compound 170 according to the following scheme:

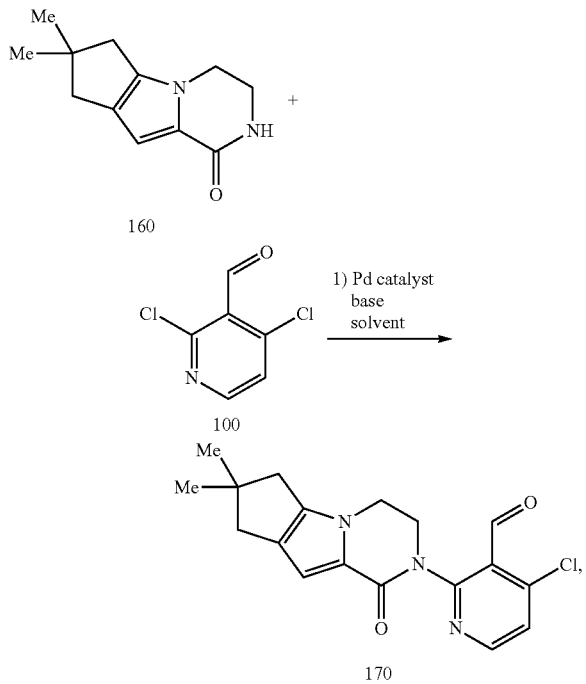

and
(iii) isolating compound 170 from the reaction product mixture,
wherein the yield of compound 170 based on compound 160 is at least 80%, and wherein the purity of compound 170 is at least 95%.

25. The method of claim 24 wherein the ratio of the solvent volume to compound 160 weight in the reaction mixture is from about 5:1 to about 20:1 liters per kg, and wherein the equivalent ratio of catalyst to compound 160 is from about 0.01:1 to about 0.03:1.

26. The method of claim 25 wherein the catalyst is Pd(OAc)$_2$, the ligand is DPPF, the base is potassium carbonate, and the solvent is tetrahydrofuran.

27. The method of claim 24 wherein compound 100 is prepared according to the following reaction scheme,

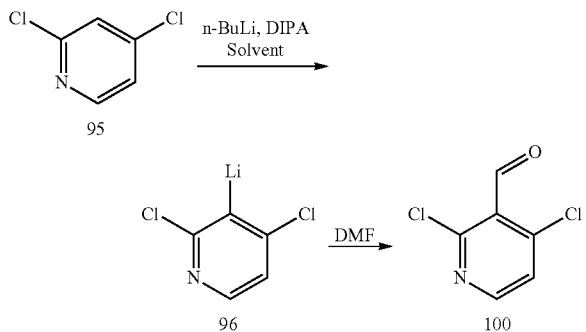

the method comprising:
(i) forming a first reaction mixture comprising compound 95, n-butyl lithium, diisopropylamine, and a polar aprotic solvent, and reacting the first reaction mixture to form a first reaction product mixture comprising compound 96;

(ii) admixing the first reaction product mixture with dimethylformamide to form a second reaction mixture, and reacting the second reaction mixture to form a second reaction product mixture comprising compound 100; and (iii) isolating compound 100 from the second reaction product mixture, wherein the yield of compound 100 is at least 70% and wherein the purity of compound 100 is at least 90 area %.

28. The method of claim 27 wherein the polar aprotic solvent is THF; the mole ratio of n-butyl lithium to compound 95 is between 1:1 and 2:1; the first reaction mixture and the second reaction mixture are formed at a temperature of greater than −35° C.; the solvent volume to compound 95 weight in the first reaction mixture is from about 3:1 to about 10:1; the mole ratio of DMF to compound 95 is from about 1.1:1 to about 2:1; and the mole ratio of diisopropylamine to compound 95 is from about 1.2:1 to about 2:1.

29. The method of claim 24 further comprising preparing compound 200, stereoisomers thereof, geometric isomers thereof, tautomers thereof, and salts thereof,

200 by a method comprising:
(i) (1) forming a first reaction mixture comprising compound 170, a reducing agent, a base and a solvent, to reduce the aldehyde moiety of compound 170 to form compound 171, and
   (2) isolating compound 171 from the first product mixture,
(ii) (1) forming a second reaction mixture comprising compound 171, compound 182, a palladium catalyst, a solvent system comprising water, and a base, to form compound 200, and
   (2) isolating compound 200 from the second product mixture, according to the following scheme:

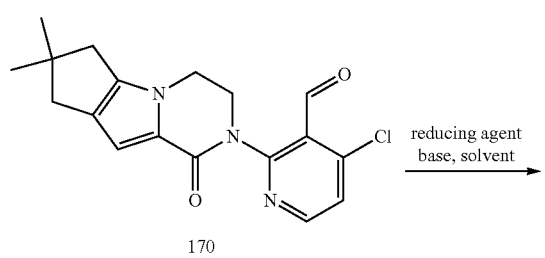

170

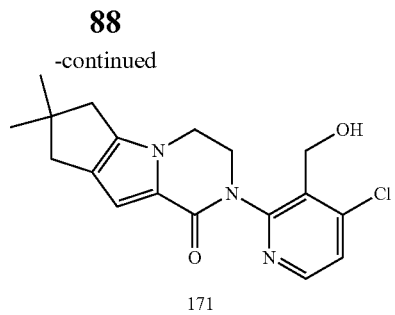

171

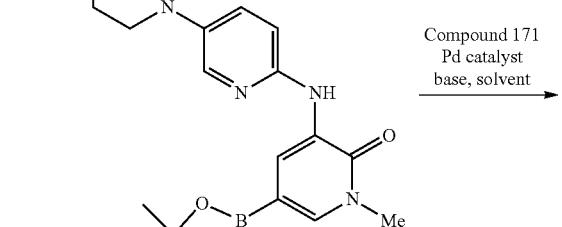

182

Compound 171
Pd catalyst
base, solvent

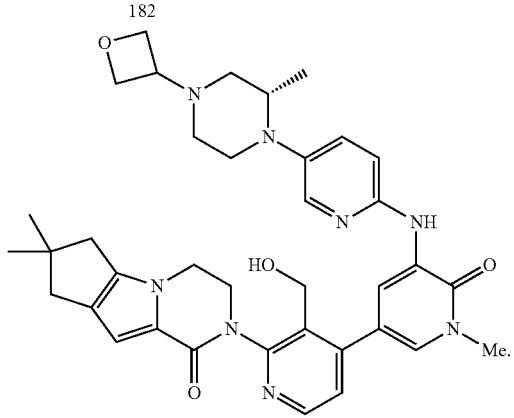

200

30. The method of claim 24, wherein the reducing agent in step (i) is NaBH$_4$.

31. The method of claim 24 wherein the base in step (i) is K$_2$HPO$_4$.

32. The method of claim 24 wherein the solvent in step (i) is THF.

33. The method of claim 24 wherein the Pd catalyst in step (ii) is Pd(PCy$_3$)$_2$.

34. The method of claim 24 wherein the base in step (ii) is K$_3$PO$_4$, Et$_3$N or Di-isopropylethylamine.

35. The method of claim 24 wherein the equivalent ratio of the Pd catalyst to compound 171 is less than 0.05:1.

36. The method of claim 24, wherein the ratio of compound 182 to compound 171 is greater than 1:1.

37. The method of claim 24 further comprising preparing compound 200, stereoisomers thereof, geometric isomers thereof, tautomers thereof, and salts thereof,

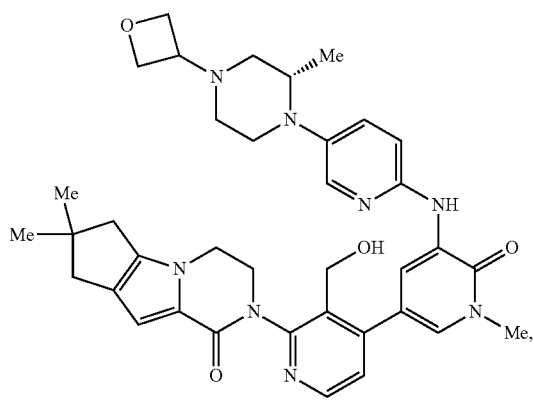

200

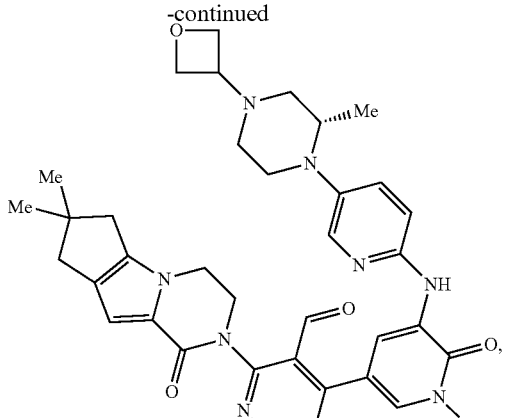

190 by a method comprising:

(i) (1) forming a first reaction mixture comprising compound 170, compound 181, a palladium catalyst, a solvent system comprising water, and a base, wherein the ratio of solvent volume to compound 170 weight in the reaction mixture is less than 20:1 liters per kg, the equivalent ratio of compound 181 to compound 170 is greater than 1:1, and the equivalent ratio of the palladium catalyst to compound 170 is from about 0.005:1 to about 0.05:1, (2) reacting the first reaction mixture to form a first reaction product mixture comprising compound 190 according to the following scheme:

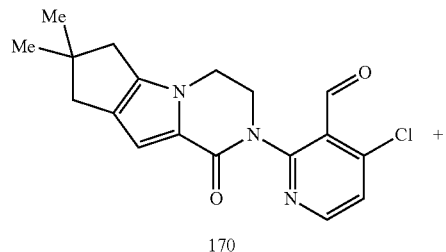

170

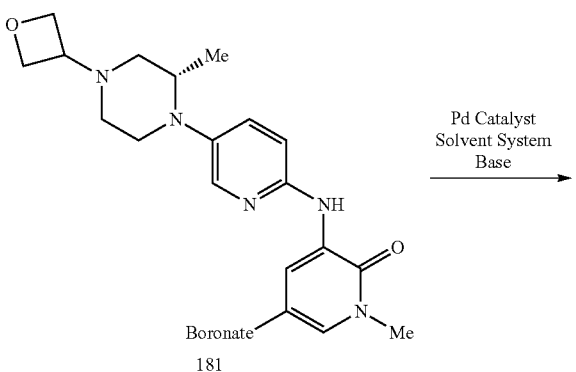

181 and (3) isolating compound 190 from the first reaction product mixture; and (ii) (1) forming a second reaction mixture comprising compound 190, a reducing agent, a base and a solvent, (2) reacting the second reaction mixture to reduce the aldehyde moiety of compound 190 and form a second reaction product mixture comprising compound 200, and (3) isolating compound 200 from the second reaction product mixture, wherein the yield of compound 190 is at least 50% based on compound 170, and the yield of compound 200 is at least 50% based on compound 190.

38. The method of claim 37 wherein the volume to weight ratio of the solvent system to compound 170 in the reaction mixture is from about 5:1 to about 20:1 liters per kg, the equivalent ratio of compound 181 to compound 170 is greater than 1:1, and the equivalent ratio of the palladium catalyst to compound 170 is from about 0.005:1 to about 0.02:1.

39. The method of claim 37 wherein:
(i) the catalyst is Pd(dppf)Cl$_2$.DCM;
(ii) (1) the base in the first reaction mixture is K$_3$PO$_4$, and (2) the solvent system in the first reaction mixture comprises water and tetrahydrofuran, wherein the volume ratio of water to tetrahydrofuran is from about 0.1:1 to about 0.4:1; and
(iii) (1) the base in the second reaction mixture is sodium hydroxide, and the equivalent ratio of sodium hydroxide to compound 190 is from about 0.3:1 to about 0.7:1, (2) the solvent in the second reaction mixture is selected from tetrahydrofuran, methyl tert-butyl ether, and 2-methyltetrahydrofuran, wherein the ratio of solvent volume to compound 190 weight is from about 4:1 to about 8:1 liters to kg, (3) the reducing agent is sodium borohydride, wherein the equivalent ratio of sodium borohydride to compound 190 is from about 0.2:1 to about 0.8:1, and (4) the boronate is 4,4,5,5-tetramethyl-1,3,2-dioxaborolane of the structure:

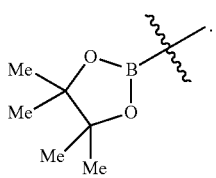 [SMILES: *B1OC(C)(C)C(C)(C)O1]

40. The method of claim 37 wherein:

the yield of compound 190 is at least 60%, and the purity of compound 190 is at least 99 area %; and the yield of compound 200 is at least 60%, and the purity of compound 200 is at least 99 area %.

41. The method of claim 37 wherein compound 181 is prepared by:

(i) forming a reaction mixture comprising compound 180, a palladium catalyst, a catalyst ligand, a borylation reagent, potassium acetate, and a polar aprotic solvent;

(ii) reacting the reaction mixture to form a reaction product mixture according to the following scheme:

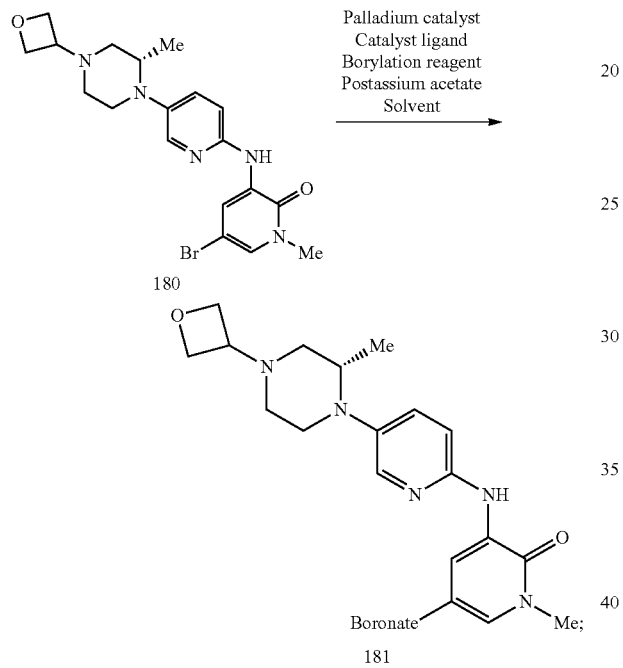

and (iii) isolating compound 181 from the reaction product mixture, wherein the yield of compound 181 is at least 85% and the purity of compound 181 is at least 95%.

42. The method of claim 41 wherein the reaction mixture comprises: a ratio of solvent volume to compound 180 weight of from about 5:1 to about 20:1 liters to kg; an equivalent ratio of borylation reagent to compound 180 of between 1 and 2; an equivalent ratio of palladium catalyst to compound 180 of from 0.001:1 to about 0.005:1; an equivalent ratio of catalyst ligand to catalyst of from about 1.5:1 to about 3; and an equivalent ratio of potassium acetate to compound 180 of greater than 1:1.

43. The method of claim 41 wherein the palladium catalyst is Pd$_2$(dba)$_3$, the catalyst ligand is an aryl phosphate ligand, the borylation reagent is bis(pinacolato)diboron, the solvent is tetrahydrofuran, the boronate is 4,4,5,5-tetramethyl-1,3,2-dioxaborolane, and boronate compound 181 is the species of compound 182:

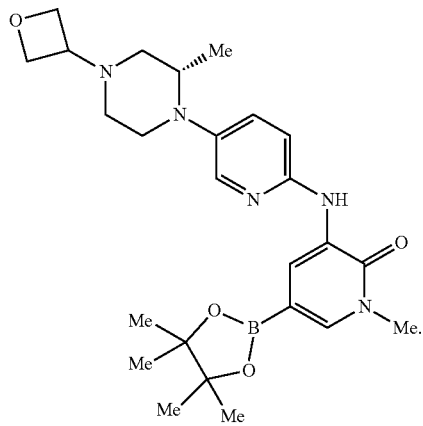

44. The method of claim 43 wherein the catalyst ligand is XPhos.

45. The method of claim 41 wherein compound 180 is prepared by:

(i) forming a reaction mixture comprising compound 141, compound 90, a palladium catalyst and an aryl phosphate catalyst ligand, a base, and an aprotic solvent;

(ii) reacting the reaction mixture to form a reaction product mixture according to the following scheme:

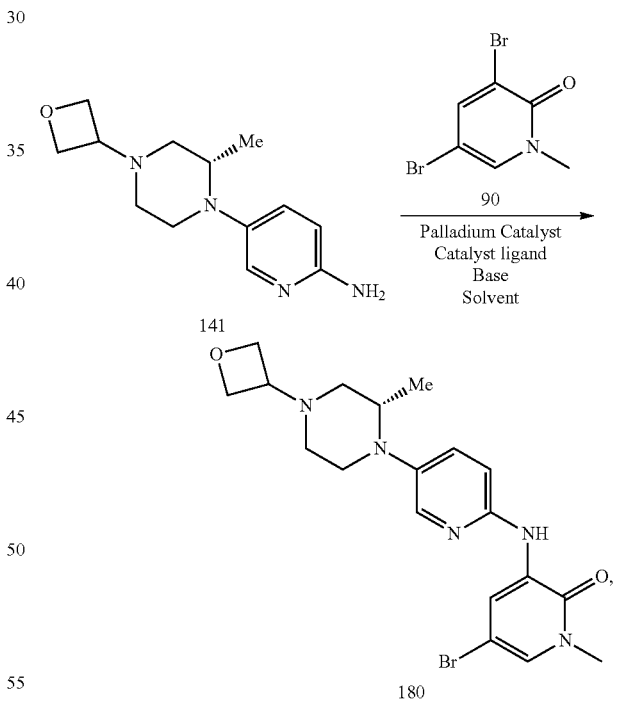

and (iii) isolating compound 180 from the reaction product mixture wherein the yield of compound 180 is at least 60%, and the purity of compound 180 is at least 95%.

46. The method of claim 45 wherein: the palladium catalyst is Pd$_2$(dba)$_3$; the catalyst ligand is Xantphos; the base is potassium carbonate or tripotassium phosphate wherein the equivalent ratio of the base to compound 141 is from about 1.5:1 to about 3:1; the reaction mixture comprises approximately equimolar amounts of compounds 141 and 90; the equivalent ratio of the palladium catalyst to compound 141 is from about 0.01:1 to about 0.03:1; the equivalent ratio of the catalyst ligand to the catalyst is from about 1.5:1 to about 3:1; and the solvent is selected from methyl tetrahydrofuran, tetrahydrofuran, dioxane, toluene, and combinations thereof.

47. The method of claim 45 wherein compound 141 is a solution of compound 141 in the solvent, wherein the solution comprises from about 5 to about 15 percent by weight compound 141 and less than 0.15 percent by weight methanol.

48. The method of claim 45 wherein compound 141 is prepared by:
(i) forming a reaction mixture comprising compound 140, a palladium on carbon catalyst, hydrogen, a solvent selected from methanol, ethanol, isopropanol, dioxane, toluene, and combinations thereof; and
(ii) reacting the reaction mixture to form a reaction product mixture according to the following scheme:

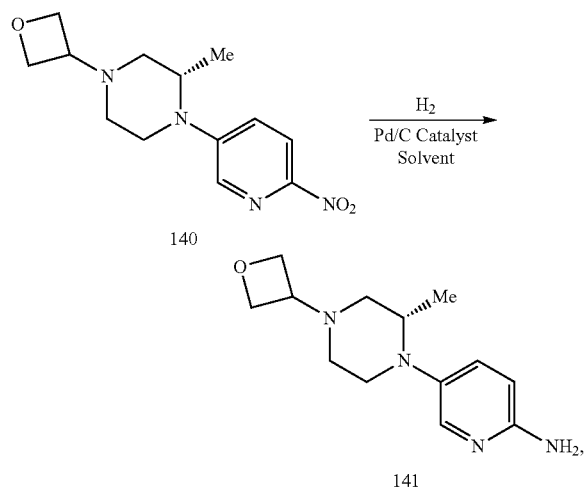

wherein the yield of compound 141 is at least 90%.

49. The method of claim 48 wherein the ratio of the solvent volume to compound 140 weight in the reaction mixture is from about 3:1 to about 20:1 liters to kg, and wherein the weight ratio of the catalyst to compound 140 is from about 10 w/w % to about 25 w/w %.

50. The method of claim 48 wherein compound 140 is prepared by:
(i) forming a reaction mixture comprising compound 153, compound 20, a solvent, NaBH(OAc)₃, acetic acid, and a drying agent;
(ii) reacting the reaction mixture to form a reaction product mixture according to the following scheme:

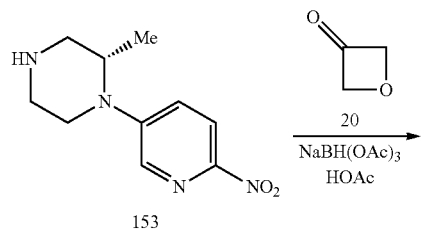

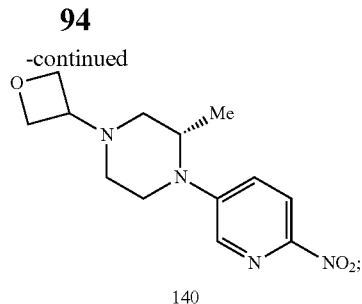

and
(iii) isolating compound 140 as a solid wherein the yield of compound 140 is at least 85%, and wherein the purity of compound 140 is at least 95%.

51. The method of claim 50 wherein: the equivalent ratio of compound 20 to compound 153 is from about 1.3:1 to about 1.9:1; the equivalent ratio of acetic acid to compound 153 is from about 1.1:1 to about 3:1; the equivalent ratio of NaBH(OAc)₃ to compound 153 is greater than 1.5:1.

52. The method of claim 50 wherein the solvent is selected from tetrahydrofuran, methyl tetrahydrofuran, dichloromethane, and combinations thereof, and compound 153 in solution in tetrahydrofuran, methyl tetrahydrofuran, dichloromethane, or a combination thereof, wherein the solution comprises from about 2 to about 10 percent by weight compound 153.

53. The method of claim 50 wherein the drying agent is magnesium sulfate and the equivalent ratio of magnesium sulfate to compound 153 is from about 0.3:1 to about 0.6:1.

54. The method of claim 50 wherein compound 153 is prepared by:
(i) forming a reaction mixture comprising compound 152 comprising protecting group PG, hydrochloric acid, and a solvent comprising water,
(ii) reacting the reaction mixture to form a reaction product mixture comprising deprotected compound 152 according to the following scheme:

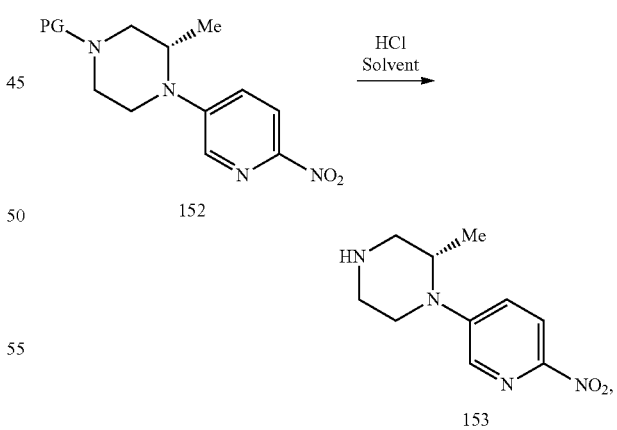

and
(iii) isolating compound 153 from the reaction product mixture wherein the yield of compound 153 is at least 80%.

* * * * *